US009512206B2

(12) United States Patent
Katsuragi et al.

(10) Patent No.: US 9,512,206 B2
(45) Date of Patent: Dec. 6, 2016

(54) ANTI-LIPOARABINOMANNAN ANTIBODY AND IMMUNOASSAY FOR ACID-FAST BACILLARY INFECTION USING THE ANTIBODY

(71) Applicant: OTSUKA PHARMACEUTICAL CO., LTD., Chiyoda-ku, Tokyo (JP)

(72) Inventors: Kiyonori Katsuragi, Osaka (JP); Masataka Togashi, Osaka (JP); Tetsuya Oda, Osaka (JP); Ryuta Ito, Osaka (JP); Chie Kawaguchi, Osaka (JP); Yoko Saijo, Osaka (JP); Daisuke Koga, Osaka (JP); Makoto Matsumoto, Osaka (JP); Mamoru Fujiwara, Osaka (JP); Kenji Ono, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/378,922

(22) PCT Filed: Feb. 28, 2013

(86) PCT No.: PCT/JP2013/055591
§ 371 (c)(1),
(2) Date: Aug. 14, 2014

(87) PCT Pub. No.: WO2013/129634
PCT Pub. Date: Sep. 6, 2013

(65) Prior Publication Data
US 2016/0083458 A1 Mar. 24, 2016

(30) Foreign Application Priority Data

Feb. 29, 2012 (JP) ................................ 2012-044796

(51) Int. Cl.
*G01N 33/00* (2006.01)
*A61K 49/16* (2006.01)
*A61K 39/04* (2006.01)
*C07K 16/12* (2006.01)
*G01N 33/569* (2006.01)
*C07K 16/00* (2006.01)

(52) U.S. Cl.
CPC ......... *C07K 16/1285* (2013.01); *C07K 16/005* (2013.01); *C07K 16/1289* (2013.01); *G01N 33/5695* (2013.01); *C07K 2317/35* (2013.01); *C07K 2317/622* (2013.01); *G01N 2333/35* (2013.01); *G01N 2400/50* (2013.01)

(58) Field of Classification Search
None
See application file for complete search history.

(56) References Cited

U.S. PATENT DOCUMENTS

| 2002/0034763 A1 | 3/2002 | Glatman-Freedman et al. |
| 2006/0222642 A1 | 10/2006 | Dominguez et al. |
| 2007/0041978 A1 | 2/2007 | Hattori et al. |
| 2012/0237530 A1 | 9/2012 | Matsuda et al. |

FOREIGN PATENT DOCUMENTS

| CN | 202083695 U | 12/2011 |
| JP | 2010-525808 A | 7/2010 |
| RU | 2 350 352 C2 | 3/2006 |
| WO | 2005/035756 A1 | 4/2005 |
| WO | 2008/136694 A1 | 11/2008 |
| WO | 2011/049082 A1 | 4/2011 |

OTHER PUBLICATIONS

Glatman-Freedman et al. 1996 (Monoclonal Antibodies to Surface Antigens of *Mycobacterium tuberculosis* and Their Use in a Modified Enzyme-Linked Immunosorbent Spot Assay for Detection of Mycobacteria; J of Clin Microb 34(11): 2795-2802).*
Communication dated Mar. 3, 2016 from Russian Patent Office in counterpart Application No. 2014138806.
Communication dated Aug. 31, 2015 from the European Patent Office in counterpart application No. 13755814.4.
Mason P R et al: "The use of monoclonal antibodies to identify mycobacteria grown in culture in Zimbabwe", Tubercle and Lung Disease, Churchill Livingstone Medical Journals, 1993, vol. 74, pp. 195-199.

(Continued)

*Primary Examiner* — Gary Nickol
*Assistant Examiner* — Mary Lyons
(74) *Attorney, Agent, or Firm* — Sughrue Mion, PLLC

(57) ABSTRACT

The present invention provides a monoclonal antibody that specifically binds to acid-fast bacillary lipoarabinomannan, particularly tubercle bacillary lipoarabinomannan, the antibody being set forth below:

Figure 2:
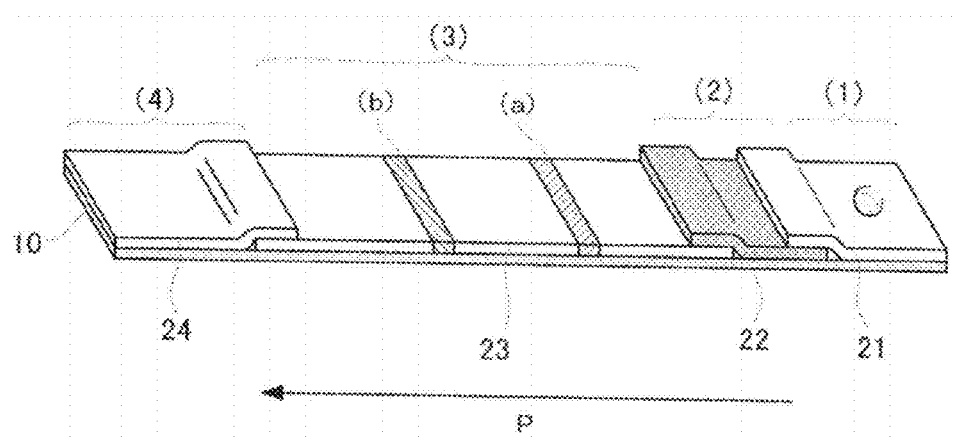

(A) a monoclonal antibody comprising a heavy chain variable region and a light chain variable region joined via a linker, the heavy chain variable region comprising heavy chains CDR1 to CDR3 shown in (a) to (c) below, and the light chain variable region comprising light chains CDR1 to CDR3 shown in (d) to (f) below:
(a) heavy chain CDR1 consisting of the amino acid sequence set forth in SEQ ID NO: 1,
(b) heavy chain CDR1 consisting of the amino acid sequence set forth in SEQ ID NO: 2,
(c) heavy chain CDR1 consisting of the amino acid sequence set forth in SEQ ID NO: 3,
(d) light chain CDR1 consisting of the amino acid sequence set forth in SEQ ID NO: 4,
(e) light chain CDR1 consisting of the amino acid sequence set forth in SEQ ID NO: 5, and
(f) light chain CDR1 consisting of the amino acid sequence set forth in SEQ ID NO: 6.

The present invention further provides the use of the antibody.

9 Claims, 14 Drawing Sheets

(56) References Cited

OTHER PUBLICATIONS

B. Hamasur et al: "A mycobacterial lipoarabinomannan specific monoclonal antibody and its F(ab')2 fragment prolong survival of mice infected with *Mycobacterium tuberculosis*", Clinical & Experimental Immunology, 2004, vol. 138, pp. 30-38.

Murase T et al: "Structural Insights into Antibody Recognition of Mycobacterial Polysaccharides", Journal of Molecular Biology, 2009, vol. 392, pp. 381-392.

Aharona Glatman-Freedman et al., "Monoclonal antibodies to surface antigens of *Mycobacterium tuberculosis* and their use in a modified Enzyme-Linked Immunosorbent Spot Assay for detection of Mycobacteria", Journal of Clinical Microbiology, Nov. 1996, pp. 2795-2802, vol. 34, No. 11.

Lenka M. Pereira Arias-Bouda et al., "Development of antigen detection assay for diagnosis of tuberculosis using sputum samples", Journal of Clinical Microbiology, Jun. 2000, pp. 2278-2283, vol. 38, No. 6.

Susi Prinzis et al, "Structure and antigenicity of lipoarabinomannan from *Mycobacterium bovis* BCG", Journal of General Microbiology, 1993, vol. 139, pp. 2649-2658.

Fujirebio Inc., Influenza Virus Kit ESPLINE® Influenza A&B-N Reagent for Detection of Influenza A & B Virus Antigens, 2011.

Beston Hamasur et al., "Rapid diagnosis of tuberculosis by detection of mycobacterial lipoarabinomannan in urine", Journal of Microbiological Methods, 2001, pp. 41-52, vol. 45.

C. Boehme et al., "Detection of mycobacterial lipoarabinomannan with an antigen-capture ELISA in unprocessed urine of Tanzanian patients with suspected tuberculosis", Transactions of the Royal Society of Tropical Medicine and Hygiene, 2005, pp. 893-900, vol. 99.

Jérôme Nigou et al., "Lipoarabinomannans: from structure to biosynthesis", Biochimie, 2003, pp. 153-166, vol. 85.

Greg Winter et al., "Making Antibodies by Phage Display Technology", Annu. Rev. Immunol., 1994, pp. 433-455, vol. 12.

Kathrin Zuberbuhler et al., "A general method for the selection of high-level scFv and IgG antibody expression by stably transfected mammalian cells", Protein Engineering, Design and Selection, 2009, pp. 169-174, vol. 22, No. 3.

Susmita Sarkar et al., "A Bispecific Antibody Based Assay Shows Potential for Detecting Tuberculosis in Resource Constrained Laboratory Settings", PLoS ONE, 2012, pp. 1-10, vol. 7, Issue 2, e32340.

International Search Report of PCT/JP2013/055591 dated Apr. 23, 2013 [PCT/ISA/210].

\* cited by examiner

FIG. 1
(A)
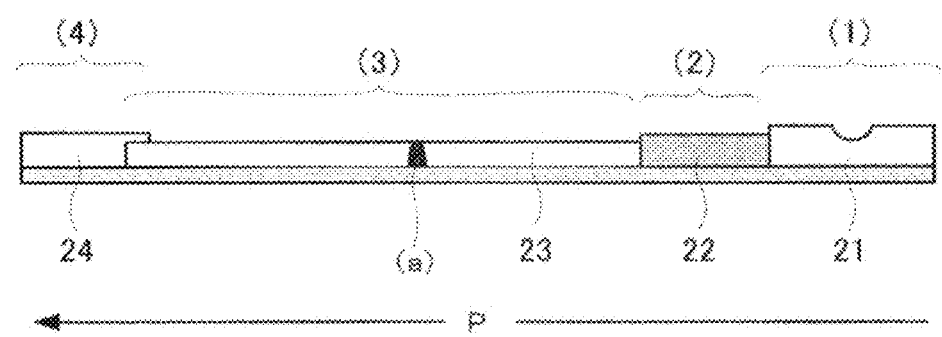
(B)
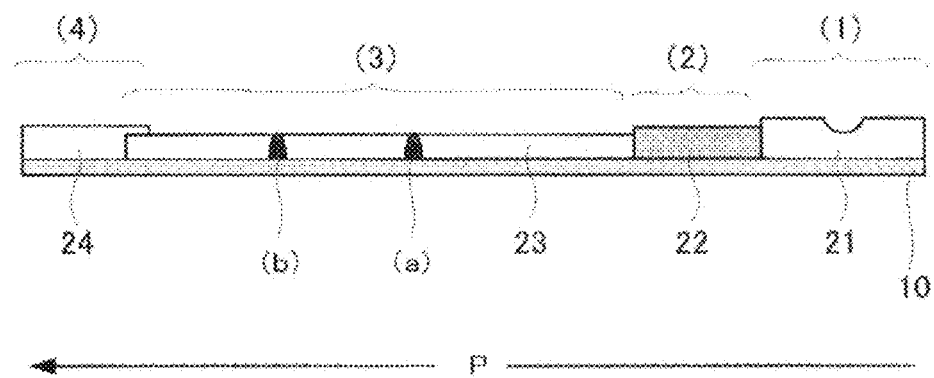

FIG. 4

```
              10         20         30         40         50
Myco-scFv   AQSVKESGGR LVTPGTPLTL TCTASGFTIT NYPMCWVRQA PGEGLEWIGC
TB-scFv     AQSVKESGGR LVTPGGSLTL TCTVSGIDLT TYYMTWIRQA PGKGLEWIGT
                                  CDR1=====            CDR2=

60         70         80         90        100
Myco-scFv   IEDSGRIKDA SWAKGRFTMS KTSSTTVDLK LTSPTTEDTA TYFCVRDAGW
TB-scFv     IDSYGNRYYA SWAKGQFTIS KTSSTTVDLK MTQLTASDTA TYFCTRDDLG
            ==================                         CDR3====

110        120        130        140        150
Myco-scFv   SWWTQLDLWG GGTLVTISSS SGGGGSGGDG SGGGGSELVM TQTPSSVSAA
TB-scFv     WNNDNI--WG PGTLVTVSSS SGGGGSGGGG SGGGGSELVM TQTPSSKSVP
            ========            linker-----------

160        170        180        190        200
Myco-scFv   VGDTVTIKCQ ANENI---GRF LAWFQQKPGQ RPKLLIYSAS SLASGVSSRF
TB-scFv     VGDTVTINCQ ASESVYGNNG LAWYQQKPGQ PPKLLIYKAS TLASGVPSRF
            CDR1=================            CDR2=========

210        220        230        240
Myco-scFv   SGSGYGTDFT LTISGVHCDD AASYYCLGGP NNVVDGASFG GGTEVVVK
TB-scFv     KGSGYGTQFT LTISDVVCDD AATYYCGGYK GSTTDGAAFG GGTEVVVK
                                  CDR3===============
```

FIG. 9

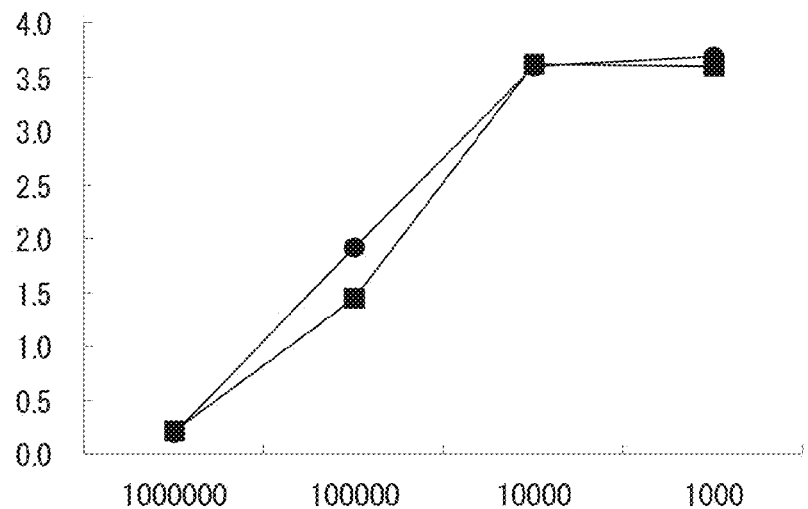

FIG. 10

```
              10         20         30         40         50
       MALPAAVTLD ESGGGLQTPG GVLSLVCKAS GFTFSSFNMH WVRQAPGKGL
                                        CDR1======

60         70         80         90        100
       EWVAGISGDD SRYTYTNYAP AVKGRATISR DNGQSTVRLQ LNNLRAEDTG
       CDR2====== ========== ======

110        120        130        140        150
       TYYCAKDFSD GSGADHIDAW GHGTEVIVSS GGGGSGGDGS GGGGSALTQP
       CDR3====== ==========      linker-------- ---- ---------- -----

160        170        180        190        200
       SSVSANPGET VKITCSGSSS WYGWYQQKSP GSAPVTLIYS NDKRPSNIPS
                  CDR1=====  ===                  CDR2= ======

210        220        230        240        250
       RFSGSLSGST NTLTITGVQV EDEAVYFCGT YDSSDRYIGI FGAGTTLTVL
                                        CDR3==  =========

260
       AAALEHHHHH H
```

FIG. 13
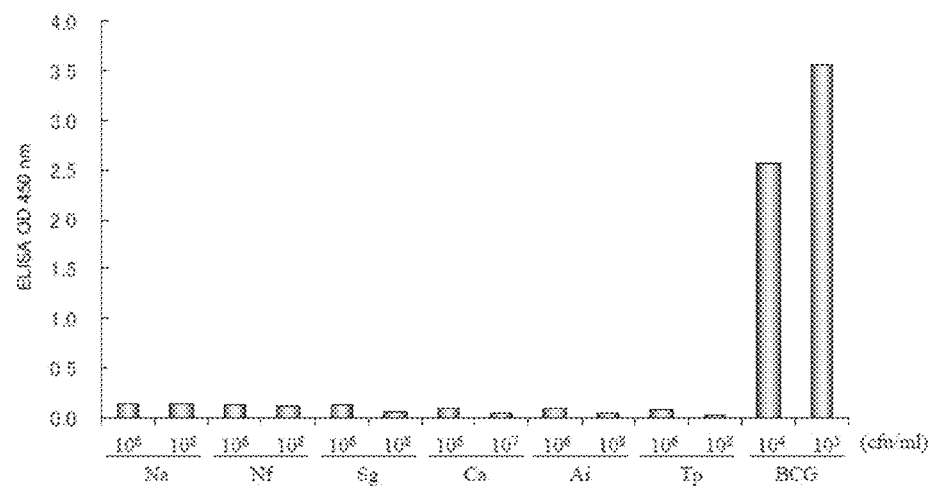
FIG. 14
A: Tubercle bacillus assay result
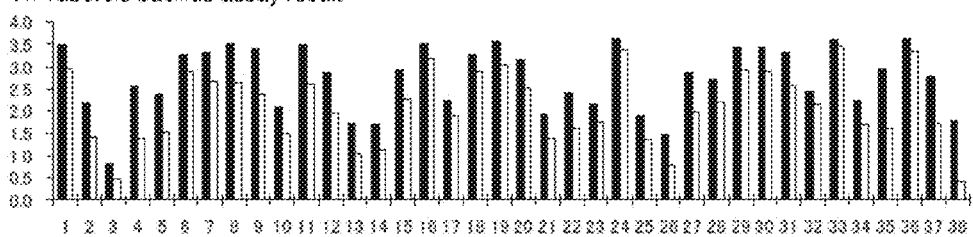
B: Non-tuberculous acid-fast bacillus assay result
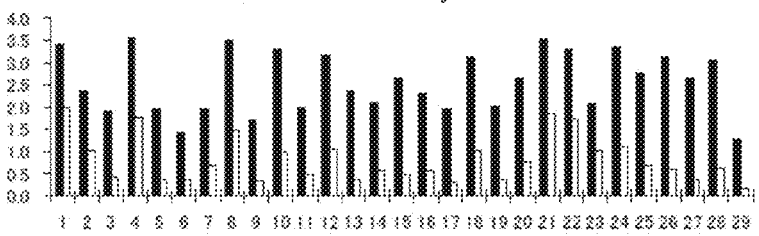

ary Infection Using the
ANTI-LIPOARABINOMANNAN ANTIBODY AND IMMUNOASSAY FOR ACID-FAST BACILLARY INFECTION USING THE ANTIBODY

CROSS REFERENCE TO RELATED APPLICATIONS

This is a National Stage of International Application No. PCT/JP2013/055591 filed Feb. 28, 2013, claiming priority based on Japanese Patent Application No. 2012-044796 filed Feb. 29, 2012, the contents of all of which are incorporated herein by reference in their entirety.

TECHNICAL FIELD

The present invention relates to a monoclonal antibody that specifically binds to lipoarabinomannan of acid-fast bacilli such as tubercle bacillus, and particularly to a single-chain antibody (scFv) and a multivalent antibody thereof.

The present invention further relates to a method for detecting acid-fast bacilli using the antibody, particularly to a method for diagnosing tuberculosis or a tuberculosis diagnostic method; and an acid-fast bacillus detection reagent (e.g., a tuberculosis diagnostic reagent) and an acid-fast bacillus detection kit (e.g., a tuberculosis diagnostic kit), which are for use in the above method.

The present invention further relates to a method for determining tuberculosis curative effect of an antituberculosis medicament using the antibody; and a kit for determining the curative effect of an antituberculosis medicament, which is for use in the above method.

BACKGROUND ART

Tuberculosis is an infectious disease that has been tormenting people for several thousand years, and it is estimated that ¼ of the adult population in Europe in the nineteenth century has died from tuberculosis. Thanks to improvement in living standards and the discovery of antibiotics in the twentieth century, tuberculosis has been virtually eradicated in industrialized nations by the 1950s. However, tuberculosis is still rampant as a recurrent infectious disease. In the present day, it is estimated that one in three people in the world population is infected with tubercle bacillus (latent tuberculosis). The total number of new-onset tuberculosis patients in the world is said to be 9.4 million, and it is estimated that 2 million patients among them die therefrom. Currently, approximately 95% of active tuberculosis patients live in developing countries, and 99% of people who die from tuberculosis are concentrated in developing countries.

In the 1990s, the world recognized anew that the number of tuberculosis cases has still continued to rise so as to be the greatest infectious disease centered in developing countries, and has set about to take full-fledged measures. Countermeasures against tuberculosis have been made under global cooperation, such as the deployment of Directly Observed Treatment, Short-Course (DOTS) most prominently by the World Health Organization (WHO), the establishment of "Stop Tuberculosis partnership" for advancing measures under cooperation of countries that are directly concerned, aid providing nations, and aid organization, and the founding of "The Global Fund to Fight AIDS, Tuberculosis and Malaria" as a system to provide financial support. Many of the existing technologies that are used as countermeasures against tuberculosis have been generally used for several tens of years without any improvements. Therefore, there is a pressing need to develop new technologies that are effective in developing countries.

For the diagnosis of tuberculosis, it is most important to discover tubercle bacillus infection at an early stage in order to initiate a therapy. In particular, since patients who are in a bacteria discharge state have an extremely high risk of spreading the infection to surrounding people, it is necessary to treat those patients in an isolated environment without any contact with the surrounding people. As a test for that, "Bacteriological diagnosis of tuberculosis" exists, and sputum smear test described therein is used most commonly.

The sputum smear test is a method for directly observing and examining a sputum smear sample under a microscope (direct microscopy of sputum smear sample), and was established by Robert Koch more than a century ago. Mycobacteria are identified in the clinical test sample by staining the pathogen of tuberculosis. The tuberculosis diagnostic method used today has been established by practically using the technology used by Koch. The tubercle bacillus smear test is a standard tuberculosis diagnostic method in developing countries, and is also used as a reference for evaluating performance of a new testing method.

Gene amplification method has been established as a method that has higher sensitivity than the sputum smear test. The gene amplification method is a method for amplifying a specific DNA fragment in a chain reaction manner using DNA polymerase. The principle of this method is amplification of DNA that is intended for testing, using DNA that is to be amplified, one pair of DNA primers that are complementary to sequences at both ends of the DNA, and a heat resistance DNA polymerase, and making repetitive temperature changes. Although the gene amplification method is satisfactory in term of sensitivity, it is difficult to use this method in developing countries due to operability, equipment, and cost.

As a recent global trend, because of the spread of multiple-medicament resistant tuberculosis, interest is directed toward the necessity of culture test and nucleic acid amplification test. However, among various bacteriological diagnostic methods that exist, the sputum smear test (direct microscopy of sputum) is still regarded as a central core of tuberculosis countermeasure strategies. Particularly in resource-poor developing countries in which tuberculosis is spreading, the sputum smear test is not only an effective diagnosis method, but also plays an important role as means for determining therapeutic effect.

As described above, although the sputum smear test is the central core of the basic strategy of tuberculosis control, the number of workers who perform bacteriological examination in many developing countries is absolutely insufficient, and it is said that quality of such workers is problematic. Since the effectiveness of this test depends on the skill of laboratory technicians, everyday training and quality control are essential, and these are causes for an extreme increase in overall cost. In addition, developing countries have many problems in social infrastructure required for improving laboratory environment, test instruments, testing technologies, and the like. These factors become entangled in a complicated manner, and, as a result, adversely affect quality of the test to no small extent.

Furthermore, since the sputum smear test is a test for detecting and identifying acid-fast bacilli but not a method for detecting tubercle bacilli, it is impossible to identify tubercle bacilli with the test.

Regarding tuberculosis therapy in advanced nations, therapy using a chemical agent is initiated after tubercle bacillus is identified; whereas in the DOTS program conducted in developing countries, therapy using a chemical agent is initiated when an acid-fast bacillus is detected in the sputum smear test without identifying the tubercle bacillus. Here, although chemical agents used for a tubercle bacillary infection and a nontuberculous-acid-fast bacillary infection are different, therapy is conducted for nontuberculous acid-fast bacilli basically using a chemical agent for tubercle bacilli since a highly therapeutic effect medicament for nontuberculous acid-fast bacilli has not been developed. Therefore, a patient has to bear the risk of side effects by the chemical agent. Representative examples of risks that have been pointed out include serious side effects such as decrease in liver function and loss of eyesight, and spread of medicament resistant nontuberculous acid-fast bacilli.

As described above, although there are several problems in hitherto known diagnosis of tuberculosis and therapy thereof, the sputum smear testing method developed by Koch in 1882 is still currently used for the diagnosis of tuberculosis without any large improvements. For the purpose of solving problems in developing countries and newly emerging countries regarding social infrastructure necessary for laboratory environment, test instruments, testing technologies, etc.; two measures are conceivable, i.e., "establishment of a highly sensitive and low cost testing method that enables high throughput processing of specimens collected at limited locations complete with power supply and facilities" or "establishment of Point Of Care Testing (POCT) that is highly sensitive, rapid, easy, and low cost, and that is conducted without using an instrument that requires a power supply."

Power supplies and facilities are put into place also in developing countries and newly emerging countries if it is in a very limited area. In addition, testing centers that perform relatively advanced tests already exist in such an area, and some wealthy patients can use those services. By utilizing such testing centers, problems such as laboratory environment, test instruments, testing technologies, and human resources can be solved. In such a case, it is necessary to transport a patient or a sputum specimen from a medical-examination scene to a testing center. There are several major restrictions in transporting sputum specimens used for a nucleic acid amplification test or a culture test. In order to prevent contamination and growth of unwanted germs, specimens have to be immediately refrigerated after sputum collection to be transported. Furthermore, since it is important for a culture test to keep bacteria in a growable state, more caution is required when compared to the genetic testing. Further, since both tests cannot be performed when a sterilization operation such as heat treatment is conducted on a specimen, specimens have to be transported in a strictly controlled state. Since a system that can handle such restrictions involved in specimen transport is not established in developing countries and newly emerging countries, it is important to establish an assay capable of detection even in specimens having a sterilization operation applied thereto.

When performing POCT, it is important to enable assay at a clinical scene in a short period of time without using special facilities and instruments. The technology used mostly for POCT is immunochromatographic test (ICT). Generally, ICT is considered inferior to immunoassay methods such as ELISA in terms of sensitivity. Therefore, if the problem were to be solved with POCT, it would be important to establish an assay system capable of high sensitivity detection. Furthermore, in the case with POCT, since it is difficult to take infection prevention measures for test workers by using safety cabinets and the like used in testing centers etc., sterilization treatment for reducing risk of infection from a specimen is essential.

Therefore, it is necessary to establish an assay capable of high sensitivity detection in sterilized specimens for "establishment of a highly sensitive and low cost testing method that enables high throughput processing of specimens collected at limited locations complete with power supply and facilities" and "establishment of Point Of Care Testing (POCT) that is highly sensitive, rapid, easy, and low cost, and that is conducted without using an instrument that requires a power supply." To do so, the selection of target antigen is important. As antigens specific for tubercle bacilli, protein antigens such as Ag85 are reported. However, since protein antigens are quickly degraded and digested in vivo, fine sensitivity can hardly be obtained therewith.

Major antigens in acid-fast bacilli include glycolipids that are major constituents of cell membranes and cell walls. Glycolipid antigens are considered to be one type of promising target antigens since they are highly stable in vivo. Among those, LAM accounts for 15% of bacterial cell components, and is an antigen that is gathering attention also in terms of its quantity. There are several reports of creating PoAb and MoAb for the purpose of detecting acid-fast bacillary LAM in live specimens (cf. Non-Patent Literatures 1 to 4 (NPL 1 to 4)). In couple of those reports, ELISA for detecting sputum or urinary lipoarabinomannan (hereinafter, also referred to as "LAM") is used. However, basic structures of LAMs in acid-fast bacilli are almost the same except for a minute difference observed in the structure of mannose cap. In particular, in *Mycobacterium avium* which is a bacterium that causes acid-fast bacillary infections second most frequently only behind tubercle bacillus, the mannose cap structure is almost the same as that of tubercle bacillus (cf. Non-Patent Literature 5 (NPL 5)). Therefore, there is a desire for a monoclonal antibody capable of specifically detecting LAM of tubercle bacilli among acid-fast bacilli.

CITATION LIST

Non-Patent Literature

NPL 1: Aharona Glatman-Freedman et al., "Monoclonal antibodies to surface antigens of *Mycobacterium tuberculosis* and their use in a modified Enzyme-Linked Immunosorbent Spot Assay for detection of Mycobacteria," Journal of Clinical Microbiology, November 1996, pp. 2795-2802

NPL 2: Lenka M. Pereira Arias-Bouda et al., "Development of antigen detection assay for diagnosis of tuberculosis using sputum samples," Journal of Clinical Microbiology, June 2000, pp. 2278-2283

NPL 3: Beston Hamasur et al., "Rapid diagnosis of tuberculosis by detection of acid-fast bacillary lipoarabinomannan in urine," Journal of Microbiological Methods, 45, 2001, pp. 41-52

NPL 4: C. Boehme et al., "Detection of acid-fast bacillary lipoarabinomannan with an antigen-capture ELISA in unprocessed urine of Tanzanian patients with suspected tuberculosis," Transactions of the Royal Society of Tropical Medicine and Hygiene, 99, 2005, pp. 893-900

NPL 5: Lipoarabinomannans: from structure to biosynthesis. Jérôme Nigou, Martine Gilleron, Germain Puzo, Biochimie 85 (2003) 153-166

NPL 6: Winter et al., Annu. Rev. Immunol., 12:433, 1994

NPL 7: K. Zuberbühler, Protein Engineering, Design & Selection, 22, 169 (2009)

SUMMARY OF INVENTION

Technical Problem

An object of the present invention is to provide a monoclonal antibody that specifically binds to lipoarabinomannan (hereinafter sometimes referred to as "LAM") of acid-fast bacilli, and particularly a single-chain antibody (scFv) and a multivalent antibody thereof.

Another object of the present invention is to provide a method for detecting acid-fast bacilli using the antibody, or a tuberculosis diagnostic method, an acid-fast bacillus detection reagent (e.g., a tuberculosis diagnostic reagent) and an acid-fast bacillus detection kit (e.g., a tuberculosis diagnostic kit) using the method.

A further object of the present invention is to provide a method for determining tuberculosis curative effect of an antituberculosis medicament using the antibody, and a kit for determining the curative effect of the antituberculosis medicament, which is for use in the above method.

Solution to Problem

By developing the technique for producing or selecting a suitable immune animal, immunogen, and MoAb, the present inventors successfully developed an antibody and an assay method that can distinguish acid-fast bacillary LAM from LAM of other bacteria or membrane antigens structurally similar thereto and specifically detect acid-fast bacillary LAM with high sensitivity that is comparable to that of gene amplification detection methods. Further, the present inventors successfully developed an antibody that can distinguish tubercle bacillary LAM from LAM of non-tuberculous acid-fast bacilli and specifically detect tubercle bacillary LAM.

Thus, the present invention includes the following embodiments.

(I) Monoclonal Antibody (I-1) that Specifically Binds to Lipoarabinomannan (LAM) of Acid-Fast Bacilli (I-1) A monoclonal antibody that is capable of binding to acid-fast bacillary LAM, the antibody being set forth in any one of (A) to (C) below:

(A) a monoclonal antibody comprising a heavy chain variable region and a light chain variable region joined via a linker, the heavy chain variable region comprising heavy chains CDR1 to CDR3 shown in (a) to (c) below, and the light chains comprising CDR1 to CDR3 shown in (d) to (f) below:
   (a) a heavy chain CDR1 consisting of the amino acid sequence set forth in SEQ ID NO: 1,
   (b) a heavy chain CDR2 consisting of the amino acid sequence set forth in SEQ ID NO: 2,
   (c) a heavy chain CDR3 consisting of the amino acid sequence set forth in SEQ ID NO: 3,
   (d) a light chain CDR1 consisting of the amino acid sequence set forth in SEQ ID NO: 4,
   (e) a light chain CDR2 consisting of the amino acid sequence set forth in SEQ ID NO: 5, and
   (f) a light chain CDR3 consisting of the amino acid sequence set forth in SEQ ID NO: 6;

(B) a monoclonal antibody comprising a heavy chain variable region and a light chain variable region joined via a linker, the heavy chain variable region comprising heavy chains CDR1 to CDR3 shown in (g) to (i) below, and the light chains comprising CDR1 to CDR3 shown in (j) to (l) below:
   (g) a heavy chain CDR1 consisting of the amino acid sequence set forth in SEQ ID NO: 31,
   (h) a heavy chain CDR2 consisting of the amino acid sequence set forth in SEQ ID NO: 32,
   (i) a heavy chain CDR3 consisting of the amino acid sequence set forth in SEQ ID NO: 33,
   (j) a light chain CDR1 consisting of the amino acid sequence set forth in SEQ ID NO: 34,
   (k) a light chain CDR2 consisting of the amino acid sequence set forth in SEQ ID NO: 35, and
   (l) a light chain CDR3 consisting of the amino acid sequence set forth in SEQ ID NO: 36; and (C) a monoclonal antibody comprising a heavy chain variable region and a light chain variable region joined via a linker, the heavy chain variable region comprising heavy chains CDR1 to CDR3 shown in (m) to (o) below, and the light chains comprising CDR1 to CDR3 shown in (p) to (r) below:
   (m) a heavy chain CDR1 consisting of the amino acid sequence set forth in SEQ ID NO: 47,
   (n) a heavy chain CDR2 consisting of the amino acid sequence set forth in SEQ ID NO: 48,
   (o) a heavy chain CDR3 consisting of the amino acid sequence set forth in SEQ ID NO: 49,
   (p) a light chain CDR1 consisting of the amino acid sequence set forth in SEQ ID NO: 50,
   (q) a light chain CDR2 consisting of the amino acid sequence set forth in SEQ ID NO: 51, and
   (r) a light chain CDR3 consisting of the amino acid sequence set forth in SEQ ID NO: 52.

(I-2) The monoclonal antibody according to (I-1) wherein the heavy chain variable region of the monoclonal antibody of (A) consists of the amino acid sequence set forth in SEQ ID NO: 7.

(I-3) The monoclonal antibody according to (I-1) or (I-2) wherein the light chain variable region of the monoclonal antibody of (A) consists of the amino acid sequence set forth in SEQ ID NO: 8.

(I-4) The monoclonal antibody according to any one of (I-1) to (I-3) wherein the linker of the monoclonal antibody of (A) has the amino acid sequence set forth in SEQ ID NO: 11.

(I-5) The monoclonal antibody according to any one of (I-1) to (I-4) wherein the monoclonal antibody of (A) consists of the amino acid sequence set forth in SEQ ID NO: 12.

(I-6) The monoclonal antibody according to any one of (I-1) to (I-5) wherein the monoclonal antibody of (A) is capable of specifically binding to tubercle bacillary LAM, preferably human tubercle bacillus (*M. tuberculosis*).

(I-7) The monoclonal antibody according to (I-1) wherein the heavy chain variable region of the monoclonal antibody of (B) consists of the amino acid sequence set forth in SEQ ID NO: 37.

(I-8) The monoclonal antibody according to (I-1) or (I-7) wherein the light chain variable region of the monoclonal antibody of (B) consists of the amino acid sequence set forth in SEQ ID NO: 38.

(I-9) The monoclonal antibody according to any one of (I-1), (I-7), and (I-8) wherein the linker of the monoclonal antibody of (B) has the amino acid sequence set forth in SEQ ID NO: 40.

(I-10) The monoclonal antibody according to any one of (I-1) and (I-7) to (I-9) wherein the monoclonal antibody of (B) consists of the amino acid sequence set forth in SEQ ID NO: 39.

(I-11) The monoclonal antibody according to (I-1) wherein the heavy chain variable region of the monoclonal antibody of (C) consists of the amino acid sequence set forth in SEQ ID NO: 53.

(I-12) The monoclonal antibody according to (I-1) or (I-11) wherein the light chain variable region of the monoclonal antibody of (C) consists of the amino acid sequence set forth in SEQ ID NO: 54.

(I-13) The monoclonal antibody according to any one of (I-1), (I-11), and (I-12) wherein the linker of the monoclonal antibody of (C) has the amino acid sequence set forth in SEQ ID NO: 11.

(I-14) The monoclonal antibody according to any one of (I-1) and (I-11) to (I-13) wherein the monoclonal antibody of (C) consists of the amino acid sequence set forth in SEQ ID NO: 30.

(I-15) The monoclonal antibody according to any one of (I-1) and (I-7) to (I-14) wherein the monoclonal antibody of (B) or (C) is capable of specifically binding to a non-tuberculous acid-fast bacillus.

(I-16) The monoclonal antibody according to any one of (I-1) to (I-15) wherein the monoclonal antibody of any one of (A) to (C) is a monovalent or bivalent antibody.

(II) Method for Immunizing a Non-Human Animal to Produce a Monoclonal Antibody that Specifically Binds to Acid-Fast Bacillary Lipoarabinomannan (LAM), and Method for Producing the Monoclonal Antibody (II-1) A method for immunizing a non-human animal to produce a monoclonal antibody that specifically binds to acid-fast bacillary LAM, the method comprising administering BCG as an immunogen to the non-human animal to induce a humoral immune response to BCG.

(II-2) The method according to (II-1) wherein the non-human animal is a rabbit or a chicken.

(II-3) The method according to (II-1) or (II-2) wherein the acid-fast bacillum is a tubercle bacillus, preferably human tubercle bacillus (*M. tuberculosis*).

(II-4) A method for producing a monoclonal antibody that specifically binds to acid-fast bacillary LAM, the method comprising the steps of:
administering BCG as an immunogen to a non-human animal to induce a humoral immune response to BCG and produce an antibody that binds to acid-fast bacillary LAM; and
collecting cells that produce the antibody from the non-human animal.

(II-5) A method for producing a monoclonal antibody that specifically binds to acid-fast bacillary LAM, the method comprising the steps of:
administering BCG as an immunogen to a non-human animal to induce a humoral immune response to BCG;
preparing mRNA encoding an antibody that binds to acid-fast bacillary LAM from the non-human animal;
preparing cDNA using the mRNA as a template; and collecting a monoclonal antibody that specifically binds to acid-fast bacillary LAM, by a phage display method using the cDNA.

(II-6) The method according to (II-4) or (II-5) wherein the non-human animal is a rabbit or a chicken.

(II-7) The method according to any one of (II-4) to (II-6) wherein the acid-fast bacillum is a tubercle bacillus, preferably human tubercle bacillus (*M. tuberculosis*).

(II-8) The method according to any one of (II-4) to (II-7) wherein the monoclonal antibody that specifically binds to acid-fast bacillary LAM is the monoclonal antibody according to any one of (I-1) to (I-12).

(II-9) The method according to any one of (II-4) to (II-8) wherein the monoclonal antibody that specifically binds to tubercle bacillary LAM, preferably human tubercle bacillus (*M. tuberculosis*) LAM, is the monoclonal antibody of (A) according to any one of (I-1) to (I-6).

(II-10) A method for producing a monoclonal antibody that specifically binds to acid-fast bacillary LAM, the method comprising the steps of:
administering a complex of LAM and the monoclonal antibody of (A) according to any one of (I-1) to (I-6) as an immunogen to a non-human animal to induce a humoral immune response to the complex and produce an antibody that binds to acid-fast bacillary LAM; and
collecting cells that produce the antibody from the non-human animal.

(II-11) A method for producing a monoclonal antibody that specifically binds to acid-fast bacillary LAM, the method comprising the steps of:
administering a complex of LAM and the monoclonal antibody of (A) according to any one of (I-1) to (I-6) as an immunogen to a non-human animal to induce a humoral immune response to the complex;
preparing mRNA encoding an antibody that binds to acid-fast bacillary LAM from the non-human animal;
preparing cDNA using the mRNA as a template; and harvesting a monoclonal antibody that specifically binds to acid-fast bacillary LAM, by a phage display method using the cDNA.

(II-12) The method according to (II-10) or (II-11) wherein the monoclonal antibody that specifically binds to acid-fast bacillary LAM is the monoclonal antibody of (B) according to any one of (I-1) and (I-7) to (I-12).

(III) Method for Detecting Acid-Fast Bacilli, Preferably Tubercle Bacillus (III-1) A method for detecting an acid-fast bacillus, preferably tubercle bacillus, the method comprising the steps of:
(1) bringing the monoclonal antibody according to any one of (I-1) to (I-16) into contact with a subject's biological sample; and
(2) assaying the acid-fast bacillus, preferably tubercle bacillus, that exists in the sample using, as an index, a binding reaction between the monoclonal antibody and acid-fast bacillary LAM, preferably tubercle bacillary LAM.

(III-2) The method according to (III-1) wherein the method for detecting tubercle bacillus uses the monoclonal antibody of (A) according to any one of (I-1) to (I-6).

Among the above detection methods, the tubercle bacillus detection method can be paraphrased as a method for diagnosing tuberculosis in patients (a tuberculosis diagnostic method).

(IV) Tuberculosis Diagnostic Reagent and Tuberculosis Diagnostic Kit (IV-1) A tuberculosis diagnostic reagent comprising the monoclonal antibody of (A) according to any one of (I-1) to (I-6).

(IV-2) A tuberculosis diagnostic kit comprising the monoclonal antibody of (A) according to any one of (I-1) to (I-6) as a tuberculosis detection reagent.

(V) Method for Measuring Acid-Fast Bacillary Lipoarabinomannan (LAM)

(V-1) A method for measuring acid-fast bacillary LAM in a test sample, comprising the steps of:
(1) bringing the monoclonal antibody according to any one of (I-1) to (I-16) into contact with the test sample that may contain an acid-fast bacillus; and (2) assaying acid-fast bacillary LAM in the test sample using a binding reaction between the monoclonal antibody and acid-fast bacillary LAM as an index.

(V-2) The method according to (V-1) which is an acid-fast bacillary LAM qualification method comprising detecting acid-fast bacillary LAM as step (2), or an acid-fast bacillary LAM quantification method comprising quantifying acid-fast bacillary LAM as step (2).

(V-3) The method according to (V-1) or (V-2) wherein the acid-fast bacillus is a tubercle bacillus, preferably human tubercle bacillus (*M. tuberculosis*).

(V-4) The method according to (V-3) wherein the monoclonal antibody is the monoclonal antibody of (A) according to any one of (I-1) to (I-6).

(VI) Acid-Fast Bacillary Lipoarabinomannan (LAM) Detection Reagent or Detection Kit (VI-1) An acid-fast bacillary LAM detection reagent comprising the monoclonal antibody according to any one of (I-1) to (I-16).

(VI-2) An acid-fast bacillary LAM detection reagent comprising the monoclonal antibody of (A) according to any one of (I-1) to (I-6).

(VI-3) The reagent according to (VI-2) wherein the acid-fast bacillus is a tubercle bacillus, preferably human tubercle bacillus (*M. tuberculosis*).

(VI-4) An acid-fast bacillary LAM detection kit comprising the monoclonal antibody according to any one of (I-1) to (I-16) as an acid-fast bacillary LAM detection reagent.

(VI-5) The acid-fast bacillary LAM detection kit according to (VI-4) wherein the monoclonal antibody is the monoclonal antibody of (A) according to any one of (I-1) to (I-6).

(VI-6) The acid-fast bacillary LAM detection kit according to (VI-5) wherein the acid-fast bacillus is a tubercle bacillus, preferably human tubercle bacillus (*M. tuberculosis*).

(VII) Assay Using a Sterilized Specimen (VII-1) A method for determining the presence or absence of acid-fast bacillary infection in a test sample, comprising the steps of:

(1) sterilizing the test sample by boiling, preferably by autoclaving;
(2) bringing the monoclonal antibody according to any one of (I-1) to (I-16), preferably the monoclonal antibody of (A) or (B) according to any one of (I-1) to (I-6) and (1-7) to (I-10), into contact with the sterilized sample;
(3) assaying acid-fast bacillary LAM in the test sample using a binding reaction between the monoclonal antibody and acid-fast bacillary LAM as an index; and
(4) determining that the test sample is infected with an acid-fast bacillus when acid-fast bacillary LAM is detected in the test sample.

(VII-2) The method according to (VII-1) wherein the monoclonal antibody is the monoclonal antibody of (A) or (B) according to any one of (I-1) to (I-6) and (I-7) to (I-10), and the acid-fast bacillus is tubercle bacillus.

(VIII) Method for Determining Tuberculosis Curative Effect of an Antituberculosis Medicament (VIII-1) A Method for Determining Tuberculosis Curative Effect of an Antituberculosis Medicament, Comprising the Steps of:

(1) bringing the monoclonal antibody of (A) according to any one of (I-1) to (I-6) into contact with both test samples before and after administration of the antituberculosis medicament;
(2) assaying tubercle bacillary LAM in the test samples before and after the administration of the antituberculosis medicament using a binding reaction between the monoclonal antibody and tubercle bacillary LAM as an index; and
(3) determining that the antituberculosis medicament has tuberculosis curative effect when tubercle bacillary LAM is detected in the test sample before the administration of the antituberculosis medicament and when tubercle bacillary LAM is not detected in the test sample after the administration of the antituberculosis medicament.

(VIII-2) A method for determining tuberculosis curative effect of an antituberculosis medicament, comprising the steps of:

(1) bringing the monoclonal antibody of (A) according to any one of (I-1) to (I-6) into contact with both test samples before and after administration of the antituberculosis medicament;
(2) quantifying tubercle bacillary LAM in the test samples before and after the administration of the antituberculosis medicament using a binding reaction between the monoclonal antibody and tubercle bacillary LAM as an index; and
(3) comparing the amount of tubercle bacillary LAM in the test sample after administration of the antituberculosis medicament (post-administration measurement) to the amount of tubercle bacillary LAM in the test sample before administration of the antituberculosis medicament (pre-administration measurement); and determining that the antituberculosis medicament has tuberculosis curative effect when the post-administration measurement is lower than the pre-administration measurement, and determining that the antituberculosis medicament does not have tuberculosis curative effect when the post-administration measurement is not lower than the pre-administration measurement.

(IX) Kit for Determining Tuberculosis Curative Effect of an Antituberculosis Medicament (IX) A kit for determining tuberculosis curative effect of an antituberculosis medicament, comprising the monoclonal antibody of (A) according to any one of (I-1) to (I-6).

(X) Acid-Fast Bacillus (Tubercle Bacillus) Detection Tool (X-1) An acid-fast bacillus, preferably tubercle bacillus, detection tool comprising a solution-absorbing piece formed from a material capable of transferring a test sample through capillary action, the solution-absorbing piece comprising:

(1) a sample collection part for absorbing and collecting a test sample;
(2) a labeled antibody part supporting a labeled monoclonal antibody according to any one of (I-1) to (I-16) that specifically reacts with acid-fast bacillary LAM;
(3) a determination part including a test result display part (a) having immobilized thereon an unlabeled monoclonal antibody according to any one of (I-1) to (I-16) that specifically reacts with acid-fast bacillary LAM; and
(4) a solution absorption part for absorbing remaining solution of the test sample that has moved through the sample collection part, the labeled antibody part, and the determination part.

(X-2) The acid-fast bacillus, preferably tubercle bacillus, detection tool according to (X-1), wherein the determination part (3) further comprises a control display part (b) having immobilized thereon an unlabeled antibody that reacts with the labeled monoclonal antibody according to any one of (I-1) to (I-16), the control display part being disposed apart from the test result display part (a).

(X-3) The acid-fast bacillus detection tool according to (X-1) or (X-2) wherein the monoclonal antibody is the monoclonal antibody of (A) according to any one of (I-1) to (I-6) and the acid-fast bacillus is a tubercle bacillus, preferably human tubercle bacillus (*M. tuberculosis*).

Advantageous Effects of Invention

According to the present invention, acid-fast bacilli that exist in a subject's biological sample (sputum, saliva, blood, lung lavage fluid, gastric juice, urine, feces, skin, or pancreatic juice) can be distinguished from other bacteria and specifically detected. The method for detecting acid-fast bacilli according to the present invention has a sensitivity and a specificity that are comparable to those of gene amplification detection methods. Because the method for detecting acid-fast bacilli according to the present invention can determine the amount of acid-fast bacilli in a living body, curative effect on acid-fast bacilli, particularly tuberculosis, can be monitored. Further, the method for detecting acid-fast bacilli according to the present invention can reliably and accurately detect acid-fast bacilli even from sterilized target specimens for at least one week after the sterilization. Therefore, even in an area having no special specimen transport system for preventing infection, specimens, if sterilized, can be transported by general transport systems, such as via mail.

According to a preferred embodiment of the present invention, tubercle bacillus that exists in a tuberculosis patient's biological sample can be distinguished from non-tuberculous acid-fast bacilli and specifically detected. Therefore, the present invention can diagnose tubercle bacillus infection with high accuracy. Furthermore, curative effects of antituberculosis medicaments in tuberculosis patients can be determined with high accuracy.

BRIEF DESCRIPTION OF DRAWINGS

In FIG. 1, (A) and (B) are both diagrams showing (side view) modes of a tubercle bacillus detection tool (tubercle bacillary LAM detection tool) of the present invention. Diagram (A) shows a mode in which a determination part (3) has a test result display part (a) only, and diagram (B) shows a mode in which the determination part (3) has both the test result display part (a) and a control display part (b). The reference characters in the figure indicate the following. 10: support body, 21: sheet forming sample collection part (1), 22: sheet forming labeled antibody part (2), 23: sheet forming determination part (3), 24: sheet forming solution absorption part (4), (a): test result display part, (b): control display part, (1): sample collection part, (2): labeled antibody part, (3): determination part, (4): solution absorption part, P: arrow showing flow direction of test sample. (The same applies for FIG. 2).

FIG. 2 shows (perspective view) one mode of the tubercle bacillus detection tool (tubercle bacillary LAM detection tool) of the present invention.

FIG. 3 shows a result of measuring antibody titer in blood of rabbits each subcutaneously immunized with BCG vaccine or killed bacterial cells of H37Ra, through ELISA method using antigen plates having immobilized thereon LAM of *M. tuberculosis* (-■-) and LAM of *M. avium* (-●-) (Reference Example 1 (2)). (A) shows a result from rabbits immunized with BGC vaccine, and (B) shows a result from rabbits immunized with killed bacterial cells of H37Ra.

FIG. 4 shows amino acid sequences of scFv having LAM reactivity. More specifically, comparison is made between the upper row showing an amino acid sequence (SEQ ID NO: 30) of scFv (Myco-scFv) produced from spleen cells of a rabbit immunized with killed bacterial cells of H37Ra and the lower row showing an amino acid sequence (SEQ ID NO: 12) of scFv (TB-scFv) produced from spleen cells of a rabbit immunized with BCG vaccine, together with respective positions of regions of CDR1 to CDR3 in heavy chain variable regions, a linker, and regions of CDR1 to CDR3 in light chain variable regions. It should be noted that, with respect to a linker sequence having four serine residues bound to its N-terminal, an amino acid region on the N-terminal side shows the VH region, and a region on the C-terminal side shows the VL region.

FIG. 5 shows a result of LAM reactivity evaluation of TB-scFv. LAM reactivity of TB-scFv produced from a rabbit immunized with BCG vaccine was evaluated with ELISA using plates having LAM of *M. tuberculosis* and LAM of *M. avium* immobilized thereon. In FIG. 5, "■" indicates reactivity against LAM of *M. tuberculosis* and "●" indicates reactivity against *M. avium.*

FIG. 6 shows a result of evaluation of an acid-fast bacillary LAM detection ELISA and a tubercle bacillary LAM detection ELISA. Reactivity against LAM in the acid-fast bacillary LAM detection ELISA and the tubercle bacillary LAM detection ELISA was evaluated using purified LAM of *M. tuberculosis* and LAM of *M. avium*. In FIG. 6, "●" indicates reactivity against LAM of *M. tuberculosis* in the acid-fast bacillary LAM detection ELISA, "■" indicates reactivity against LAM of *M. avium* in the acid-fast bacillary LAM detection ELISA, "○" indicates reactivity against LAM of *M. tuberculosis* in the tubercle bacillary LAM detection ELISA, and "□" indicates reactivity against LAM of *M. avium* in the tubercle bacillary LAM detection ELISA.

FIGS. 7A-D shows an evaluation result of antibody combination. Evaluation of the antibody combination was conducted with the acid-fast bacillary LAM detection ELISA and the tubercle bacillary LAM detection ELISA using acid-fast bacillary clinical isolates. Reactivity against each of the strains is shown with density of color. In FIG. 7, myco indicates results from the acid-fast bacillary LAM detection ELISA, and TB indicates results from the tubercle bacillary LAM detection ELISA.

FIG. 8 shows evaluation results of an acid-fast bacillary LAM detection immunochromatography test and a tubercle bacillary LAM detection immunochromatography test. Reactivity against LAM in the acid-fast bacillary LAM detection immunochromatography and the tubercle bacillary LAM detection immunochromatography was evaluated using purified LAM of *M. tuberculosis* (A and B) and LAM of *M. avium* (C and D). In each of the figures, "myco" indicates a result of the acid-fast bacillary LAM detection immunochromatography test and "TB" indicates a result of the tubercle bacillary LAM detection immunochromatography test.

FIG. 9 shows chicken antiserum's antibody titer against LAM (Example 5). In FIG. 9, "-●-" indicates reactivity against purified LAM of Aoyama B strain of tubercle bacillus (*M. tuberculosis*), and "-■-" indicates reactivity against purified LAM of *M. avium.*

FIG. 10 shows an amino acid sequence (SEQ ID NO: 39) of a single-chain antibody G3-scFv isolated from a chicken scFv library, together with positions of regions of CDR1, CDR2, and CDR3 in the heavy chain variable region, a GS linker region, and regions of CDR1, CDR2, and CDR3 in the light chain variable region.

FIG. 11 shows reactivity of LAM detection ELISA using a bivalent antibody (Example 7). In FIG. 11, "-●-" indicates reactivity against BCG in the tubercle bacillary LAM detection ELISA, and "-■-" indicates reactivity against BCG in the acid-fast bacillary LAM detection ELISA.

Figure 12:
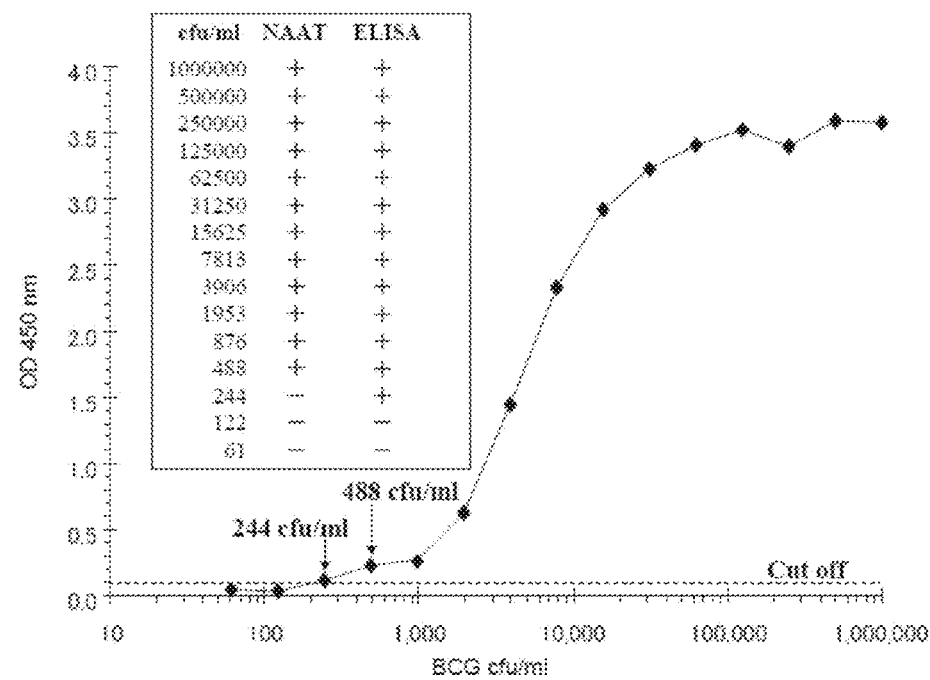

FIG. 12 shows detection sensitivity of the acid-fast bacillary LAM detection ELISA using a bivalent antibody (Example 8). In the figure, the table is a comparison of detection sensitivity between nucleic acid amplification test (NAAT) and the acid-fast bacillary LAM detection ELISA.

FIG. 13 shows a result of a cross-reactivity test for the acid-fast bacillary LAM detection ELISA with respect to oral bacteria (Example 9). In the figure, "Na" means bacterial cells of N. asteroides, "Nf" means bacterial cells of N. farcinica, "Sg" means bacterial cells of Streptomyces, "Ca" means bacterial cells of C. albicans, "Ai" means bacterial cells of Actinomycete, and "Tp" means bacterial cells of T. paurometabolum. Shown here are results of the acid-fast bacillary LAM detection ELISA conducted using LAM extracted from each of these cultured bacterial cells and cultured BCG bacterial cells.

FIG. 14 shows reactivity against acid-fast bacillary clinical isolates in LAM detection ELISA using a bivalent antibody (Example 10). In the figure, "A" shows assay results of 38 clinical isolates of tubercle bacillus, and "B" shows assay results of 29 strains of nontuberculous acid-fast bacilli (23 strains of *M. avium*, 6 strains of *M. intracellulare*). Both in A and B in the figure, black bars represents assay results from the acid-fast bacillary LAM detection ELISA, and white bars represents assay results from the tubercle bacillary LAM detection ELISA. Of the 29 strains of nontuberculous acid-fast bacilli in B, Nos. 1 to 23 are the results of the 23 strains of *M. avium*, and Nos. 24 to 29 are the results of the 6 strains of *M. intracellulare*.

Figure 15:
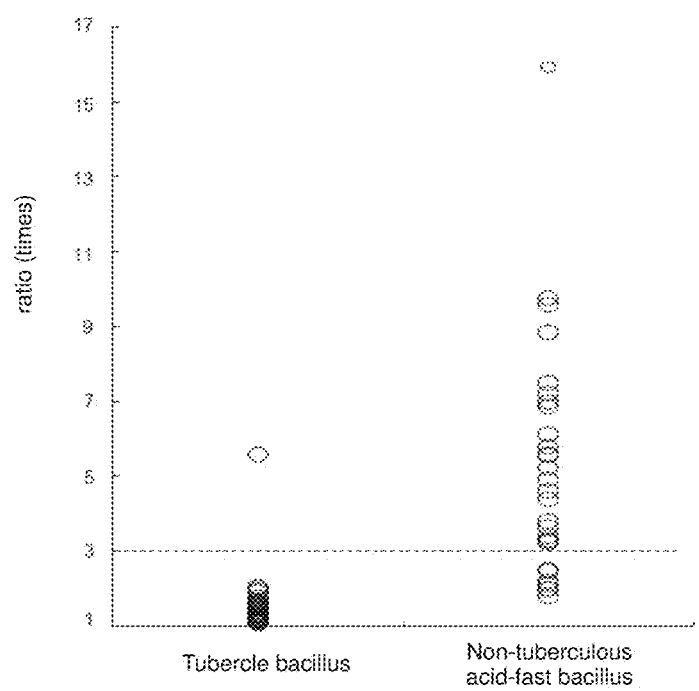

FIG. 15 shows ratios (value from the acid-fast bacillary LAM detection ELISA/value from the tubercle bacillary LAM detection ELISA) of reactivity in the acid-fast bacillary LAM detection ELISA and the tubercle bacillary LAM detection ELISA.

Figure 16:
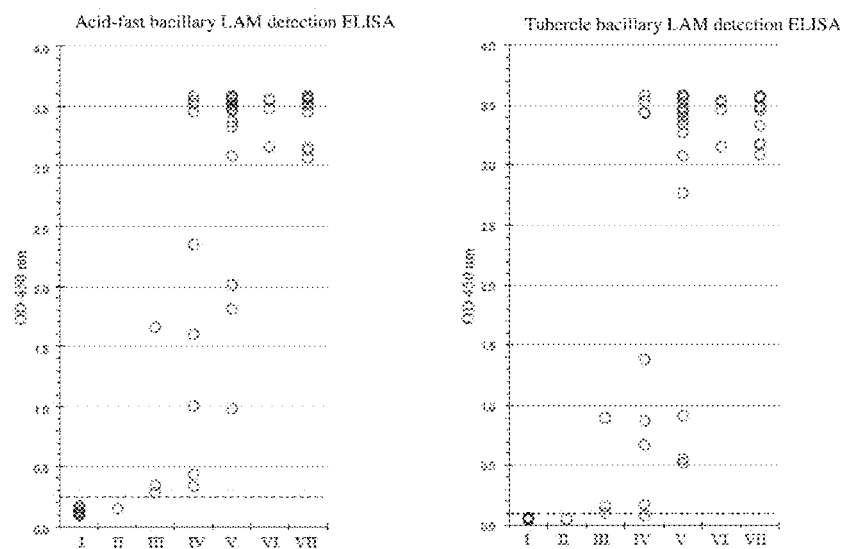

FIG. 16 shows reactivity against clinical sputum specimens in the tubercle bacillary LAM detection ELISA (left figure) and in the acid-fast bacillary LAM detection ELISA using a bivalent antibody (right figure) (Example 11). In the figure, "I" shows results of a specimen group found to be negative in smear test (direct smear test) and negative in nucleic acid amplification test, "II" shows results of specimens found to be "scanty" in smear test and negative in nucleic acid amplification test, "III" shows results of a specimen group found to be negative in smear test and positive in nucleic acid amplification test, "IV" shows results of a specimen group found to be "scanty" in smear test and positive in nucleic acid amplification test, "V" shows results of a specimen group who scored 1+ in smear test, "VI" shows results of a specimen group who scored 2+ in smear test, and "VII" shows results of a specimen group who scored 3+ in smear test. It should be noted that specimens who scored equal to or higher than 1+ in smear test are all positive in nucleic acid amplification test. Furthermore, dashed lines show provisional cutoff values.

Figure 17:
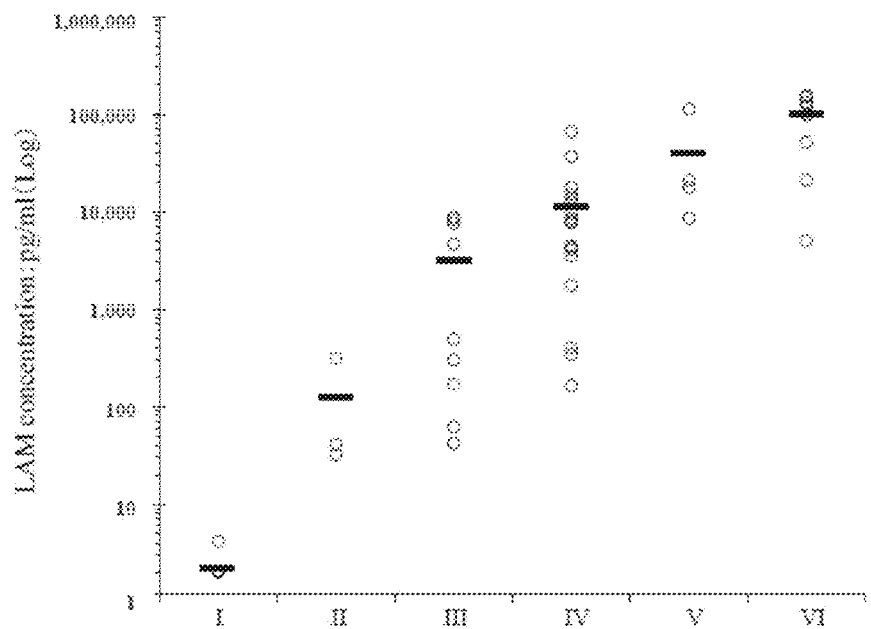

FIG. 17 shows the correlation between number of bacterial cells and concentration of LAM detected in LAM detection ELISA (Example 11). In the figure, "I" shows results of a specimen group found to be negative in smear test and negative in nucleic acid amplification test, "II" shows results of a specimen group found to be negative in smear test and positive in nucleic acid amplification test, "III" shows results of a specimen group found to be "scanty" in smear test and positive in nucleic acid amplification test, "IV" shows results of a specimen group who scored 1+ in smear test, "V" shows results of a specimen group who scored 2+ in smear test, and "VI" shows results of a specimen group who scored 3+ in smear test. It should be noted that specimens that scored equal to or higher than 1+ in smear test are all positive in nucleic acid amplification test. Furthermore, a line in each of the specimen groups indicates an average value of LAM concentration.

Figure 18:
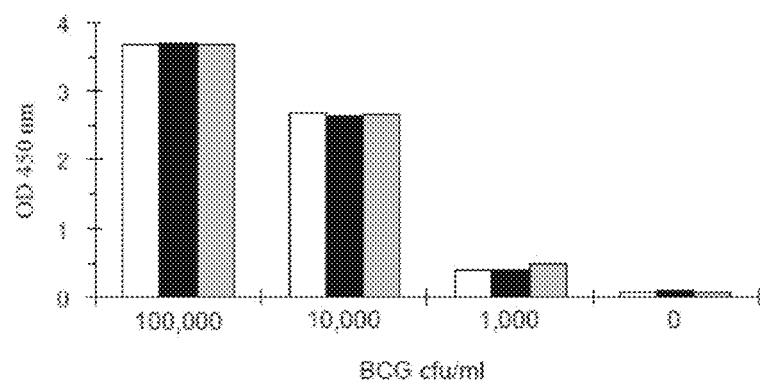

FIG. 18 shows stability of acid-fast bacillary LAM against sterilization treatment. White bars show assay results of bacterial cells that have not been sterilized, black bars show assay results of bacterial cells that have been boiled at 100° C. for 30 minutes, and gray bars show assay results of bacterial cells that have been sterilized in high pressure steam (autoclaved at 121° C. for 15 minutes) (Example 12).

Figure 19:
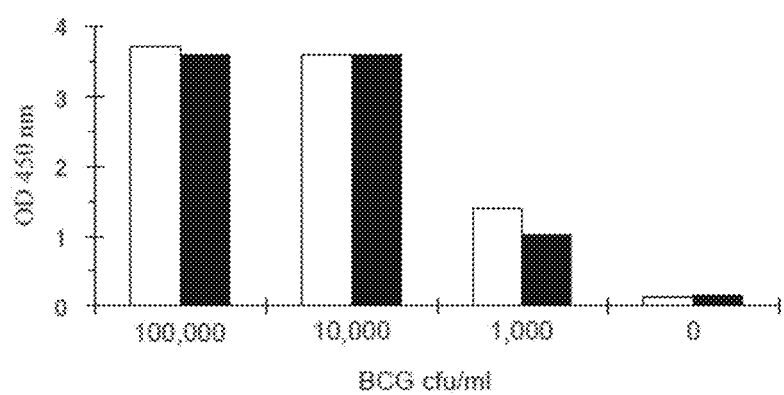

FIG. 19 shows storage stability of LAM after high pressure steam sterilization treatment (autoclaving). White bars show assay results of bacterial cells immediately after high pressure steam sterilization treatment, and black bars show assay results of bacterial cells that have been left at 25° C. for 7 days after high pressure steam sterilization treatment (Example 12).

DESCRIPTION OF EMBODIMENTS (I) Monoclonal Antibody that Specifically Binds to Acid-Fast Bacillary LAM Tubercle bacilli belong to the genus *Mycobacterium* of the family Mycobacteriaceae, and are a type of a bacterial group referred together with other bacteria belonging to the genus *Mycobacterium* as acid-fast bacilli. However, tubercle bacilli are distinguished from other acid-fast bacilli (nontuberculous acid-fast bacilli) by the fact that they can grow at 37° C. but not at 28° C. and by the fact that they have a heat resistance catalase. Four types of tubercle bacilli are known, i.e., tubercle bacillus (*Mycobacterium tuberculosis*, human tubercle bacillus), bovine tubercle bacillus (*M. bovis*, bovine tubercle bacillus, bovine bacillus), *Mycobacterium africanum* (*M. africanum*), and vole tubercle bacillus (*M. microti*). Among these, human tubercle bacillus (*M. tuberculosis*) is pathogenic for human as a bacterium causing tuberculosis, and *M. bovis* and *M. africanum* infect human on rare occasions. *M. microti* is not pathogenic for human. Furthermore, BCG is obtained by attenuating *M. bovis* through successive long-term subculturing, and is used as a vaccine (attenuated live bacteria vaccine) for tuberculosis prevention.

A monoclonal antibody (hereinafter, also referred to as "MoAb") that is a subject of the present invention is an antibody that distinguishes and specifically recognizes an acid-fast bacilli from other bacteria existing in vivo. More specifically, it is an antibody that distinguishes lipoarabinomannan (LAM) of acid-fast bacilli from other LAM-like antigens of bacteria, and specifically binds to LAM of acid-fast bacilli. LAM described here is a one of the main lipoglycans forming cell membranes and cell walls of bacteria in the genus *Mycobacterium* (acid-fast bacilli) including tubercle bacilli. Ordinarily, LAM includes a mannosyl phosphatidylinositol anchor (MPI), a sugar backbone including a D-mannan core and a D-arabinan domain, and a capping motif. However, depending on the type of bacteria, there are differences in the number of residues of sugar (e.g., mannose) included within a molecule, branched structure of a sugar chain, the number of acyl groups, and the type of fatty acids forming the acyl groups.

Specifically, the MoAb of the present invention includes an antibody with a structure in which a heavy chain variable region including heavy chain CDR1 to CDR3 of the following (a) to (c), and a light chain variable region including light chain CDR1 to CDR3 of the following (d) to (f) are connected through a linker. For convenience, this MoAb is also referred to as "MoAb1."
(a) Heavy chain CDR1 consisting of the amino acid sequence set forth in SEQ ID NO: 1.
(b) Heavy chain CDR2 consisting of the amino acid sequence set forth in SEQ ID NO: 2.
(c) Heavy chain CDR3 consisting of the amino acid sequence set forth in SEQ ID NO: 3.
(d) Light chain CDR1 consisting of the amino acid sequence set forth in SEQ ID NO: 4.
(e) Light chain CDR2 consisting of the amino acid sequence set forth in SEQ ID NO: 5.
(f) Light chain CDR3 consisting of the amino acid sequence set forth in SEQ ID NO: 6.

Furthermore, specifically, the MoAb of the present invention includes an antibody with a structure in which a heavy chain variable region including heavy chain CDR1 to CDR3 of the following (g) to (i), and a light chain variable region including light chain CDR1 to CDR3 of the following (j) to (l) are connected through a linker. For convenience, this MoAb is also referred to as "MoAb2."
(g) Heavy chain CDR1 consisting of the amino acid sequence set forth in SEQ ID NO: 31.
(h) Heavy chain CDR2 consisting of the amino acid sequence set forth in SEQ ID NO: 32.
(i) Heavy chain CDR3 consisting of the amino acid sequence set forth in SEQ ID NO: 33.
(j) Light chain CDR1 consisting of the amino acid sequence set forth in SEQ ID NO: 34.
(k) Light chain CDR2 consisting of the amino acid sequence set forth in SEQ ID NO: 35.
(l) Light chain CDR3 consisting of the amino acid sequence set forth in SEQ ID NO: 36.

Still further, specifically, the MoAb of the present invention includes an antibody with a structure in which a heavy chain variable region including heavy chain CDR1 to CDR3 of the following (m) to (o), and a light chain variable region including light chain CDR1 to CDR3 of the following (p) to (r) are connected through a linker. For convenience, this MoAb is also referred to as "MoAb3."
(m) Heavy chain CDR1 consisting of the amino acid sequence set forth in SEQ ID NO: 47.
(n) Heavy chain CDR2 consisting of the amino acid sequence set forth in SEQ ID NO: 48.
(o) Heavy chain CDR3 consisting of the amino acid sequence set forth in SEQ ID NO: 49.
(p) Light chain CDR1 consisting of the amino acid sequence set forth in SEQ ID NO: 50.
(q) Light chain CDR2 consisting of the amino acid sequence set forth in SEQ ID NO: 51.
(r) Light chain CDR3 consisting of the amino acid sequence set forth in SEQ ID NO: 52.

Here, "CDR" is an abbreviation of "Complementarity Determining Region" referred also as complementarity determining region. CDRs are regions that exist in a variable region of immunoglobulin, and are regions deeply involved in specific binding of an antibody to an antigen. Among those, "a heavy chain CDR" refers to a CDR that exists in a variable region of a heavy chain of immunoglobulin, and "a light chain CDR" refers to a CDR that exists in a variable region of a light chain of immunoglobulin.

The heavy chain variable region is a region including heavy chain CDR1 to CDR3, and the light chain variable region is a region including light chain CDR1 to CDR3. Although there is no particular limitation in the arrangement order of these CDR1 to CDR3, preferably, both in the heavy chain variable region and light chain variable region, CDR1, CDR2, and CDR3 are arranged in this order in a direction from the N-terminal side to the C-terminal side continuously or through other amino acid sequences.

The heavy chain variable region and/or light chain variable region of the MoAb of the present invention may have, as other amino acid sequences, an amino acid sequence referred to as a framework region (hereinafter, simply referred to as "FR") at a region in the above described variable regions excluding CDR1 to CDR3 described above. The amino acid sequence of the FR may be an amino acid sequence derived from a framework region (FR) of a heavy chain variable region or a light chain variable region of immunoglobulin, a variant thereof, or a partial modification thereof obtained by introducing a restriction enzyme recognition site at one part of the amino acid sequence derived from FR.

In the heavy chain variable regions of immunoglobulin, for example, a region between the N-terminal of the heavy chain variable region and CDR1 described above is defined as "FR1," a region between CDR1 and CDR2 is defined as "FR2," a region between CDR2 and CDR3 is defined as "FR3," and a region between CDR3 and the C-terminal of the heavy chain variable region is defined as "FR4." Similarly, in the light chain variable region of immunoglobulin, for example, a region between the N-terminal of the light chain variable region and CDR1 is defined as "FR1," a region between CDR1 and CDR2 is defined as "FR2," a region between CDR2 and CDR3 is defined as "FR3," and a region between "CDR3" and the C-terminal of the variable region is defined as "FR4."

These FRs have a function as a linker connecting each of the above described CDR1, CDR2, and CDR3 that are important as antigen recognition sequences, and are regions contributing to formation of three-dimensional conformation of variable regions.

In the MoAb1 of the present invention, the heavy chain variable region preferably has an amino acid sequence of 119 amino acid residues set forth in SEQ ID NO: 7, and the light chain variable region preferably has an amino acid sequence of 112 amino acid residues set forth in SEQ ID NO: 8. In SEQ ID NO: 7 showing the amino acid sequence of the heavy chain variable region, a region from the N-terminal to the 30th amino acid corresponds to "FR1" of the heavy chain variable region, an amino acid region from the 31st amino acid to the 35th amino acid corresponds to "CDR1" (SEQ ID NO: 1) of the heavy chain variable region, an amino acid region from the 36th amino acid to the 49th amino acid corresponds to "FR2," an amino acid region from the 50th amino acid to the 65th amino acid corresponds to "CDR2" (SEQ ID NO: 2), an amino acid region from the 66th amino acid to the 96th amino acid corresponds to "FR3," an amino acid region from the 97th amino acid to the 106th amino acid corresponds to "CDR3" (SEQ ID NO: 3), and an amino acid region from the 107th amino acid to the 119th amino acid corresponds to "FR4."

Furthermore, in SEQ ID NO: 8 showing the amino acid sequence of the light chain variable region of the MoAb1 of the present invention, a region from the N-terminal to the 23rd amino acid corresponds to "FR1" of the light chain variable region, an amino acid region from the 24th amino acid to the 36th amino acid corresponds to "CDR1" (SEQ ID NO: 4) of the light chain variable region, an amino acid region from the 37th amino acid to the 51st amino acid corresponds to "FR2," an amino acid region from the 52nd amino acid to the 58th amino acid corresponds to "CDR2" (SEQ ID NO: 5), an amino acid region from the 59th amino acid to the 89th amino acid corresponds to "FR3," an amino acid region from the 90th amino acid to the 102nd amino acid corresponds to "CDR3" (SEQ ID NO: 6), and an amino acid region from the 103rd amino acid to the 112nd amino acid corresponds to "FR4."

In the MoAb2 of the present invention, the heavy chain variable region preferably has an amino acid sequence of 130 amino acid residues set forth in SEQ ID NO: 37, and the light chain variable region preferably has an amino acid sequence of 116 amino acid residues set forth in SEQ ID NO: 38. In SEQ ID NO: 37 showing the amino acid sequence of the heavy chain variable region, a region from the N-terminal to the 35th amino acid corresponds to "FR1" of the heavy chain variable region, an amino acid region from the 36th amino acid to the 40th amino acid corresponds to "CDR1" (SEQ ID NO: 31) of the heavy chain variable region, an amino acid region from the 41st amino acid to the 54th amino acid corresponds to "FR2," an amino acid region from the 55th amino acid to the 74th amino acid corresponds to "CDR2" (SEQ ID NO: 32), an amino acid region from the 75th amino acid to the 106th amino acid corresponds to "FR3," an amino acid region from the 107th amino acid to the 119th amino acid corresponds to "CDR3" (SEQ ID NO: 33), and an amino acid region from the 120th amino acid to the 130th amino acid corresponds to "FR4."

Furthermore, in SEQ ID NO: 38 showing the amino acid sequence of the light chain variable region of the MoAb2 of the present invention, a region from the N-terminal to the 20th amino acid corresponds to "FR1" of the light chain variable region, an amino acid region from the 21st amino acid to the 28th amino acid corresponds to "CDR1" (SEQ ID NO: 34) of the light chain variable region, an amino acid region from the 29th amino acid to the 44th amino acid corresponds to "FR2," an amino acid region from the 45th amino acid to the 51st amino acid corresponds to "CDR2" (SEQ ID NO: 35), an amino acid region from the 52nd amino acid to the 83rd amino acid corresponds to "FR3," an amino acid region from the 84th amino acid to the 95th amino acid corresponds to "CDR3" (SEQ ID NO: 36), and an amino acid region from the 96th amino acid to the 116th amino acid corresponds to "FR4."

In the MoAb3 of the present invention, the heavy chain variable region preferably has an amino acid sequence of 121 amino acid residues set forth in SEQ ID NO: 53, and the light chain variable region preferably has an amino acid sequence of 110 amino acid residues set forth in SEQ ID NO: 54. In SEQ ID NO: 53 showing the amino acid sequence of the heavy chain variable region, a region from the N-terminal to the 30th amino acid corresponds to "FR1" of the heavy chain variable region, an amino acid region from the 31st amino acid to the 35th amino acid corresponds to "CDR1" (SEQ ID NO: 47) of the heavy chain variable region, an amino acid region from the 36th amino acid to the 49th amino acid corresponds to "FR2," an amino acid region from the 50th amino acid to the 65th amino acid corresponds to "CDR2" (SEQ ID NO: 48), an amino acid region from the 66th amino acid to the 96th amino acid corresponds to "FR3," an amino acid region from the 97th amino acid to the 108th amino acid corresponds to "CDR3" (SEQ ID NO: 49), and an amino acid region from the 109th amino acid to the 121st amino acid corresponds to "FR4."

Furthermore, in SEQ ID NO: 54 showing the amino acid sequence of the light chain variable region of the MoAb3 of the present invention, a region from the N-terminal to the 23rd amino acid corresponds to "FR1" of the light chain variable region, an amino acid region from the 24th amino acid to the 34th amino acid corresponds to "CDR1" (SEQ ID NO: 50) of the light chain variable region, an amino acid region from the 35th amino acid to the 49th amino acid corresponds to "FR2," an amino acid region from the 50th amino acid to the 56th amino acid corresponds to "CDR2" (SEQ ID NO: 51), an amino acid region from the 57th amino acid to the 87th amino acid corresponds to "FR3," an amino acid region from the 88th amino acid to the 100th amino acid corresponds to "CDR3" (SEQ ID NO: 52), and an amino acid region from the 101st amino acid to the 110th amino acid corresponds to "FR4."

As long as advantageous effects of the MoAb1 and the MoAb2 of the present invention are not compromised, it is possible to introduce a mutation in any of the amino acid sequences corresponding to FR1 to FR4 of the heavy chain variable region set forth in SEQ ID NOS: 7, 37, and 53, and the amino acid sequences corresponding to FR1 to FR4 of the light chain variable region set forth in SEQ ID NOS: 8, 38, and 54. Here, unless mentioned otherwise in particular, "the advantageous effects of the MoAb1, MoAb2, and MoAb3 of the present invention" means binding to acid-fast bacillary LAM, and preferably means specific binding to acid-fast bacillary LAM. In particular, "the advantageous effect of the MoAb1 of the present invention" means binding to tubercle bacillary LAM, preferably means specific binding to tubercle bacillary LAM. Although there is no particular limitation also in the number of mutations that can be introduced, the number of introduced mutations may be set such that the amino acid sequence identity with that before mutation is 85% or higher, preferably 90% or higher, more preferably 95% or higher, and particularly preferably 98% or higher. It should be noted that introduction of mutation described here may include substitution, deletion, and insertion of an amino acid. Furthermore, a restriction enzyme recognition site may be introduced into FR1 of the heavy chain variable region and/or FR4 of the light/heavy chain variable regions.

Furthermore, FR1 to FR4 of the heavy chain variable region and FR1 to FR4 of the light chain variable region indicated in the MoAb1 and the MoAb3 are all amino acid sequences derived from rabbit, whereas FR1 to FR4 of the heavy chain variable region and FR1 to FR4 of the light chain variable region indicated in the MoAb2 are all amino acid sequences derived from chicken. However, as long as the advantageous effect of the MoAb of the present invention is not compromised, a framework region derived from any animal species may be used. Examples of such animal species may include, but not particularly limited to, human, rabbit, chicken, horse, cow, goat, sheep, dog, mouse, hamster, and rat. The amino acid sequences are preferably derived from rabbit, chicken, or human, and more preferably from human. It should be noted that the amino acid sequences of human-derived FR1 to FR4 are known in the art (Kabat, et al. US Department of Health AND human Services, NIH (1991), USA), and is described in, for example, a website by NCBI.

The MoAb of the present invention has a structure in which a heavy chain variable region and a light chain variable region having the above described configuration are connected through a linker. Regarding "the linker" here, there is no particular limitation as long as the advantageous effect of the MoAb of the present invention is not compromised, and examples thereof may include a peptide having a linker sequence formed of an amino acid sequence whose number of amino acid residues is ordinarily about 8 to 30, preferably about 8 to 20, and more preferably about 8 to 15. Examples of preferable linker sequences include, but not limited to, a GS linker sequence [(Gly-Gly-Gly-Ser: SEQ ID NO: 9)$_n$, (Gly-Gly-Gly-Gly-Ser: SEQ ID NO: 10)$_n$; n is the number of repeats] or the like. Preferably, a peptide having a sequence with 1 to 3 (n is an integer of 1 to 3) repeats of such a GS linker sequence is used as the linker. In Examples described later, a peptide (Example 1) having a sequence (GGGGSGGGGSGGGGS: SEQ ID NO: 11) with three repeats of the GS linker sequence, and a peptide (Example 6) having another sequence (GGGGSGGDGSGGGGS: SEQ ID NO: 40) are used as the linker.

A preferable mode of the MoAb1 of the present invention may be a single-chain antibody consisting of the amino acid sequence set forth in SEQ ID NO: 12. Furthermore, a preferable mode of the MoAb2 may be a single-chain antibody consisting of the amino acid sequence set forth in SEQ ID NO: 39. Furthermore, a preferable mode of the MoAb3 may be a single-chain antibody consisting of the amino acid sequence set forth in SEQ ID NO: 30.

Such monoclonal antibodies of the present invention include an antibody that distinguishes and specifically recognizes tubercle bacillus from nontuberculous acid-fast bacilli. More specifically, they include an antibody that distinguishes lipoarabinomannan (LAM) of tubercle bacillus from LAMs of nontuberculous acid-fast bacilli, and specifically binds to tubercle bacillary LAM. Examples of the monoclonal antibodies may include the MoAb1 described above. The tubercle bacillus that is distinguished from non-tubercle bacillary acid-fast bacilli and is specifically recognized by the MoAb of the present invention is preferably human tubercle bacillus (*M. tuberculosis*) and bovine tubercle bacillus (*M. bovis*), and more preferably is human tubercle bacillus (*M. tuberculosis*).

When reaction against tubercle bacillary LAM is compared through a competition method, specific binding with respect to tubercle bacillary LAM can be said to be occurring when the required amount of nontuberculous acid-fast bacilli LAM is 10 times or more of that of tubercle bacillary LAM. Furthermore, when LAM is detected through sandwiching by an immobilized antibody and a detection antibody, the MoAb of the present invention can be determined as having more preferable binding specificity with respect to tubercle bacillary LAM if reactivity to nontuberculous acid-fast bacilli LAM has been reduced to 1/100 of that to tubercle bacillary LAM.

Affinity of an antibody can be easily measured with a hitherto known technology of, for example, measuring a saturation binding isotherm of $^{125}$I labeled IgG or its fragment, or through non-linear regression analysis using homologous substitution of $^{125}$IgG by non-labeled IgG as described by Motlsky in Analyzing Data with GraphPad Prizm (1999), GraphPad Software Inc., San Diego, Calif. Other methods known in the art may be used for the measurement, and the method may be, for example, a method described in Scatchard et al. Ann. NY Acd. Sci., 51,660 (1949).

The MoAb of the present invention may be produced in accordance with, but not limited to, the phage display method (G. Smith, Science, 228, 1315 (1985)) using tubercle bacillus as an antigen. Here, examples of tubercle bacilli may include the above described tubercle bacillus (*Mycobacterium tuberculosis*, human tubercle bacillus), bovine tubercle bacillus (*M. bovis*, bovine tubercle bacillus, bovine bacillus), *Mycobacterium africanum*, and vole tubercle bacillus. Tubercle bacillus (*Mycobacterium tuberculosis*, human tubercle bacillus), bovine tubercle bacillus (*M. bovis*, bovine tubercle bacillus, bovine bacillus) and *Mycobacterium africanum* are preferable, and bovine tubercle bacillus is more preferable. As described above, BCG is obtained by attenuating bovine tubercle bacillus (*M. bovis*) through successive long-term subculturing.

A method for producing the MoAb of the present invention with phage display using the BCG as an antigen is described in Examples. As described above, a feature of the MoAb of the present invention is distinguishing and specifically recognizing acid-fast bacilli from other bacteria such as oral bacteria, and, more specifically, distinguishing acid-fast bacillary LAM from LAM-like antigens of other bacteria and specifically binding to acid-fast bacillary LAM. The feature is preferably distinguishing tubercle bacillus from nontuberculous acid-fast bacilli and specifically recognizing tubercle bacillus, and, more specifically, distinguishing tubercle bacillary LAM from nontuberculous acid-fast bacilli LAM and specifically binding to tubercle bacillary LAM. Such MoAb can be produced using BCG as an immunogen.

It should be noted that, as described above, BCG is an attenuated strain produced from bovine tubercle bacillus (*M. bovis*), and refers to bacteria having antigenicity but no or diminished toxicity against human. However, in the present invention, not only that, but a BCG vaccine produced using the bacteria is also referred to as "BCG."

Furthermore, the monoclonal antibody of the present invention includes a multivalent antibody that is a single-chain antibody described above. Although multivalent antibodies include bivalent antibodies, trivalent antibodies, and tetravalent antibodies, bivalent antibodies are preferable. These multivalent antibodies can be produced in accordance with a hitherto known method (Non-Patent Literature 7: K. Zuberbuhler, Protein Engineering, Design & Selection, 22, 169 (2009)). Specifically, a multivalent antibody can be produced by, for example, in the case with a bivalent antibody, connecting genes of a heavy chain and a light chain of a single-chain antibody using a gene of a constant region, cloning the connected genes in a vector capable of expressing that in mammalian cells, transforming mammalian cells with the vector including the genes, and culturing the cells.

(II) Method for Immunizing a Non-Human Animal to Produce a Monoclonal Antibody that Specifically Binds to Acid-Fast Bacillary LAM, Preferably Tubercle Bacillary LAM, and a Method for Producing the Monoclonal Antibody The present invention also relates to a method for immunizing a non-human animal to produce a MoAb that specifically binds to acid-fast bacillary LAM, and a method for producing the MoAb using the immunization method. More preferably, the present invention relates to a method for immunizing a non-human animal to produce a MoAb that specifically binds to tubercle bacillary LAM, and a method for producing the MoAb using the immunization method.

(II-1) Immunization Method

Basic structures of acid-fast bacillary LAMs are almost the same except for minute differences recognized in the structure of mannose cap. When producing an antibody against such acid-fast bacillary LAM, it is common to immunize a non-human animal using a standard strain human tubercle bacillus such as H37Rv as an immunogen. By doing so, an antibody that widely reacts to acid-fast bacillary LAM can be produced.

On the other hand, when a non-human animal is immunized using, as an immunogen, BCG, i.e., an attenuated strain produced from bovine tubercle bacillus (*M. bovis*) or a vaccine produced therefrom; it is possible to obtain a highly specific antibody that specifically binds to tubercle bacillary LAM, preferably, LAM of human tubercle bacillus, by distinguishing that from LAMs of nontuberculous acid-fast bacilli. The present invention provides, as a preferable mode, a method for immunizing a nonhuman animal using BCG as an immunogen (immunizing antigen), as an immunization method for producing a MoAb that specifically binds to LAM of human tubercle bacillus.

Here, a non-human animal may be an animal other than human, and examples thereof include mammals such as mouse, rat, hamster, guinea pig, rabbit, monkey, dog, goat, sheep, pig, horse, and cow, and birds such as chicken, duck, turkey, and quail. Mammals (small animals) such as mouse, rat, hamster, guinea pig, and rabbit are preferable, and rabbit is more preferable.

The immunization method of the present invention to produce a MoAb that specifically binds to tubercle bacillary LAM is characterized by immunizing a non-human animal using BCG as an immunogen (immunizing antigen); and the technique for immunization is not particularly limited and a method known in the art can be appropriately selected to be used.

Examples thereof include a method of administration through subcutaneous, intravenous, or intra-abdominal injection of BCG together with, if necessary, an adjuvant. Subcutaneous administration is preferable. Examples of the adjuvant may include, but not limited to, Complete Freund's adjuvant and Incomplete Freund's adjuvant. It should be noted that administration of BCG is preferably performed for about 2 to 5 times with an interval of about 2 weeks after the first administration (first immunization).

Spleen cells of a non-human animal immunized in such a manner are useful as cells for producing an antibody that is highly specific to tubercle bacillary LAM, preferably LAM of human tubercle bacillus. The spleen is removed from the immunized non-human animal in ten-odd days to several months after first immunization of BCG, and is used to produce and obtain the antibody that is highly specific to tubercle bacillary LAM, preferably LAM of human tubercle bacillus.

Specifically, for example, cells (antibody producing cells) prepared from a spleen removed from an immunized non-human animal are fused with myeloma cells in accordance with a hitherto known method using polyethylene-glycol method or electrical stimulation, and culturing the cells in HAT selection medium to obtain hybridomas. Then, by screening, from among the hybridomas, a hybridoma that produces an antibody which binds to tubercle bacillary LAM using a hitherto known method such as limiting dilution analysis, a hybridoma that produces a MoAb that is highly specific to tubercle bacillary LAM can be obtained. By culturing, with a hitherto known method, the hybridoma cloned in such a manner, it is possible to prepare and obtain a MoAb that is highly specific to LAM of a desired tubercle bacillus, preferably LAM of human tubercle bacillus.

Regardless whether it is tubercle bacillus or non-tuberculous acid-fast bacilli, examples of the method for preparing and obtaining a MoAb that selectively binds to LAMs of a wide range of acid-fast bacilli may include a method of selecting an antibody using a complex of LAM and the above obtained antibody that is highly specific to tubercle bacillary LAM, preferably LAM of human tubercle bacillus. In this case, the technique for immunization is not particularly limited and a method known in the art can be appropriately selected to be used. It should be noted that, "a complex" as described herein refers to formation of an antigen-antibody complex of LAM and an antibody that is highly specific to tubercle bacillary LAM, and generation of the complex can be confirmed through analysis with ELISA.

(II-2) Method for Producing a MoAb that Specifically Binds to Acid-Fast Bacillary LAM, Preferably Tubercle Bacillary LAM A MoAb that specifically binds to LAM of acid-fast bacilli, preferably tubercle bacillus, can be produced using a non-human animal (immunized non-human animal) that has been immunized with the above described immunization method.

Examples of such methods may include a method of removing a spleen from an immunized non-human animal as described above, preparing cells (antibody producing cells) for the removed spleen, fusing the cells with myeloma cells in accordance with a hitherto known method using polyethylene-glycol or electrical stimulation to obtain hybridomas, sellecting, from the obtain hybridomas, a hybridomas that produces a MoAb that specifically binds to LAM of acid-fast bacilli, preferably tubercle bacillus, and culturing the hybridoma. In this manner, it is possible to prepare and obtain a MoAb that is highly specific to LAM of acid-fast bacilli, preferably tubercle bacillus, more preferably LAM of human tubercle bacillus. Here, culturing of hybridoma may be conducted intra-abdominally in a non-human animal such as a mouse or a rabbit, or may be conducted in vitro using a dish or the like. In the former method, i.e., culturing hybridoma intra-abdominally in a non-human animal, ascites of the non-human animal is collected after culturing, and a desired MoAb is isolated and purified from the ascites. In the latter method, i.e., culturing hybridoma in vitro, a desired MoAb is isolated and purified from culture liquid medium obtained after culturing. Examples of the method for purifying a monoclonal antibody may include a method of, when the subclass of the antibody is IgG, affinity chromatography using protein A.

Furthermore, the MoAb that specifically binds to LAM of acid-fast bacilli, preferably tubercle bacillus, can also be produced using a phage display method developed in recent years (Non-Patent Literature 6: Winter et al., Annu. Rev. Immunol., 12: 433, 1994). Specifically, a spleen is removed from an immunized non-human animal that is immunized by the above described method, total RNA or mRNA is prepared from the removed spleen, cDNA is prepared using the RNA as template, and genes of single-chain antibodies (scFv: single chain fragment of variable region) encoding variable regions of antibodies are prepared. Here, with regard to the variable regions of antibodies, as long as each of them includes two regions of a heavy chain variable region (VH region) and a light chain variable region (LH region), any peptide linker may be included between the VH region and the LH region. The peptide linker may be, for example, as described in (I), a peptide having a linker sequence formed of an amino acid sequence of about 8 to 30 amino acid residues, and examples of such a linker sequence includes a GS linker sequence.

The genes are cloned in a phagemid vector and introduced in *Escherichia coli* which is then infected with a phage to enable expression of scFv antibodies on phage capsules (preparation of scFv display phage library).

When BCG is used as an immunogen (immunizing antigen) in an immunization method of a non-human animal, it is possible to obtain and produce a monoclonal antibody (scFv antibody) that specifically binds to tubercle bacillary LAM, preferably LAM of human tubercle bacillus, by performing bio-panning with the scFv display phage library expressing scFv antibodies, using BCG that has been used as the immunizing antigen, and subsequently performing biopanning using an antigen plate having a solid-phase of tubercle bacillary LAM, preferably LAM of human tubercle bacillus.

Further, as a method for selecting a MoAb (single-chain antibody) that is highly specific to LAM of mycobacteria, it is possible to obtain and produce a single-chain antibody (scFv antibody) that selectively binds to LAMs of a wide range of acid-fast bacilli regardless of whether it is tubercle bacillus or non-tuberculous acid-fast bacilli, by performing bio-panning with the scFv display phage library expressing scFv antibodies, using an antibody-antigen complex in which LAM is captured by a carrier having an anti-LAM antibody as a solid-phase.

It should be noted that, regarding the preparation of total RNA or mRNA, preparation of cDNA, subcloning into a phagemid, introduction into *Escherichia coli*, infection by a phage, and method for screening (bio-panning) a monoclonal antibody (scFv antibody) that specifically binds to acid-fast bacillary LAM, preferably tubercle bacillary LAM, and more preferably LAM of human tubercle bacillus; methods known in the art can be used, and more specifically, the above described steps may be conducted using later described Examples as a reference.

(III) Method for Detecting Acid-Fast Bacilli, Particularly Tubercle Bacillus, and an Acid-Fast Bacillus (in Particular, Tubercle Bacillus) Detection Tool Used Therein The MoAb of the present invention described above can be used for detecting acid-fast bacilli, preferably tubercle bacillus. In other words, by using the MoAb of the present invention, it is possible to determine whether or not a subject is carrying acid-fast bacilli, particularly tubercle bacillus. In other words, it is possible to diagnose/test whether or not a subject is infected with acid-fast bacilli, particularly tubercle bacillus.

Detection (diagnosis/testing) of acid-fast bacilli, particularly tubercle bacillus, of the present invention can be conducted through the following steps of (1) and (2).

(1) A step of bringing the MoAb of the present invention into contact with a biological sample (test sample) of a subject, and (2) a step of assaying tubercle bacillus that exist in the test sample using, as an index, a binding reaction between the MoAb of the present invention and acid-fast bacilli LAM, particularly tubercle bacillary LAM.

The subject's biological sample (test sample) that is brought into contact with the MoAb of the present invention in the step of (1) may be a biological sample in which acid-fast bacilli, particularly tubercle bacillus, exists, and examples of the biological sample may include sputum, saliva, blood (serum, plasma), lung lavage fluid, gastric juice, urine, feces, skin, and pancreatic juice, etc. The biological sample is preferably sputum, saliva, or blood, and is more preferably sputum or saliva.

Here, the subject that is subjected to the assay is preferably human, however, other than human, animals such as horse, cow, goat, sheep, dog, chicken, mouse, hamster, and rat may also be used as a subject.

The condition at which the MoAb of the present invention and the biological sample are brought into contact with each other is not particularly limited as long as it is a condition at which binding reaction between the MoAb of the present invention and acid-fast bacillary LAM, preferably tubercle bacillary LAM, is not compromised, and a general condition for an immune reaction is used. Examples of a method thereof may include causing the MoAb of the present invention and a biological sample containing acid-fast bacilli, preferably tubercle bacillus, to coexist under a temperature condition of generally 45° C. or lower, preferably about 4 to 40° C., and more preferably about 25 to 40° C.; and leaving or incubating the mixture for about 0.5 to 40 hours, and preferably about 1 to 20 hours. Furthermore, there is also no particular limitation in a solvent used in the binding reaction and pH thereof as long as there is no adverse effect on the reaction; and, in accordance with or conforming to a hitherto known method, a buffer (e.g., citrate buffer, phosphate buffer, tris salt buffer, acetate buffer, etc.,) can be used such that the pH becomes about 5 to 9.

The step of (1) may be conducted in a state in which the MoAb of the present invention is immobilized (solid-phased) (a state in which the MoAb is bound to a solid carrier). Such immobilizing includes both cases of the MoAb of the present invention being bound to the solid carrier in a detachable manner and in an undetachable manner.

As the solid carrier used for immobilizing the MoAb, various carriers commonly used in the art can be used, and examples thereof may include a wide range of articles such as sticks, beads, plates (including microplates), test tubes, and the like formed from various materials such as glass, cellulose powder, Sephadex, Sepharose, polystyrene, filter papers, carboxymethyl cellulose, nitrocellulose, ion-exchange resins, dextran, plastic films, plastic tubes, nylon, glass beads, silk, polyamine-methyl vinyl ether-maleic acid copolymers, amino acid copolymers, ethylene-maleic acid copolymers, etc.

There is no particular limitation in the immobilizing method, and both a physical bond and a chemical bond can be used depending on the various solid carriers. Examples thereof may include: chemical reactions such as a diazo method as a covalent binding method, peptide methods (acid-amide derivative method, carboxyl chloride resin method, carbodiimide resin method, maleic anhydride derivative method, isocyanate derivative method, cyanogen bromide activated polysaccharide method, cellulose carbonate derivative method, and a method using a condensation reagent), alkylation method, carrier binding methods using a cross-linking reagent (e.g., using glutaraldehyde, hexamethylene isocyanate, or the like as a cross-linking reagent), and a carrier binding method using Ugi reaction; ionic bond methods using a carrier such as ion-exchange resins; and physical adsorption methods using, as a carrier, porous glass such as glass beads.

At step (2), the MoAb of the present invention may be used in a labeled state using any labeling substance. Here, examples of the labeling substance may include: enzymes such as horseradish peroxidase (HRP) and alkaline phosphatase; fluorescent substances such as fluorescein isocyanate and rhodamine; radioactive substances such as $^{32}P$ and $^{125}I$; coloring substances (coloration substance) such as latex including natural rubber latex and synthetic latex such as a polystyrene latex colored with metal colloids such as a gold colloid and a white colloid or pigments of red, blue, or the like; and chemiluminescence substances. Labeling of the MoAb with these labeling substances can be conducted in accordance with a hitherto known method depending on the various labeling substances.

The step of (2) is a step of detecting/assaying an immune complex (antigen-antibody bound substance) obtained through a binding reaction between the MoAb of the present invention and LAM of acid-fast bacilli, preferably tubercle bacillus. Here, detecting/assaying the immune complex (antigen-antibody bound substance) and conditions for that is not particularly limited, and a method and conditions identical to or conforming to a common immunoassay method may be used. Specifically, depending on the type of labeling substance used for labeling the MoAb, various methods that are generally used for immunochemical assay can be used, such as, for example, radioisotopic immunoassay (RIA method), ELISA method, fluorescent antibody method, plaque method, spotting method, agglutination method, Ouchterlony method, etc., (e.g., cf. p. 30-53 in "Hybridoma method and monoclonal antibody" published by R&D planning K.K., on Mar. 5, 1982). From a stand point of sensitivity and simplicity, step (2) is conducted in accordance with preferably ELISA method, and more preferably sandwich method.

For example, when a solid-phase sandwich method is used, an assay target which is an acid-fast bacillus, preferably tubercle bacillus, in a test sample can be assayed, for example, in the following manner.

First, a biological sample (e.g., sputum, saliva, or blood etc.,) is added as a test sample containing an assay target which is an acid-fast bacillus, preferably tubercle bacillus, to a solid-phased antibody obtained by immobilizing (including detachable immobilizing) an antibody that causes a specific antigen-antibody reaction with LAM of the assay target acid-fast bacillus, preferably tubercle bacillus, to allow an antigen-antibody reaction to occur. Next, unbound substances are removed by, for example, washing; an antibody that causes a specific antigen-antibody reaction with LAM of the assay target acid-fast bacilli, preferably tubercle bacillus, is added to allow reaction with assay-target bacteria in the antigen-antibody bound substance generated above; and an antigen-antibody bound substance (a complex of "antibody-acid-fast bacillus-antibody", and preferably a complex of "antibody-tubercle bacillus-antibody") generated in the reaction is detected (qualitative measurement) or an amount thereof is measured (quantitative measurement). For this method, in the present invention, the MoAb, preferably MoAb1, of the present invention, is used as the antibody that causes a specific antigen-antibody reaction with LAM of acid-fast bacilli, preferably tubercle bacillus.

Assay of the antigen-antibody bound substance (the complex of "antibody-acid-fast bacillus-antibody" and preferably the complex of "antibody-tubercle bacillus-antibody") can be conducted easily by using an antibody (labeled antibody) that is labeled with any of the labeling substances described above as one of the antibodies (MoAb, preferably MoAb1 of the present invention) used to conduct the antigen-antibody reaction with LAM of acid-fast bacilli, preferably tubercle bacillus. To allow the assay to be conducted more easily, for example, it is possible to use an immunochromatography using an antibody labeled with a colored latex particle or the like such as a gold colloid etc. A person skilled in the art will know well about the selection of various means for these assay techniques and modifications thereof, and the present invention may be realized with any of such techniques (see "Clinical Test Method Manual" Kanehara Shuppan, 1995, etc.).

The method can be conducted using, for example, an acid-fast bacillus detection tool, preferably tubercle bacillus detection tool (hereinafter, also referred to as "detection tool"), having the following structure. The detection tool is a tool for determining existence of acid-fast bacilli, preferably tubercle bacillus, in body fluid (including sputum, saliva, and urine) of human or an animal, i.e., determining presence or absence of infection by acid-fast bacilli, preferably tubercle bacillus; and includes a solution-absorbing piece formed from a material capable of transferring a test sample through capillary action.

The solution-absorbing piece includes:
(i) a sample collection part for absorbing and collecting a test sample;
(ii) a labeled antibody part supporting a labeled anti-tubercle bacillary LAM antibody (MoAb of the present invention) that specifically reacts with LAM of acid-fast bacilli, preferably tubercle bacillus, in the test sample;
(iii) a determination part including a test result display part described in the following,
(a) the test result display part having immobilized thereon a non-labeled anti-tubercle bacillary LAM antibody (MoAb of the present invention) that specifically reacts with LAM of acid-fast bacilli, preferably tubercle bacillus; and
(iv) a solution absorption part for absorbing remaining solution of the test sample that has moved through the sample collection part, the labeled antibody part, and the determination part.

It should be noted that the (iii) determination part includes, in addition to the (a) test result display part, a control display part disposed apart therefrom described in the following:
(b) the control display part having immobilized thereon a non-labeled anti-acid-fast bacillary LAM antibody (MoAb of the present invention), preferably a non-labeled anti-tubercle bacillary LAM antibody (MoAb1 of the present invention), which reacts with a labeled anti-acid-fast bacillary LAM antibody (MoAb of the present invention), preferably a labeled anti-tubercle bacillary LAM antibody (MoAb1 of the present invention).

With the detection tool, it is possible to determine existence of acid-fast bacilli, preferably tubercle bacillus, in the test sample by presence or absence of coloring of (a) the test result display part.

The detection tool of the present invention includes the solution-absorbing piece formed from a material capable of transferring the test sample through capillary action or chromatography action (in the present invention, these are referred to as "capillary action" as a whole). The solution-absorbing piece may be a fragment that is sheet-like (hereinafter, referred to as "a sheet-like fragment"), and the sheet-like fragment may be formed from a single sheet or may be formed from a plurality of layers of sheets stacked or connected with each other. Alternatively, the solution-absorbing piece may take various forms capable of absorbing and transferring liquid through capillary action, such as a long and thin bar shaped fragment or the like. It should be noted that, the detection tool of the present invention may further include a support body for supporting the solution-absorbing piece.

A material for the solution-absorbing piece is not particularly limited as long as: the material has a porous structure or a capillary structure allowing permeation of a solvent (water, serum, urine, and other biological samples), a test component (acid-fast bacilli such as tubercle bacillus), and a complex (e.g., a complex [labeled antibody-tubercle bacillus] of a labeled anti—tubercle bacillary LAM antibody (MoAb1 of the present invention) and tubercle bacillus, or a complex [labeled antibody-tubercle bacillus-antibody] of said complex and a non-labeled anti—tubercle bacillary LAM antibody (MoAb1 of the present invention)) including the test component; and the material allows, when a test sample containing the test component is applied (collected, dropped, added) to (1) the sample collection part, the test sample is transferred (spread) within the porous structure or the capillary structure even when the test sample obtains therein the anti-tubercle bacillary LAM antibody (MoAb1 of the present invention) and the complex (labeled antibody-tubercle bacillus) during the transferring. Examples thereof may include the above described solid carrier. Of those described above, an organic porous body is preferable. It should be noted that, examples of the organic porous body may include natural fibers such as cellulose, cellulose derivatives such as nitrocellulose and semi-synthetic fibers such as cellulose acetate, fiber aggregates formed from synthetic fibers such as polyethylene, polypropylene, nylon, and polyester, porous polypropylene, porous polystyrene, porous polymethyl methacrylate, porous nylon, porous polysulfone, porous fluorine resins, and porous synthetic resins such as polyvinylidene fluoride having introduced therein a hydrophilic group. Natural fibers such as cellulose, and cellulose derivatives such as nitrocellulose and semi-synthetic fibers such as cellulose acetate are preferable.

There is no particular limitation in the size of the solution-absorbing piece; and a preferable size thereof is a width (length of a short side) of about 2 to 20 mm, preferably in a range of about 4 to 10 mm, and a length (length of a long side) of 20 to 200 mm, preferably in a range of 30 to 150 mm.

In the following, the detection tool according to an embodiment of the present invention will be described with reference to the drawings.

(A) and (B) in FIG. 1 show one mode of the detection tool of the present invention. (A) and (B) in FIG. 1 are diagrams viewed from a side of the detection tool of the present invention. In the detection tool, a solution-absorbing piece includes a sample collection part (1) for collecting (adding) a test sample, a labeled antibody part (2), a determination part (3) having a test result display part (a), and a solution absorption part (4) for absorbing remaining solution of the test sample that has moved through the sample collection part, the labeled antibody part, and the determination part. (B) in FIG. 1 shows the detection tool including, at the determination part (3), a control display part (b) in addition to the test result display part (a).

Although, in the example shown in FIG. 1, the solution-absorbing piece is a sheet-like fragment formed from multiple pieces of sheets, the sheet-like fragment may be formed from a single sheet of a uniform material, or may be formed as a single sheet as a whole but from a plurality of sheet pieces of the same or different materials. It should be noted that the whole sheet may be formed from a plurality sheets, or may have a portion that is partially formed from a plurality sheets.

In the example shown in FIG. 1, the sheet-like fragment is adhered on a support body 10. The sheet-like fragment includes, sequentially from one end side to the other end side in the long side direction, a sheet 21 forming the sample collection part (1), a sheet 22 forming the labeled antibody part (2), a sheet 23 forming the determination part (3), and a sheet 24 forming the solution absorption part (4). Furthermore, as shown in FIG. 2, it is possible to have a configuration in which an end portion of the sheet 21 overlaps an end portion of the sheet 22, an end portion of the sheet 22 overlaps an end portion of the sheet 23, and an end portion of the sheet 23 overlaps an end portion of the sheet 24. By having such a configuration, movement of a solution can be made smoothly.

The sample collection part (1) is a part (test sample feed part) for absorbing and collecting a test sample which is an assay target. Examples of the test sample may include a subject's biological sample which is an assay target of the present invention.

As shown in FIG. 1 and FIG. 2, the sample collection part (1) may be positioned at an end portion (leading end) of the sheet-like fragment.

The labeled antibody part (2) is formed in contact with a trailing end of the sample collection part (1) as described above (FIG. 1), or formed in a state of being partially overlapped with the sample collection part (1) (FIG. 2). The labeled antibody part (2) includes, in a detachable manner, an antibody that specifically reacts and binds to acid-fast bacillary LAM, preferably tubercle bacillary LAM, contained in the test sample. Specifically, the detection tool of the present invention includes, at the sheet 22 forming the labeled antibody part (2) in a detachable manner, an anti-acid-fast bacillary LAM antibody (MoAb of the present invention), preferably an anti-tubercle bacillary LAM antibody (MoAb1 of the present invention), which specifically binds to, through an antigen-antibody reaction, acid-fast bacillary LAM, preferably tubercle bacillary LAM. Here, the MoAb of the present invention is used in a state of being labeled with any of the above described labeling substances, i.e., as a labeled anti-acid-fast bacillary LAM antibody (labeled MoAb of the present invention), and the MoAb1 is used as a labeled anti-tubercle bacillary LAM antibody (labeled MoAb1 of the present invention).

Among the materials adopted in the sheet-like fragment, the labeled antibody part (2) is preferably formed from a hydrophilic and water absorbing material that includes the labeled anti-acid-fast bacillary LAM antibody (labeled MoAb of the present invention), preferably the labeled anti-tubercle bacillary LAM antibody (labeled MoAb1 of the present invention), in a detachable manner, which reacts with a test component (acid-fast bacilli, preferably tubercle bacillus) in the test sample that has moved from the sample collection part (1) to form an antigen-antibody complex (a complex of acid-fast bacillary LAM and the labeled anti-acid-fast bacillary LAM antibody (labeled MoAb of the present invention), preferably a complex of tubercle bacillary LAM and the labeled anti-tubercle bacillary LAM antibody (labeled MoAb1 of the present invention)). The material has a property allowing movement of the complex in direction shown with an arrow P in FIG. 1, in association with movement of the test sample to the determination part (3).

It should be noted that there is no limitation in the method for causing the labeled antibody part (2) to support, in a detachable manner, the labeled anti-acid-fast bacillary LAM antibody (labeled MoAb of the present invention), preferably labeled anti-tubercle bacillary LAM antibody (labeled MoAb1 of the present invention); and examples thereof include a method of impregnating the labeled antibody part (2) with a solution containing the labeled MoAb of the present invention, preferably the labeled MoAb1 of the present invention and a method of adhering such a solution to the labeled antibody part (2). Furthermore, for the purpose of allowing the test component (acid-fast bacilli, preferably tubercle bacillus) contained in the test sample to fully bind to the labeled antibody part (2), it is preferable to cause the labeled antibody part (2) to support an excessive amount of the labeled MoAb of the present invention, preferably the labeled MoAb1 of the present invention.

The determination part (3) is a part for further transferring, to the solution absorption part (4), the test sample which has moved from the sample collection part (1) through the labeled antibody part (2). The determination part (3) includes, at a transfer region thereof, a part (the test result display part (a)) for capturing a specific component (a complex of acid-fast bacillary LAM and the labeled antiacid-fast bacillary LAM antibody (labeled MoAb of the present invention), preferably a complex of tubercle bacillary LAM and the labeled anti-tubercle bacillary LAM antibody (labeled MoAb1 of the present invention)) contained in the test sample that has been transferred, and displaying the capture result. Since it is possible to determine existence or non-existence of mycobacteria, preferably tubercle bacillus, based the result displayed on the test result display part (a) in the test sample; the region including the display part (a) is referred to as "the determination part (3)."

In addition to the test result display part (a), the detection tool of the present invention may include the control display part (b) at the determination part (3). It should be noted that the test result display part (a) and the control display part (b) are sequentially arranged with an interval set therebetween.

Immobilized on the test result display part (a) in an excessive amount is a non-labeled antibody (non-labeled anti-acid-fast bacillary LAM antibody) that specifically reacts with acid-fast bacillary LAM, preferably a non-labeled antibody (non-labeled anti-tubercle bacillary LAM antibody) that specifically reacts with tubercle bacillary LAM. Therefore, acid-fast bacilli that have bound with the labeled MoAb of the present invention, preferably tubercle bacillus that has bound with the labeled MoAb1 of the present invention, through an antigen-antibody reaction at the labeled antibody part (2) are captured at the test result display part (a) in a state of a complex with the labeled MoAb of the present invention, preferably the labeled MoAb1 of the present invention; and coloring attributed to the labeling substance appears at an intensity that depends on the captured amount.

It should be noted that, as the anti-acid-fast bacillary LAM antibody forming the non-labeled anti-acid-fast bacillary LAM antibody, the MoAb of the present invention which specifically binds to LAM of acid-fast bacilli (MoAb of the present invention) can be used similarly. Furthermore, as the anti-tubercle bacillary LAM antibody forming the non-labeled anti-tubercle bacillary LAM antibody, the MoAb1 of the present invention which specifically binds to tubercle bacillary LAM (MoAb1 of the present invention) can be used similarly.

Immobilized on the control display part (b) is a predetermined amount of the non-labeled antibody (second antibody) that reacts with the labeled anti-acid-fast bacillary LAM antibody (labeled MoAb of the present invention), preferably the labeled anti-tubercle bacillary LAM antibody (labeled MoAb1 of the present invention), included in the labeled antibody part (2). The control display part (b) may be disposed apart from the test result display part (a) in the movement direction (direction of p in FIG. 1) of the test sample in an order of the test result display part (a) and the control display part (b). Immobilized on the control display part (b) in an excessive amount is the non-labeled antibody (second antibody) that reacts with the labeled anti-acid-fast bacillary LAM antibody (labeled MoAb of the present invention), preferably the anti-tubercle bacillary LAM antibody (labeled MoAb1 of the present invention), contained in the test sample that has moved for the preceding sheet piece.

Therefore, at the control display part (b), the labeled anti-acid-fast bacillary LAM antibody (labeled MoAb of the present invention), preferably the anti-tubercle bacillary LAM antibody (labeled MoAb1 of the present invention), which has been detached from the labeled antibody part (2) and released in the test sample is captured, and coloring attributed to the labeling substance of the labeled anti-acid-fast bacillary LAM antibody (labeled MoAb of the present invention), the anti-tubercle bacillary LAM antibody (labeled MoAb1 of the present invention), appears at an intensity that depends on the amount of the second antibody immobilized on the control display part (b).

Here, the non-labeled antibody (second antibody) is sufficient if it is one that binds to the labeled anti-acid-fast bacillary LAM antibody (labeled MoAb of the present invention), preferably the anti-tubercle bacillary LAM antibody (labeled MoAb1 of the present invention). Although such a non-labeled antibody (second antibody) is not limited, for example, LAM binding protein of acid-fast bacilli, anionic particles, and the like can be used.

Assay of tubercle bacillus using the detection tool of the present invention is performed using, as an index, the presence or absence of coloring at the test result display part (a) of the determination part (3). At this moment, if necessary, it is possible to use, for the determination, presence or absence of coloring at the control display part (b) of the determination part (3). Even when coloring is not recognizable at the test result display part (a), if coloring can be recognized at the control display part (b), the assay has been performed properly and the assay result can be determined as negative. However, when coloring is not recognizable at the control display part (b), it indicates that the assay has not been performed properly, and the result of the test result display part (a) cannot be used to determine as negative.

Among the materials adopted in the sheet-like fragment, the determination part (3) is preferably formed from a hydrophilic and water absorbing material that can move the test sample containing various components to the solution absorption part (4) through capillary action, and has a property of stably immobilizing the non-labeled anti-acid-fast bacillary LAM antibody (labeled MoAb of the present invention), preferably the anti-tubercle bacillary LAM antibody (labeled MoAb1 of the present invention), on the test result display part (a), or immobilizing the non-labeled antibody (second antibody) on the control display part (b).

The solution absorption part (4) is a part for absorbing remaining solution of the test sample that has moved in the direction of arrow P from the sample collection part (1) through the labeled antibody part (2) and the determination part (3) (the test result display part (a), or the test result display part (a) and the control display part (b)). Therefore, among the materials adopted in the sheet-like fragment, the solution absorption part (4) is preferably formed from a hydrophilic and absorbent material, and more preferably a material having a property of not repelling an absorbed solution or an elastic material. Specifically, examples such material may include nonwoven fabrics such as filter papers and hydrophilic fibers, and laminated bodies of filter papers and nonwoven fabrics can also be used.

Although the detection tool of the present invention basically includes the sheet-like fragment having the above described configuration, it is also possible to include the support body 10 in addition to the sheet-like fragment. There is no particular limitation in the support body 10, as long as it has the configuration and material capable of retaining the sheet-like fragment. For example, it may be a sheet like support body laminated on the rear surface (bottom layer surface) of the sheet-like fragment to be used, or a housing-form support body for housing the sheet-like fragment.

Examples of the sheet like support body may include sheets made from various plastics (plastic sheets), hard papers, sheets made from metals (including an alloy) such as aluminum, multi-layered papers obtained by pasting together (adhering together) multiple sheets of, for example, heterogeneous or same quality paper, articles obtained by pasting together (adhering together) a plastic sheet and a paper, articles obtained by pasting together (adhering together) a paper and a metal sheet, articles obtained by pasting together (adhering together) a plastic sheet, a paper, and a metal sheet, and papers having provided thereon coating such water-proofing and the like. Preferably, the support body has a waterproof function.

The housing-form support body is preferably a moisture impermeable material such as polyvinyl chloride, polypropylene, polyethylene, polystyrene, acrylic acid polymers, and the like; but an article made of paper can also be used if a water-repellent treatment is performed thereon. The housing preferably has formed thereon at least "a solution collection window" corresponding to the sample collection part (1) of the sheet-like fragment housed in the housing, "a determination display window" corresponding to the test result display part (a) of the determination part (3), and "a control display window" corresponding to the control display part (b). It should be noted that "the determination display window" and "the control display window" may be formed individually, or may be formed as a single window.

To use the detection tool of the present invention including the sheet-like fragment described above, first, the sample collection part (1) is impregnated with the test sample. By doing so, the test sample absorbed by the sample collection part (1) permeates the sheet-like fragment by capillary action, and first reaches the labeled antibody part (2) supporting, in a detachable manner, the labeled anti-acid-fast bacillary LAM antibody (labeled MoAb of the present invention), preferably the anti-tubercle bacillary LAM antibody (labeled MoAb1 of the present invention). Here, by an antigen-antibody reaction, the test component (tubercle bacillus) in the test sample specifically binds to the labeled anti-acid-fast bacillary LAM antibody (labeled MoAb of the present invention), preferably the anti-tubercle bacillary LAM antibody (labeled MoAb1 of the present invention). Next, the test sample reaches the test result display part (a) of the determination part (3) while being accompanied by "a complex of acid-fast bacilli and the labeled anti-acid-fast bacillary LAM antibody (labeled MoAb of the present invention)" ("a complex of tubercle bacillus and the labeled anti-tubercle bacillary LAM antibody (labeled MoAb1 of the present invention)") and "excessive labeled tubercle bacillary LAM antibody (labeled MoAb of the present invention) that did not bind with tubercle bacillus" ("excessive labeled tubercle bacillary LAM antibody (labeled MoAb1 of the present invention) that did not bind with tubercle bacillus"). Since the non-labeled anti-acid-fast bacillary LAM antibody (MoAb of the present invention) that specifically binds to acid-fast bacilli, preferably the non-labeled anti-tubercle bacillary LAM antibody (MoAb1 of the present invention) that specifically binds to tubercle bacillus, is stably immobilized on the test result display part (a); "the labeled anti-acid-fast bacillary LAM antibody (labeled MoAb of the present invention) that has specifically bound with acid-fast bacilli," preferably "the labeled anti-tubercle bacillary LAM antibody (labeled MoAb1 of the present invention) that has specifically bound with tubercle bacillus," in the test sample is captured and accumulated. As a result, the test result display part (a) exhibits coloring at an intensity that depends on the amount of acid-fast bacilli, preferably tubercle bacilli, contained in the test sample, based a labeling substance in the captured labeled anti-acid-fast bacillary LAM antibody (labeled MoAb of the present invention), preferably in the captured labeled anti-tubercle bacillary LAM antibody (labeled MoAb1 of the present invention). With this, presence or absence and quantitative proportion of acid-fast bacillary, preferably tubercle bacillus, in the test sample can be detected.

Next, the test sample reaches the control display part (b) of the determination part (3) while being accompanied by "excessive labeled anti-acid-fast bacillary LAM antibody (labeled MoAb of the present invention) that did not bind to acid-fast bacilli," preferably "excessive labeled anti-tubercle bacillary LAM antibody (labeled MoAb1 of the present invention) that did not bind with tubercle bacillus." Since the second antibody (non-labeled antibody) that binds to the labeled anti-acid-fast bacillary LAM antibody (labeled MoAb of the present invention), preferably the second antibody (non-labeled antibody) that binds to the labeled anti-tubercle bacillary LAM antibody (labeled MoAb1 of the present invention), is stably immobilized on the control display part (b) at a certain amount; the labeled anti-acid-fast bacillary LAM antibody (labeled MoAb of the present invention), preferably the labeled anti-tubercle bacillary LAM antibody (labeled MoAb1 of the present invention), which is excessively included in the test sample is captured and accumulated. As a result, the control display part (b) exhibits coloring at an intensity that depends on the amount of the second antibody (or the amount of labeled antibody that has bound to the second antibody) immobilized on the control display part (b).

Other than those described above, various modifications can be made to the detection tool of the present invention without departing from the scope of the present invention. To the detection tool of the present invention, it is possible to attach a specification document describing how to use the detection tool and a determining method, and thereby the present invention provides a determination kit which is a set including the specification document and the detection tool.

(IV) Tuberculosis Diagnostic Agent or Diagnostic Kit

The acid-fast bacillus detection method and acid-fast bacillus detection tool described above are used for detecting existence of acid-fast bacilli in a biological sample of a subject. In particular, when the MoAb1 of the present invention is used as the monoclonal antibody, tubercle bacillus can be illustrated as a preferable example of acid-fast bacilli. Thus, the acid-fast bacillus detection method and acid-fast bacillus detection tool described above are used for diagnosing presence or absence of infection with acid-fast bacilli, particularly tubercle bacillus.

Therefore, the MoAb, preferably MoAb1, of the present invention described above is useful as a tuberculosis diagnostic agent, and the present invention provides a tuberculosis diagnostic agent containing the MoAb, preferably MoAb1, of the present invention. The MoAb of the present invention may be detachably or undetachably immobilized on any solid carrier, or may be labeled with any labeling substance.

Furthermore, when the method for detecting acid-fast bacilli, particularly tubercle bacillus, of the present invention is to be conducted, the method can be conducted easily by using a tuberculosis diagnosis kit including, as a tubercle bacillus detection reagent, the MoAb, preferably the MoAb1, of the present invention. Therefore, the present invention provides a tuberculosis diagnosis kit for conducting the tuberculosis detection method. The tuberculosis diagnosis kit is a reagent kit for detection assay of tubercle bacillus existing in a test sample using an antigen-antibody reaction. It is sufficient when the kit includes the MoAb, preferably the MoAb1, of the present invention; and the kit may include the tubercle bacillus detection tool described above, the second antibody that reacts with the MoAb, preferably the MoAb1, of the present invention, an antibody detection reagent, and the like. Furthermore, for convenience of conducting the assay, the diagnostic kit may further include suitable reaction solution, dilution solution, rinsing solution, reaction stop solution, labeled activity measurement reagent, and the like.

(V) Assay for Acid-Fast Bacillary LAM (Particularly Tubercle Bacillary LAM), and Acid-Fast Bacillary LAM (Particularly Tubercle Bacillary LAM) Detection Agent or Detection Kit The MoAb of the present invention is an antibody that specifically recognizes and binds to lipoarabinomannan (LAM) of acid-fast bacilli. Therefore, the acid-fast bacillus detection method of the present invention described above can also be applied for assaying acid-fast bacillary LAM.

Specifically, the assay for acid-fast bacillary LAM of the present invention can be conducted through the following steps:

(1) a step of bringing the MoAb of the present invention into contact with a test sample that may contain acid-fast bacilli; and (2) a step of assaying acid-fast bacillary LAM that exists in the test sample using, as an index, a binding reaction between the MoAb of the present invention and acid-fast bacillary LAM.

These steps of (1) and (2) are steps corresponding respectively to the steps of (1) and (2) set forth in "(III) Method for detecting acid-fast bacilli, particularly tubercle bacillus, and an acid-fast bacillus (in particular, tubercle bacillus) detection tool used therein" described above, and description provided above in (III) can also be used here as reference. In addition, the assay for acid-fast bacillary LAM can be similarly conducted using the acid-fast bacillus detection tool set forth in (III) described above (it should be noted that, in this case, it is possible to rephrase it as "acid-fast bacillary LAM detection tool").

It should be noted that, regarding the MoAb of the present invention, since the MoAb1 is an antibody that specifically recognizes and binds to lipoarabinomannan (LAM) of tubercle bacillus, the acid-fast bacillus detection method of the present invention described above can also be applied as a tubercle bacillus detection method for assaying tubercle bacillary LAM.

Here, the assay for acid-fast bacillary LAM, preferably tubercle bacillary LAM, includes qualitative measurement for detecting acid-fast bacillary LAM, preferably tubercle bacillary LAM, and quantitative measurement for measuring the amount of acid-fast bacillary LAM, preferably tubercle bacillary LAM. Examples of the quantitative measurement may include, but not limited to, a method of creating in advance a standard curve from a reaction between the MoAb of the present invention and a known amount of acid-fast bacillary LAM, preferably tubercle bacillary LAM, and calculating an unidentified amount of acid-fast bacillary LAM, preferably tubercle bacillary LAM, contained in a test sample from the standard curve.

In such an assay, the MoAb of the present invention is useful as an acid-fast bacillary LAM detection reagent, and the present invention provides an acid-fast bacillary LAM detection agent containing the MoAb of the present invention as an acid-fast bacillary LAM detection reagent. In particular, the MoAb1 of the present invention is useful as a tubercle bacillary LAM detection reagent, and the present invention provides a tubercle bacillary LAM detection agent containing the MoAb1 of the present invention as a tubercle bacillary LAM detection reagent. These MoAbs of the present invention may be detachably or undetachably immobilized on any solid carrier, or may be labeled with any labeling substance.

When the acid-fast bacillary LAM assay of the present invention is to be conducted, the assay can be conducted easily by using an acid-fast bacillary LAM detection kit including the MoAb of the present invention as an acid-fast bacillary LAM detection reagent. Furthermore, when the tubercle bacillary LAM assay of the present invention is to be conducted, the assay can be conducted easily by using a tubercle bacillary LAM detection kit including, among the MoAbs of the present invention, the MoAb1 as a tubercle bacillary LAM detection reagent.

Therefore, the present invention provides an acid-fast bacillary LAM detection kit for conducting the acid-fast bacillary LAM assay, particularly a tubercle bacillary LAM detection kit for conducting the tubercle bacillary LAM assay. The acid-fast bacillary LAM detection kit, particularly the tubercle bacillary LAM detection kit, is a reagent kit for detection assay of LAM of acid-fast bacilli, particularly tubercle bacillus, existing in a test sample, using an antigen-antibody reaction. The acid-fast bacillary LAM detection kit includes the MoAb of the present invention. It is sufficient when the tubercle bacillary LAM detection kit includes the MoAb1 of the present invention, and the kit may include the acid-fast bacillary LAM detection tool (or the tubercle bacillary LAM detection tool), a second antibody that reacts with the MoAb (or MoAb1) of the present invention, an antibody detection reagent, and the like. Furthermore, for convenience of conducting the assay, the diagnostic kit may further include suitable reaction solution, dilution solution, washing solution, reaction stop solution, labeled activity measurement reagent, and the like.

(VI) Assay of Sterilized Specimen

The method for detecting acid-fast bacilli or tubercle bacillus of the present invention described above in (III) can be applied as a biohazard-free assay. Specifically, the biohazard-free assay of the present invention can be conducted through the following steps.

(1) Boil-sterilizing, preferably high-pressure-steam sterilizing a specimen sample.

(2) A step of bringing the MoAb, preferably the MoAb1, of the present invention into contact with the sterilized test sample;

(3) a step of assaying tubercle bacillary LAM in the test sample using, as an index, a binding reaction between the MoAb, preferably the MoAb1, of the present invention, and tubercle bacillary LAM; and (4) a step of determining that the test sample is infected with tubercle bacillus when tubercle bacillary LAM has been detected in the test sample.

(VII) Method for Determining Tuberculosis Curative Effect of an Antituberculosis Medicament The method for detecting acid-fast bacilli, particularly tubercle bacillus, of the present invention described above in (III) can be applied for determining tuberculosis curative effect of an antituberculosis medicament.

Specifically, the method for determining tuberculosis curative effect of an antituberculosis medicament of the present invention can be conducted through the following steps.

(1) A step of bringing the MoAb, preferably the MoAb1, of the present invention into contact with both test samples before and after administration of an antituberculosis medicament;

(2) a step of assaying tubercle bacillary LAM in the test samples before and after the administration of the antituberculosis medicament using, as an index, a binding reaction between the MoAb, preferably the MoAb1, of the present invention and tubercle bacillary LAM; and (3) a step of determining that the antituberculosis medicament has tuberculosis curative effect when tubercle bacillary LAM is detected in the test sample before the administration of the antituberculosis medicament and when tubercle bacillary LAM is not detected in the test sample after the administration of the antituberculosis medicament.

These steps of (1) and (2) are steps corresponding respectively to the steps of (1) and (2) set forth in "(III) Method for detecting mycobacteria, particularly tubercle bacillus" described above, and the method described in (III) above can be conducted similarly, except that the test sample is a test sample of a tuberculosis patient who has contracted tuberculosis (infected with tubercle bacillus), and that test samples subjected to the method are a test sample before administration of an antituberculosis medicament (before a tuberculosis therapy) and a test sample after the administration of the antituberculosis medicament (after the tuberculosis therapy). In addition, the assay for tubercle bacillary LAM conducted at (2) can be similarly conducted using the tubercle bacillus detection tool set forth in "(III) Method for detecting acid-fast bacilli, particularly tubercle bacillus" described above (it should be noted that, in this case, it is possible to rephrase it as "tubercle bacillary LAM detection tool").

As the antituberculosis medicament described here, those that are hitherto known in the art can be used, such as rifampicin, isoniazid (isonicotinic acid hydrazide), pyrazinamide, streptomycin and a salt thereof, and ethambutol and a salt thereof. However, the antituberculosis medicament is not limited thereto, and includes approve or unapproved medicaments that exhibit bactericidal action (antituberculosis activity) against tubercle bacilli.

As a result of step (2) described above, when tubercle bacillary LAM, tubercle bacillus in other words, is detected in a test sample before administration of an antituberculosis medicament, and when tubercle bacillary LAM (tubercle bacillus) is not detected in a test sample after the administration of the antituberculosis medicament; the effectiveness of the antituberculosis medicament can be determined since the antituberculosis medicament had tuberculosis curative effect on a subject tuberculosis patient.

On the other hand, as a result of step (2) described above, when tubercle bacillary LAM, tubercle bacillus in other words, is detected in a test sample before administration of an antituberculosis medicament, and when tubercle bacillary LAM (tubercle bacillus) is also detected in a test sample after the administration of the antituberculosis medicament, the amount of the tubercle bacillus detected before and after the administration of the antituberculosis medicament may be compared. Here, when a reduction in the amount of tubercle bacillus before and after the administration of the antituberculosis medicament is seen, it suggests possible tuberculosis curative effect of the antituberculosis medicament on a subject tuberculosis patient, and a therapy option of continuing the use of the antituberculosis medicament can be provided to a medical worker. On the other hand, when a reduction in the amount of tubercle bacillus before and after the administration of the antituberculosis medicament is not seen, it indicates that the antituberculosis medicament does not have tuberculosis curative effect on a subject tuberculosis patient. Therefore, a therapy option of stop using the antituberculosis medicament and switching to another therapy can be provided to a medical worker.

In the method described above, the MoAb, particularly the MoAb1, of the present invention is useful as a tuberculosis curative effect determination reagent of an antituberculosis medicament, and the present invention provides a tuberculosis curative effect determination agent containing the MoAb, particularly the MoAb1, of the present invention as a tuberculosis curative effect determination reagent. The MoAb, particularly the MoAb1, of the present invention may be detachably or undetachably immobilized on any solid carrier, or may be labeled with any labeling substance.

Furthermore, when the determining method of the present invention described above is to be conducted, the method can be conducted easily by using a tuberculosis curative effect determination kit including, as a tuberculosis curative effect determination reagent in an antituberculosis medicament, the MoAb, preferably the MoAb1, of the present invention. Therefore, the present invention provides a tuberculosis curative effect determination kit for conducting the tuberculosis curative effect determination method for an antituberculosis medicament. The tuberculosis curative effect determination kit is a reagent kit for determining therapeutic effect of an antituberculous agent on a tuberculosis patient through detection assay of tubercle bacillary LAM existing in test samples before and after therapy using an antigen-antibody reaction. It is sufficient when the kit includes the MoAb, preferably the MoAb1, of the present invention; and the kit may include the tubercle bacillary LAM detection tool described above, the second antibody that reacts with the MoAb of the present invention, an antibody detection reagent, and the like. Furthermore, for convenience of conducting the assay, the diagnostic kit may further include suitable reaction solution, dilution solution, rinsing solution, reaction stop solution, labeled activity measurement reagent, and the like.

Therapy for active tuberculosis is generally conducted by administration of four or more types of therapeutic agents for six months. When tuberculosis infection is suspected, first, a smear test using Ziehl-Neelsen staining or fluorescence staining is performed. If bacteria exist by a number of 10,000 or more in 1 ml of a sputum specimen, it is considered "smear positive." A sputum-smear-positive patient is particularly important as a source of infection, clinically and in term of public health. Therefore, a smear positive patient requires hospital treatment in a tuberculosis ward. One index of switching to outpatient treatment is to have negative smear test results for three consecutive days. The tubercle bacillary LAM detecting method of the present invention can quantify LAM concentration in a biological sample such as sputum, saliva, and blood. Therefore, by assaying LAM in a biological sample such as sputum, saliva, and blood, it is possible to monitor therapeutic agent effectiveness, and the present invention is also applicable to determination of being infection-negative for a bacteria discharge state.

EXAMPLES

The present invention and effects thereof are described below with reference to Examples. However, the scope of the invention is not limited to these Examples.

Examples 1 to 4

1. Preparation of Materials (1-1) Preparation of Oligo-LAM and Preparation of Immunogen LAM of human tubercle bacillus *M. tuberculosis* (3 mg) (derived from strain Aoyama B, Nacalai Tesque) was dialyzed against a 50 mM acetate buffer (pH 4.5), and adjusted to a concentration of 1 mg/mL. Subsequently, 150 μL of a 200 mM periodic acid aqueous solution was added thereto, and the mixture was stirred at 4° C. for 7 minutes while shielded from light. After stirring, 35 μL of ethylene glycol was added thereto, and the mixture was subjected to gel filtration (0.1 M sodium bicarbonate, pH 8.3) using a small column PD-10 (produced by GE Company), and fractionated into 1 mL portions. The fractionated samples were tested for sugar by a phenol-sulfuric acid method; and the fractions in which sugar was detected were dialyzed against pure water, and then freeze-dried.

The freeze-dried oligo-LAM (3 mg) was dissolved in 0.5 mL of pure water. After 12 μL of 100 mg/mL 1-cyano-4-dimethylaminopyridinium tetrafluoroborate dissolved in acetonitrile was added thereto and the mixture was stirred for about 1 minute, 12 μL of 0.2 M triethylamine was added thereto and the mixture was stirred for 2 minutes. Thereafter, 0.53 mL of 0.6 M adipic acid dihydrazide dissolved in a 0.5 M sodium bicarbonate buffer (pH 8.5) was added thereto and the mixture was stirred at 4° C. for 10 hours, and then dialyzed against pure water for about 1 hour.

To the solution obtained after the dialysis, 300 μg of keyhole limpet hemocyanin (KLH), 30 μL of a 200 mM phosphate buffer (pH 5.0), and 45 μL of 100 mM N-hydroxysulfosuccinimide sodium were added. Subsequently, 65 μL of 1 M ethylene dichloride was further added thereto, and the mixture was stirred at 4° C. for 3 hours or more. Finally, the resulting mixture was dialyzed against a phosphate buffer to obtain oligo-LAM-KLH for an immunogen. The oligo-LAM-KLH was mixed with an adjuvant (Complete or Incomplete Freund's adjuvant, produced by Difco) at a ratio of 1:1 (oligo-LAM-KLH:adjuvant (weight ratio)), and used as an immunogen.

(1-2) Preparation of BCG Vaccine and Immunogen

As the BCG vaccine, a freeze-dried BCG vaccine (authorization number: 20300AMZ00767000) produced by Japan BCG Laboratory was used. For immunization, a mixture of 100 mg (wet weight) of the freeze-dried BCG vaccine and 1 ml of physiological saline was used.

(1-3) Preparation of Killed Bacterial Cells of H37Ra and Immunogen

As the killed bacterial cells of H37Ra, *M. tuberculosis* H37Ra (freeze-dried product) produced by Difco was used. For immunization, a mixture of 100 mg (dry weight) of the freeze-dried killed bacterial cells of H37Ra and 1 ml of physiological saline was used.

(1-4) Preparation of Primers for Producing scFv Fragments

Table 1 shows the names, base sequences, and use of primers employed for preparing single-chain antibodies (scFvs). The following primers were synthesized: four sense primers and one antisense primer as primers for VH region amplification, four sense primers and four antisense primers as primers for VL region amplification, one sense primer and one antisense primer as primers for amplification of a linker (GS linker) that joins a heavy chain variable region fragment and a light chain variable region fragment, and two primers for amplification of restriction enzyme (SfiI, NotI) recognition regions. The amino acid sequences set forth in SEQ ID NOs: 13 to 29 of the sequence listing correspond to the amino acid sequences of the primers listed in Table 1, in order from top to bottom.

TABLE 1

| Name | Sequence | Use | SEQ ID NO. |
|---|---|---|---|
| RabVH-F1 | 5'-gccggccgcccagtcggtggaggagtccRgg-3' | VH region sense primer | SEQ ID NO: 13 |
| RabVH-F2 | 5'-gccggccgcccagtcggtgaaggagtccgag-3' | VH region sense primer | SEQ ID NO: 14 |
| RabVH-F3 | 5'-gccggccgcccagtcgYtggaggagtccggg-3' | VH region sense primer | SEQ ID NO: 15 |
| RabVH-F4 | 5'-gccggccgcccagSagcagctgRtggagtccgg-3' | VH region sense primer | SEQ ID NO: 16 |
| RabVH-R | 5'-cctccacctgaggatgaRgagaYggtgaccagggtgcc-3' | VH region antisense primer | SEQ ID NO: 17 |
| RabVκ-F1 | 5'-gcggatcggagctcgtgMtgacccagactcca-3' | VL region sense primer | SEQ ID NO: 18 |
| RabVκ-F2 | 5'-gcggatcggagctcgatMtgacccagactcca-3' | VL region sense primer | SEQ ID NO: 19 |
| RabVκ-F3 | 5'-gcggatcggagctcgtgatgacccagactgaa-3' | VL region sense primer | SEQ ID NO: 20 |
| RabVκ-R1 | 5'-acctgcggccgcttaggatctccagctcggtccc-3' | VL region antisense primer | SEQ ID NO: 21 |
| RabVκ-R2 | 5'-acctgcggccgcttttgatttccacattggtgcc-3' | VL region antisense primer | SEQ ID NO: 22 |
| RabVκ-R3 | 5'-acctgcggccgcttttgacSaccacctcggtccc-3' | VL region antisense primer | SEQ ID NO: 23 |
| RabVλ-F | 5'-gcggatcggagctcgtgctgactcagtcgccctc-3' | VL region sense primer | SEQ ID NO: 24 |
| RabVλ-R | 5'-acctgcggccgcgcctgtgacggtcagctgggtccc-3' | VL region antisense primer | SEQ ID NO: 25 |
| RS1 | 5'-tcatcctcaggtggaggcggttcaggcggaggtggct ctggcggtggcggatcggagctcg-3' | GS linker sense primer | SEQ ID NO: 26 |

TABLE 1-continued

| Name | Sequence | Use | SEQ ID NO. |
|---|---|---|---|
| RS2 | 5'-cgagctccgatccgccaccgccagagccacctccgcct gaaccgcctccacctgaggatga-3' | GS linker antisense primer | SEQ ID NO: 27 |
| RS-Sfi | 5'-agcggcccag ccggccgccc ag-3' | Sfi-I site primer | SEQ ID NO: 28 |
| RS-Not | 5'-acctgcggccgc-3' | Not-I site primer | SEQ ID NO: 29 |

(1-5) Preparation of scFv Phage Library

A rabbit was immunized using BCG vaccine or killed bacterial cells of H37Ra as an immunogen (see (1-2) and (1-3) above, and Reference Example 1 (2)). After completion of the immunization, the spleen of the rabbit was harvested, the tissue was dissolved in an RPMI (serum-free) medium, total RNA was extracted, and cDNA was synthesized from the obtained total RNA. Total RNA was extracted using an RNA extraction kit (Qiagen) in accordance with the operating manual. cDNA was synthesized from total RNA using a cDNA synthesis kit (Invitrogen) in accordance with the operating manual.

The synthesized cDNA was used as a template, and VH gene fragment amplification and VL gene fragment amplification were performed using the specific primers described in Table 1 above. Specifically, the VH gene fragment amplification was conducted using four primer sets: RabVH-F1 and RabVH-R, RabVH-F2 and RabVH-R, RabVH-F3 and RabVH-R, and RabVH-F4 and RabVH-R. The VL gene fragment amplification was conducted using 10 primer sets: RabVκ-F1 and RabVκ-R1, RabVκ-F1 and RabVκ-R2, RabVκ-F1 and RabVκ-R3, RabVκ-F2 and RabVκ-R1, RabVκ-F2 and RabVκ-R2, RabVκ-F2 and RabVκ-R3, RabVκ-F3 and RabVκ-R1, RabVκ-F3 and RabVκ-R2, RabVκ-F3 and RabVκ-R3, and RabVλ-F and RabVλ-R. The obtained gene amplification products were separated by 1.5% agarose gel electrophoresis. Gene amplification products of desired molecular weight were extracted from the gel, and purified.

The purified VH gene amplification product and VL gene amplification product were joined using a GS linker (GGGGSGGGGSGGGGS: SEQ ID NO: 11). RS1 having sequence homologous to the 3' end of the VH gene amplification product was mixed with the VH gene and PCR was performed for 5 cycles to add the GS linker to the 3' end of the VH gene amplification product. Likewise, RS2 having sequence homologous to the 5' end of the VL gene amplification product was mixed with the VL gene and PCR was performed for 5 cycles to add the GS linker to the 5' end of the VL gene amplification product. The GS linker-added VH gene amplification product and the linker-added VL gene amplification product were mixed, and PCR was performed for 10 cycles to produce an scFv gene (VH gene/GS linker/VL gene) in which the VH gene and the VL gene were joined via the GS linker. The thus-prepared scFv gene was used as a template, amplified by performing PCR for 30 cycles using primers in which restriction enzyme sequence was added (see "RS-Sfi" and "RS-Not" in Table 1), and finally cleaved with restriction enzymes SfiI and NotI.

The scFv gene treated with the restriction enzymes was then inserted into the SfiI and NotI sites of antibody display phagemid vector pCANTAB5E (produced by GE), and transformed into E. coli JM109 by electroporation. Subsequently, the transformant was cultured overnight at 37° C. in an LB-Amp/Glu agar medium (LB medium containing 150 µg/mL of ampicillin, 1% glucose, and 1.5% agar), and all of the resulting colonies were harvested.

After the transformed E. coli was adjusted in LB medium to have an absorbance at wavelength 600 nm ($OD_{600}$) of 0.2, the transformant was mixed with a helper phage M13K07 (produced by Invitrogen) ($10^{12}$ cfu), then statically cultured for 30 minutes at 37° C.; and further cultured overnight at 37° C. in 1 L of an LB-Amp/Kan liquid medium (LB medium containing 150 µg/mL of ampicillin and 100 µg/mL of kanamycin) to produce an scFv display phage library.

Finally, the scFv display phage library was concentrated in a PEG/NaCl solution and adjusted with PBS to a concentration of about $1 \times 10^{12}$ cfu/mL, and the resulting library was used for biopanning.

(1-6) Preparation of Soluble scFv (Single-Chain Antibody)

A soluble scFv was prepared using E. coli expression vector pET22b(+) (produced by Novagen). The target scFv gene was amplified with sense and antisense primers, thereby adding the restriction enzyme sequence of NotI to the 5' end and the restriction enzyme sequence of NcoI to the 3' end.

The scFv gene treated with NotI and NcoI was inserted into E. coli expression vector pET22b(+), and then transformed into host E. coli Rosetta (Novagen). The transformed E. coli was cultured overnight at 37° C. in an LB-Amp/Glu agar medium, and the colonies were cultured for 8 hours at 25° C. in 2 mL of an LB-Amp liquid medium. The culture (2 ml) was added to 200 ml of an LB-Amp liquid medium, and cultured for 16 hours at 30° C. to secrete a soluble scFv (single-chain antibody) in the culture supernatant.

The purification of the soluble scFv from the culture supernatant was performed by affinity purification using a column packed with Ni Sepharose (Ni column) (produced by GE). A threefold amount of a 100 mM phosphate buffer was added to the culture supernatant, and the mixture was added to an Ni column to allow the soluble scFv to bind. The column was washed with a 100 mM phosphate buffer containing 10 mM imidazole, and then the soluble scFv was eluted with a 100 mM phosphate buffer containing 500 mM imidazole.

The eluate was subsequently dialyzed against a phosphate buffer overnight to remove imidazole, and a soluble scFv (single-chain antibody) was obtained.

(1-7) Biotin Labeling of Antibodies

Biotin labeling of polyclonal antibody (PoAb) and the above-prepared single-chain antibody (scFv) was performed using a Pierce Sulfo-NHS-LC-Biotin labeling kit, according to the recommended kit operating procedure.

2. Assay (2-1) Measurement of Antibody Titer in Blood (ELISA)

Using sera collected from rabbits and mice immunized with each antigen, antibody titer in blood was confirmed by the ELISA described below.

Purified LAM of human tubercle bacillus M. tuberculosis (derived from strain Aoyama B, Nacalai Tesque) and purified LAM of non-tuberculous acid-fast bacilli M. avium (derived from strain serotype B, Nacalai Tesque) were individually adjusted with PBS to a concentration of 100 µl/ml. Each of the LAM solutions was individually added to each well of separate 96-well microplates in an amount of 100 µL/well and allowed to react overnight at 4° C., and then blocking was performed in a phosphate buffer containing 1% skim milk to prepare antigen plates.

The primary reaction was performed by adding 100 µL of rabbit or mouse serum diluted with a reaction buffer (Tris buffer of pH 7.8 containing 1% BSA (fetal bovine albumin), 1% skim milk, 0.14 M NaCl, and 0.1% Tween 20) to each well of the above antigen plates, and allowing the reaction to proceed at 25° C. for 1 hour. Unreacted antibodies were then removed by washing 3 times. The secondary reaction was performed by adding 100 µL of HRP-labeled anti-rabbit IgG (produced by Epitomics) or HRP labeled anti-mouse IgG (produced by Zymed) diluted 5,000-fold with the reaction buffer to the above primary reaction solution, and allowing the reaction to proceed at 25° C. for 1 hour. Unreacted antibodies were then removed by washing 3 times.

A color-development reaction was performed by adding 100 µL of a TMB (3,3',5,5'-Tetramethylbenzidine) solution to the secondary reaction product, and leaving the mixture to stand at room temperature for 10 minutes. After the color development, the reaction was stopped by adding 100 µL of a 1 N sulfuric acid solution. The detection was performed by measuring absorbance at wavelengths of 450-650 nm ($OD_{450-650\ nm}$).

(2-2) Biopanning

Biopanning was performed in four steps, consisting of steps 1 to 4.

In steps 1 to 3, phage clones bound to an immunogen (BCG vaccine or killed bacterial cells of H37Ra) were concentrated. The scFv display phage library (see (1-5) of "1. Preparation of materials") adjusted to a concentration of $1 \times 10^{11}$ cfu/500 µL with a reaction buffer (Tris buffer of pH 7.8 containing 1% BSA, 1% skim milk, 0.14 M NaCl, and 0.1% Tween 20) was mixed with 1 mg of BCG vaccine or killed bacterial cells of H37Ra, and allowed to react at 25° C. for 2 hours. After the reaction, the cells were harvested by centrifugation (at 10,000 rpm for 10 minutes), and the culture supernatant was removed. After PBS was added to the harvested cells and mixed, the cells were harvested again by centrifugation to wash the cells. The washing operation was performed 5 times. Phages bound to the cells were eluted with 500 µL of eluent (0.1 N HCl solution containing 0.1% BSA, and adjusted to have a pH of 2.2 with 1 M glycine solution), and neutralized by addition of 500 µL of a neutralization liquid (1 M Tris buffer, pH 9.1). The neutralized phage pool was infected with E. coli JM109, and cultured at 37° C. in LB-Amp/Glu agar medium overnight; and the colonies were harvested. After the transformed E. coli adjusted in an LB medium to have $OD_{600\ nm}=0.2$ and a helper phage M13K07 (produced by Invitrogen) ($10^{12}$ cfu) were statically cultured at 37° C. for 30 minutes, 100 mL of an LB-Amp/Kan liquid medium was added, and the cells were cultured overnight at 37° C. The phage culture was concentrated in a PEG/NaCl solution, and adjusted to a concentration of about $1 \times 10^{12}$ cfu/mL with a phosphate buffer. Biopanning on the cells was performed 3 times.

In step 4, biopanning was performed using an antigen plate on which purified M. tuberculosis LAM or purified M. avium LAM had been immobilized (purified LAM immobilized microtiter plate). Specifically, the phage pool bound to the cells obtained in step 3 was added to a purified LAM immobilized microtiter plate, and a reaction was allowed to proceed at 25° C. for 2 hours. Subsequently, unreacted phages were removed by washing with the reaction buffer 10 times. Phages bound to the LAM were eluted with 100 µL of eluent and then neutralized by adding 100 µL of a neutralization liquid (1 M Tris buffer, pH 9.1). The neutralized phage pool was infected with E. coli JM109, and then cultured at 37° C. in an LB-Amp/Glu agar medium overnight.

Reference Example 1

Preparation of Antiserum Against LAM (1) To prepare a polyclonal antibody (PoAb) against LAM, rabbits were immunized with oligo-LAM. As oligo-LAM, specifically, oligo-LAM-KLH prepared as an immunogen by the method described in the aforementioned (1-1) of "1. Preparation of materials" was used. The oligo-LAM-KLH was mixed with an adjuvant (Incomplete Freund's adjuvant) at a ratio of 1:1 (oligo-LAM-KLH:adjuvant (weight ratio)), and 100 µg of the mixture was subcutaneously administered to rabbits (two rabbits: Rab-1 and 2). Thereafter, immunization was performed 4 times at 14-day intervals. After completion of the fifth immunization, blood was taken, and antibody titers in blood against LAM of human tubercle bacillus (M. tuberculosis) and LAM of non-tuberculous acid-fast bacilli (M. Avium) were measured according to the ELISA method described in the aforementioned (2-1) of "2. Assay."

As a result of evaluation using an antigen plate on which M. tuberculosis LAM had been immobilized, sufficient increase in antibody titers was confirmed in sera diluted 384,000-fold in the two subcutaneously immunized rabbits (Rab-1 and 2). The antisera of these rabbits (Rab-1 and 2) also exhibited binding reaction to an antigen plate on which M. Avium LAM had been immobilized, and thus it was confirmed that the antisera of the rabbits (Rab-1 and 2) exhibited similar reactivity to both M. tuberculosis LAM and M. Avium LAM. Specifically, the rabbit antisera (polyclonal antibody) prepared using the oligo-LAM (oligo-LAM-KLH) as an immunogen had reactivity to acid-fast bacillary LAM in general, and no specificity toward tubercle bacillary LAM was observed.

(2) Next, a rabbit was immunized using BCG vaccine as an immunogen, and a rabbit was immunized using killed bacterial cells of H37Ra as an immunogen. Each rabbit was subcutaneously immunized 4 times at 14-day intervals in the same manner as above. Specifically, each rabbit was subcutaneously immunized with a total, per immunization, of 1 ml of physiological saline containing 100 mg of BCG vaccine or killed bacterial cells of H37Ra prepared by the method described in the aforementioned (1-2) or (1-3) of "1. Preparation of materials."

Figure 3:
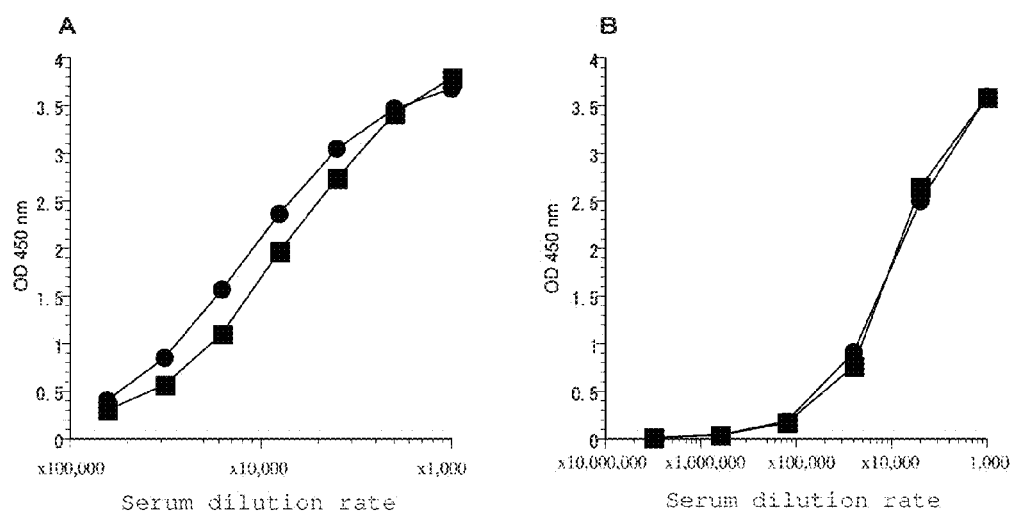

The antibody titer in blood of each rabbit after the second immunization was measured in the same manner as above by the ELISA method described in the aforementioned (2-1) of "2. Assay." Specifically, the antibody titers of sera prepared from the rabbit immunized with the BCG vaccine and the rabbit immunized with the killed bacterial cells of H37Ra were evaluated using an antigen plate on which purified M. tuberculosis LAM had been immobilized, and an antigen plate on which purified M. avium LAM had been immobilized. FIG. 3 (A) shows the results when the BCG vaccine was used as an immunogen, and FIG. 3 (B) shows the results when the killed bacterial cells of H37Ra were used. In the figures, "-■-" indicates reactivity to *M. tuberculosis* LAM, and "-●-" indicates reactivity to *M. avium* LAM.

As shown in FIG. 3, in both the case of using the BCG vaccine and the case of using the killed bacterial cells of H37Ra, it was confirmed that the antibody titers to the LAMs were significantly increased in a concentration-dependent manner. Further, similar reactivity was exhibited to both *M. tuberculosis* LAM and *M. avium* LAM.

As described above, when the oligo-LAM, the BCG vaccine, and the killed bacterial cells of H37Ra were individually used as immunogens, all of the antisera (polyclonal antibodies) against these antigens had reactivity to acid-fast bacillary LAM in general, and no specificity toward tubercle bacillary LAM was observed.

Example 1

Preparation of Single-Chain Antibodies (scFvs) Against LAM (1) Preparation of scFvs Against LAM Single-chain antibodies scFvs were isolated from the spleen cells of the rabbits immunized with the oligo-LAM, the BCG vaccine, and the killed bacterial cells of H37Ra in Reference Example 1.

Specifically, according to the method described in (1-5) of "1. Preparation of materials," total RNA was prepared from the spleen of each rabbit and PCR was performed using cDNA synthesized from the total RNA as a template and using the various primers described in Table 1 to prepare amplification products of VH and VL genes.

Subsequently, scFV genes each having the VH gene and the VL gene joined via a GS linker (GGGGSGGGGSGGGGS: SEQ ID NO: 11) (VH gene/GS linker/VL gene) were prepared, and then scFv display phage libraries were prepared therefrom according to the method described in (1-5) of "1. Preparation of materials." The titer of each library was about $10^6$ cfu, and thus it is presumed that each library had a diversity of $10^6$.

For the scFv display phage library prepared from the spleen cells of the rabbit immunized with the BCG vaccine, biopanning using the BCG vaccine as an antigen (see (2-2) of "2. Assay") was performed 3 times and then the forth biopanning was performed using a microplate on which *M. tuberculosis* LAM had been immobilized.

Similarly, for the scFv display phage library prepared from the spleen cells of the rabbit immunized with the killed bacterial cells of H37Ra, biopanning using the killed bacterial cells of H37Ra as an antigen was performed 3 times, and then the forth biopanning was performed using a microplate on which *M. tuberculosis* LAM had been immobilized.

Ultimately, 200 clones were randomly selected from each panning pool obtained, and LAM reactive clones were screened. As a result, about 10 LAM reactive clones were obtained from each library.

As a result of the base sequence analysis, it was confirmed that the base sequences of the clones obtained from each library were nearly identical.

Through the above-mentioned operations, a single clone of scFv (single-chain antibody) was successfully isolated from each of the scFv display phage library prepared from the spleen cells of the rabbit immunized with the BCG vaccine, and the scFv display phage library prepared from the spleen cells of the rabbit immunized with the killed bacterial cells of H37Ra.

FIG. 4 shows the amino acid sequence of the single-chain antibody scFv (Myco-scFv) prepared from the spleen cells of the rabbit immunized with the killed bacterial cells of H37Ra (SEQ ID NO: 30) and the amino acid sequence of the single-chain antibody scFv (TB-scFv) prepared from the spleen cells of the rabbit immunized with the BCG vaccine (SEQ ID NO: 12) together with the positions of CDR1, CDR2, and CDR3 regions of the heavy chain variable region; GS linker; and CDR1, CDR2, and CDR3 regions of the light chain variable region.

(2) LAM Reactivity of scFv

Reactivity to LAM was evaluated in the single-chain antibody scFv (TB-scFv) obtained from the scFv display phage library prepared from the spleen cells of the rabbit immunized with the BCG vaccine, and the single-chain antibody scFv (Myco-scFv) obtained from the scFv display phage library prepared from the spleen cells of the rabbit immunized with the killed bacterial cells of H37Ra.

Specifically, each of the single-chain antibodies scFvs (TB-scFv and Myco-scFv) was solubilized according to the method described in (1-6) of "1. Preparation of materials" to prepare a soluble scFv. The soluble scFv was then biotin-labeled according to the method described in (1-7) of the same; and reactivity to antigen plates (purified LAM immobilized microtiter plates), i.e., a plate on which purified *M. tuberculosis* LAM had been immobilized and a plate on which purified *M. avium* LAM had been immobilized, was evaluated by the ELISA method described in (2-1) of "2. Assay."

Figure 5:
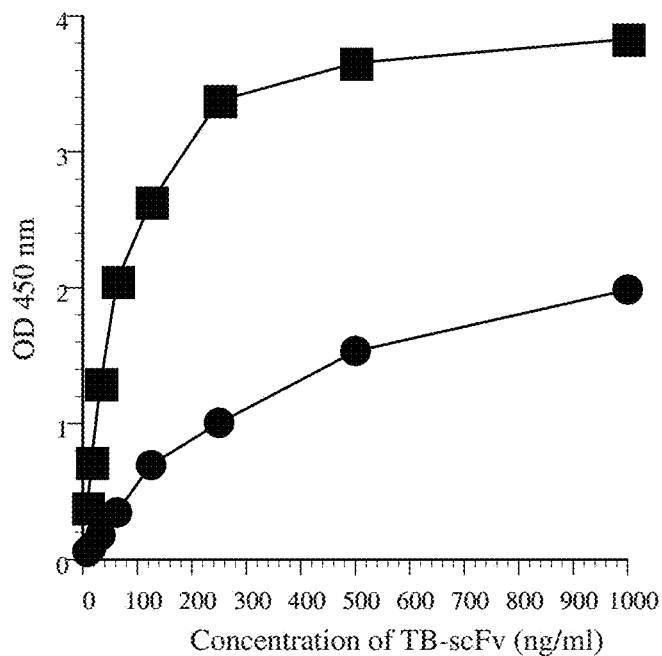

FIG. 5 shows reactivity of single-chain antibody TB-scFv to *M. tuberculosis* LAM (-■-) and to *M. avium* LAM (-●-). As shown in FIG. 5, the results obtained by reacting TB-scFv at concentrations of 1000 ng/ml, 500 ng/ml, 250 ng/ml, 125 ng/ml, 62.5 ng/ml, 31.25 ng/ml, 15.625 ng/ml, and 7.8125 ng/ml with *M. tuberculosis* LAM and *M. avium* LAM in the LAM immobilized antigen plates confirmed that reactivity of TB-scFv to *M. tuberculosis* LAM (-■-) reached a maximum value at a concentration of 250 ng/ml with an OD value (450 nm) of more than 3, whereas reactivity of TB-scFv to *M. avium* LAM (-●-) did not reach a maximum value even at a concentration of 1000 ng/ml with an OD value (450 nm) of about 2. Although the results are not shown, Myco-scFv exhibited almost the same reactivity to both *M. tuberculosis* LAM and *M. avium* LAM.

From the above results, it was confirmed that the single-chain antibody TB-scFv prepared by using the BCG vaccine as an immunogen is a specific antibody having reactivity to LAM of human tubercle bacillus *M. tuberculosis* stronger than to LAM of non-tuberculous acid-fast bacilli *M. avium*.

Example 2

Construction of LAM Detection ELISA

The characteristics of the three types of antibodies prepared in Reference Example 1 and Example 1 (oligo-LAM-immunized rabbit polyclonal antibody (hereinafter referred to as "Myco-Poly") (Reference Example 1), and H37Ra killed bacterial cell-immunized rabbit monoclonal antibody (Myco-scFv) and BCG vaccine-immunized rabbit monoclonal antibody (TB-scFv) (Example 1)) were summarized in Table 2.

TABLE 2

| Name | Immunogen | Remarks |
| --- | --- | --- |
| Myco-scFv | Killed bacterial cells of H37Ra | Rabbit monoclonal antibody (scFv) React to acid-fast bacillary LAM in general |
| Myco-Poly | Oligo-LAM (KLH) | Rabbit polyclonal antibody React to acid-fast bacillary LAM in general |
| TB-scFv | BCG vaccine | Rabbit monoclonal antibody (scFv) High affinity to tubercle bacillary LAM |

Based on the reaction specificity of these antibodies, the antibodies were combined to construct two types of ELISA: acid-fast bacillary LAM detection ELISA, and tubercle bacillary LAM detection ELISA.

(1) Preparation of Acid-Fast Bacillary LAM Detection ELISA

For the construction of acid-fast bacillary LAM detection ELISA, Myco-Poly was immobilized as a capture antibody on a plate, and Myco-scFv was biotin-labeled and used as a detection antibody.

Myco-Poly was adjusted to a concentration of 10 µg/ml with a phosphate buffer. Myco-Poly was added to a 96-well microplate in an amount of 100 µL/well, and allowed to react overnight at 4° C.; afterward, blocking was conducted in a phosphate buffer containing 1% skim milk to prepare an antibody plate.

The primary reaction was performed as follows. A test sample that may contain acid-fast bacilli was used, and 100 µL of the test sample diluted with a reaction buffer (Tris buffer of pH 7.8 containing 1% BSA, 1% skim milk, 0.14 M NaCl, and 0.1% Tween 20) was added to each well of the above antibody plate. The reaction was allowed to proceed at 25° C. for 1 hour, and the plate was then washed 3 times. The secondary reaction was performed by adding 100 µL of biotin-labeled-anti Myco-scFv diluted 5,000-fold with the reaction buffer to each well of the antibody plate, allowing the reaction to proceed at 25° C. for 1 hour, and removing unreacted antibodies by washing 3 times. The tertiary reaction was performed by adding 100 µL of avidin-labeled HRP (produced by Millipore) diluted 10,000-fold with the reaction buffer thereto, allowing the reaction to proceed at 25° C. for 1 hour, and then removing unreacted avidin-labeled HRP by washing 3 times.

A color-development reaction was performed by adding 100 µL of a TMB solution to each well, and leaving the mixture to stand at room temperature for 10 minutes. After the color development, the reaction was stopped by adding 100 µL of a 1 N sulfuric acid solution. The intensity of the color development was detected by measuring absorbance at wavelengths of 450-650 nm.

(2) Preparation of Tubercle Bacillary LAM Detection ELISA

Tubercle bacillary LAM detection ELISA was constructed using TB-scFv as both a capture antibody and a detection antibody. The tubercle bacillary LAM detection ELISA was prepared in the same manner as in the above (1), except that TB-scFv was used as the capture antibody and the detection antibody.

(3) Evaluation of Each LAM Detection ELISA

The acid-fast bacillary LAM detection ELISA and the tubercle bacillary LAM detection ELISA prepared in (1) and (2), respectively, were evaluated for reactivity to LAM, using purified LAM of human tubercle bacillus (*M. tuberculosis*) and purified LAM of acid-fast bacilli (*M. avium*).

Figure 6:
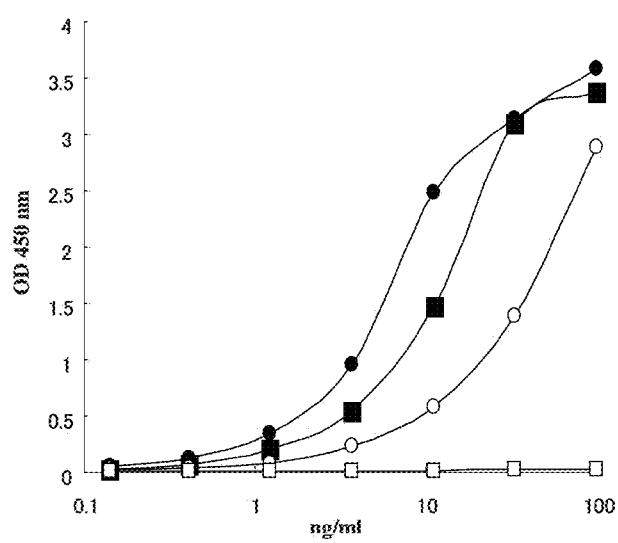

FIG. 6 shows the results. In the figure, ● indicates reactivity to *M. tuberculosis* LAM in the acid-fast bacillary LAM detection ELISA, ■ indicates reactivity to *M. avium* in the acid-fast bacillary LAM detection ELISA, ○ indicates reactivity to *M. tuberculosis* LAM in the tubercle bacillary LAM detection ELISA, and □ indicates reactivity to *M. avium* LAM in the tubercle bacillary LAM detection ELISA.

As is clear from FIG. 6, it was possible to detect *M. tuberculosis* LAM (-■-) and *M. avium* LAM (-●-) equivalently in the acid-fast bacillary LAM detection ELISA. On the other hand, in the tubercle bacillary LAM detection ELISA, it was confirmed that reactivity to tubercle bacillus *M. tuberculosis* LAM almost reached a maximum value at a concentration of 100 ng/ml with an OD value (450 nm) of 3 or more, whereas almost no reactivity to acid-fast bacilli *M. avium* LAM was exhibited even at a concentration of 100 ng/ml.

Example 3

Evaluation of Antibody Reactivity to Acid-Fast Bacillary LAM and Tubercle Bacillary LAM in Acid-Fast Bacillary LAM Detection ELISA and Tubercle Bacillary LAM Detection ELISA (Use of Acid-Fast Bacillary Clinical Isolates)

Figure 7:
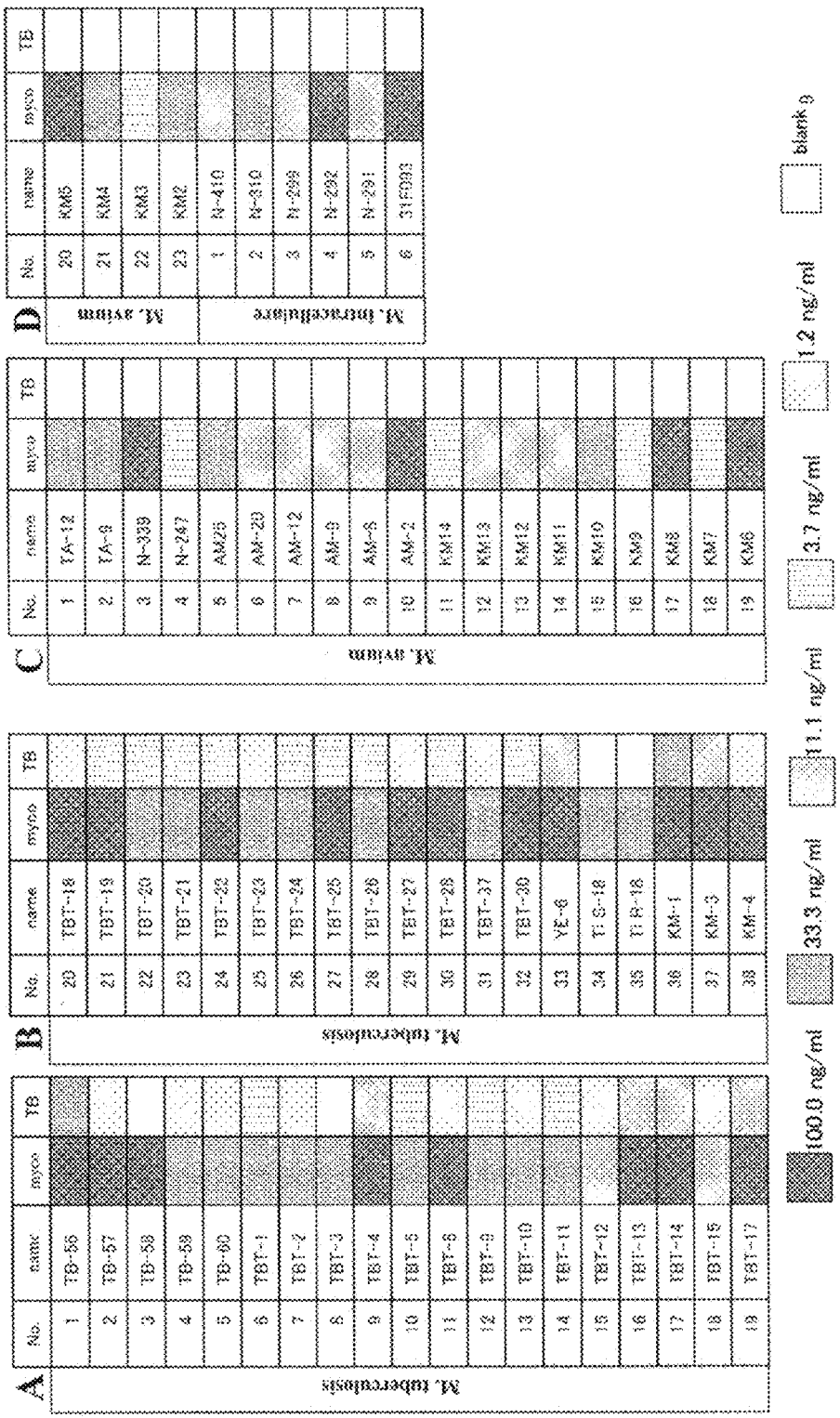

The acid-fast bacillary LAM detection ELISA and the tubercle bacillary LAM detection ELISA constructed in Example 2 were used, and antibody reactivity to acid-fast bacillary LAM and tubercle bacillary LAM was evaluated using the various acid-fast bacillary clinical isolates shown in FIG. 7.

Specifically, as the acid-fast bacillary clinical isolates, cultures of 38 strains of *M. tuberculosis* (see Tables A and B of FIG. 7), cultures of 23 strains of *M. avium* and cultures of 6 strains of *M. intracellulare* (see Tables C and D of FIG. 7) were used. The *M. avium* strains and the *M. intracellulare* strains are pathogenic bacteria of MAC disease. Each acid-fast bacillary clinical isolate was cultured to confluence at 37° C. in a liquid medium (7H9 Broth produced by BD, containing 10% ADC Enrichment produced by BD), and the culture was freeze-preserved at −80° C.

The freeze-preserved culture was thawed and then mixed with an equivalent amount of Y-PER (protein extraction reagent produced by Thermo), and the mixture was subsequently heated for 10 minutes at 95° C. After the cells were harvested by centrifugation (10,000 rpm, 10 minutes), the supernatant was collected. To the collected supernatant, a 4-fold amount of a reaction buffer (phosphate buffer containing 1% skim milk, 0.5% BSA, 0.05% Tween 20, and 0.1% XL-II) was added, 100 µl of the mixture was subjected to the acid-fast bacillary LAM detection ELISA and the tubercle bacillary LAM detection ELISA constructed in Example 2, and antibody reactivity to LAM was measured.

The measurement results obtained through each ELISA were evaluated by comparison with antibody reactivity to purified *M. tuberculosis* LAM used as a standard. FIG. 7 shows the results.

As shown in FIG. 7, in the acid-fast bacillary LAM detection ELISA (see the "myco" columns in each table of FIG. 7), reactivity was exhibited to all of the 38 strains of *M. tuberculosis*, the 23 strains of *M. avium*, and the 6 strains of *M. intracellulare*. On the other hand, in the tubercle bacillary LAM detection ELISA (see the "TB" columns in each table of FIG. 7), reactivity to 34 of the 38 strains of *M. tubercu-*

*losis* was exhibited at a high rate, but no reactivity to the 23 strains of *M. avium* and the 6 strains of *M. intracellulare* was exhibited.

As shown in the above, it was revealed that the acid-fast bacillary LAM detection ELISA constructed in Example 2 had high reactivity to acid-fast bacillary LAM, and was capable of widely detecting acid-fast bacillary LAM. On the other hand, in the tubercle bacillary LAM detection ELISA constructed in Example 2, there was a difference in reactivity among the strains, and the reaction was specific compared to the acid-fast bacillary LAM detection ELISA. Specifically, the tubercle bacillary LAM detection ELISA constructed in Example 2 specifically detected tubercle bacillary LAM, and exhibited good results with a sensitivity of 90% and a specificity of 100%.

From the above results, it was confirmed that the acid-fast bacillary LAM detection ELISA constructed in Example 2 (capture antibody: Myco-Poly and detection antibody: Myco-scFv) can widely detect acid-fast bacillary LAM, and that the tubercle bacillary LAM detection ELISA constructed in Example 2 (capture antibody: TB-scFv and detection antibody: TB-scFv) can specifically detect tubercle bacillary LAM distinctively from non-tuberculous acid-fast bacillary LAM.

Example 4

Construction of LAM Detection Immunochromatography Methods

Immunochromatographic tests for acid-fast bacillary LAM detection and for tubercle bacillary LAM detection were constructed using pairs of antibodies evaluated by ELISA.

(1) Immunochromatography Method for Detecting Acid-Fast Bacillary LAM

To construct an immunochromatographic test for acid-fast bacillary LAM detection, Myco-Poly immobilized on a nitrocellulose membrane was used as a capture antibody, and Myco-scFv labeled with gold colloid was used as a detection antibody.

Myco-Poly (capture antibody) was applied to a nitrocellulose membrane (produced by Millipore, capillary flow time: 240) to a concentration of 3.0 mg/mL (phosphate buffer) and dried at 50° C. for 20 hours. An immunochromatographic strip comprising a nitrocellulose substrate and an absorption pad adhered thereon was prepared. A laminate seal was attached thereto and the resulting strip was cut into a strip 4 mm in width, and used for one test.

To prepare gold colloid-labeled Myco-scFv, gold colloid with a size of 40 nm was used. Myco-scFv was added to gold colloid (OD=1) to a concentration of 2.0 μg/mL and allowed to react at room temperature for 20 minutes. As a buffer for antibody binding, 2 mM TES (N-Tris(hydroxymethyl)methyl-2-aminoethanesulfonic acid) (pH 7.5) was used. After gold colloid labeling, blocking was performed by allowing a reaction to proceed in a buffer containing 2 mM Borax (sodium tetraborate decahydrate) and 1.5% BSA (pH 9.0) at 300 rpm at room temperature for 5 minutes. After blocking, centrifugation was performed at 4620×g for 20 minutes at 4° C., and a culture supernatant was removed. The resulting precipitate was suspended in a gold colloid-labeled antibody dilution solution (10 mM Borax, 5% sucrose, and 1% BSA (pH 9.0)), and then filtered through a 0.1-μm filter.

The assay was performed in the following manner. After a test sample that may contain acid-fast bacilli was diluted with an extraction buffer (72 mM sodium dihydrogen phosphate dihydrate, 4.5% bovine serum albumin, 0.9% casein, 0.09% Triton X-305, 0.1% sodium azide, 10.0% Y-PER, a suitable amount of sodium hydroxide, and a suitable amount of hydrochloric acid, pH 7.0), a suitable amount of gold colloid-labeled antibody solution was added. The strip prepared above was dipped into this liquid to develop the test sample. Seven minutes after the start of the development, the strip was removed and washed with a phosphate buffer containing a surfactant (0.1% Tween 20) for 8 minutes, after which evaluation was performed with the naked eye to determine whether the sample was positive or negative.

(2) Immunochromatography Method for Detecting Tubercle Bacillary LAM

An immunochromatographic test for bacillary LAM detection was constructed in the same manner as in the construction method and assay method described above in (1), except that TB-scFv was used as both the capture antibody and the detection antibody.

(3) Evaluation of Each Immunochromatography Method for Detecting LAM

The reactivity against LAM of the immunochromatographic tests for acid-fast bacillary LAM detection and for tubercle bacillary LAM detection constructed in (1) and (2) was evaluated using purified *M. tuberculosis* LAM and *M. avium* LAM.

Figure 8:
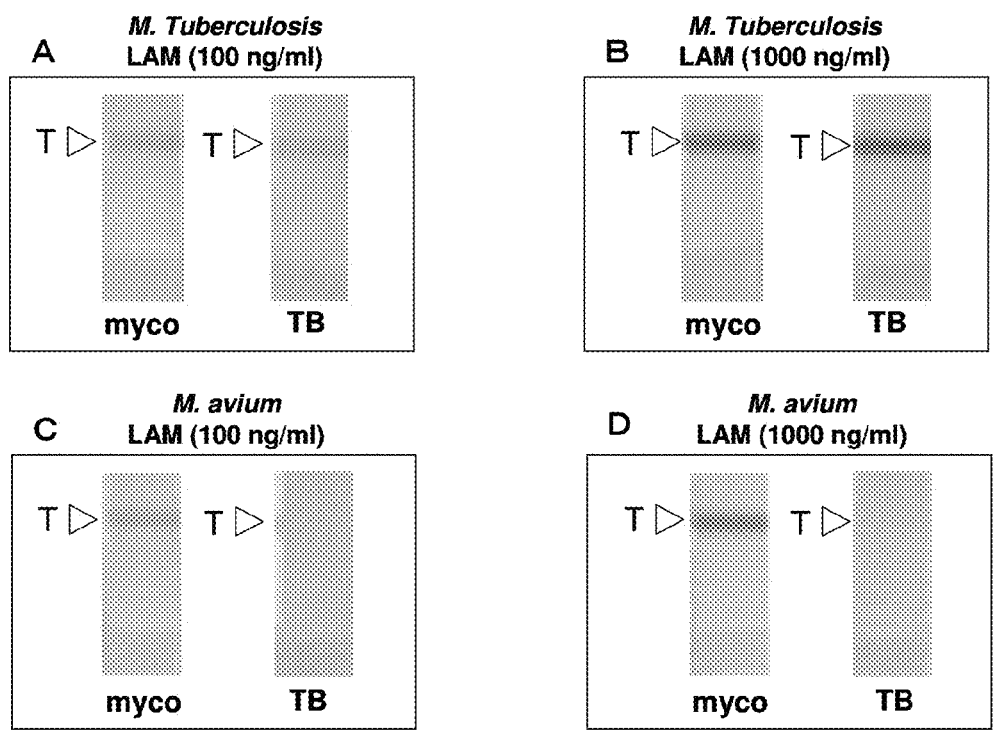

FIG. 8 shows the results.

*M. tuberculosis* LAM was measured by immunochromatography methods for detecting acid-fast bacillary LAM and for detecting tubercle bacillary LAM. A line was confirmed with the naked eye in both of the immunochromatography tests (myco: for acid-fast bacillary LAM detection; and TB: for tubercle bacillary LAM detection) (FIGS. 8A and 8B). Similarly, *M. avium* LAM was measured using both of the assay systems. As shown in FIGS. 8C and 8D, in the immunochromatography test for acid-fast bacillary LAM detection, a line comparable to that observed in the assay of *M. tuberculosis* LAM was confirmed with the naked eye. In contrast, no line was detected, even at a concentration as high as 1000 ng/ml, in the immunochromatography test for tubercle bacillary LAM detection (TB) (FIG. 8D).

The above results indicate that the single-chain antibody TB-scFv prepared using BCG vaccine as an immunogen can specifically detect human tubercle bacillus (*M. tuberculosis*) in immunochromatography tests.

As shown in Examples 1 to 4, the present inventors have successfully isolated a single-chain antibody (scFv (TB-scFv)) that specifically reacts with tubercle bacillary LAM, and established an immunoassay system that can specifically detect tubercle bacillary LAM by measuring LAM with TB-scFv. The assay system using TB-scFv is applicable to ELISA and immunochromatographic tests, and enables quick and easy diagnosis of tuberculosis infection.

Examples 5 to 12

3. Preparation of Materials (3-1) Preparation of BCG Vaccine and Immunogen

A freeze-dried BCG vaccine (authorization number: 20300AMZ00767000) produced by Japan BCG Laboratory was used as a BCG vaccine. For immunization, a mixture of 100 mg (wet weight) of the freeze-dried BCG vaccine and 1 ml of physiological saline was used.

(3-2) Preparation of Chicken scFv Phage Library

A chicken was immunized with BCG vaccine as an immunogen (see (3-1) above and Example 6). After completion of the immunization, the spleen was excised from the chicken, and the tissue was dissolved in an RPMI (serum-free) medium. Total RNA was extracted using an RNA extraction kit (produced by Qiagen) in accordance with the operating manual. cDNA was synthesized from total RNA using a cDNA synthesis kit (produced by Invitrogen) in accordance with the operating manual.

VH and VL gene fragments were amplified using the synthesized cDNA as a template and using the primers listed in Table 3. Specifically, the VH gene fragment was amplified with a primer set of SfiI-CκVH F and GSL-CκVH R, while the VL gene fragment was amplified with a primer set of GSL-CκVL F and NotI-CκVL R.

Kan liquid medium (LB medium containing 150 μg/mL of ampicillin and 100 μg/mL of kanamycin) to produce a chicken scFv display phage library.

Finally, the scFv display phage library was concentrated in a PEG/NaCl solution and adjusted to a concentration of about $1\times10^{12}$ cfu/mL with PBS, and the resulting library was used for biopanning.

(3-3) Antigen Biopanning Using the Chicken scFv Library

Antigen biopanning was performed in four steps, consisting of steps 1 to 4.

In steps 1 to 3, phage clones bound to an immunogen (BCG vaccine) were concentrated. The chicken scFv display

TABLE 3

| Name | Sequence | Use | SEQ ID NO. |
|---|---|---|---|
| Sfi1-C$_K$VH F | 5'-ctatgcggcccagccggccgccgtgacgttggacgag-3' | VH region sense primer with Sfi I site (underlined) | SEQ ID NO: 41 |
| GSL-C$_K$VH R | 5'-cctccaccggaggagacgatgacttcggtcc-3' | VH region anti sense primer | SEQ ID NO: 42 |
| GSL-C$_K$VL F | 5'-gcggatcggccctgactcagccgtcctcggtgtc-3' | VL region sense primer | SEQ ID NO: 43 |
| Not1-CkVL R | 5'acctgcggccgctaggacggtcagg-3' | VL region anti sense primer with Not I site (underlined) | SEQ ID NO: 44 |
| CkVH-GSL-VLF | 5'-tcctccggtggaggcggttcaggcggagatggctctggcggtggcggatcggccctg-3' | GS linker sense primer | SEQ ID NO: 45 |
| CkVL-GSL-VH R | 5'-cagggccgatccgccaccgccagagccatctccgcctgaaccgcctccaccggagg-3' | GS linker anti sense primer | SEQ ID NO: 46 |

The obtained gene amplification products were separated by 1.5% agarose gel electrophoresis. Gene amplification products of desired molecular weight were extracted from the gel, and purified.

The purified VH gene product and the purified VL gene product were joined via a GS linker (SEQ ID NO: 40). CκVL-GSL-VH R (SEQ ID NO: 46) having a sequence homologous to the 3' end of the VH gene product was mixed with the VH gene, and PCR was performed for 5 cycles to add the GS linker to the 3' end of the VH gene. Likewise, CκVH-GSL-VL F (SEQ ID NO: 45) having a sequence homologous to the 5' end of the VL gene product was mixed with the VL gene, and PCR was performed for 5 cycles to add the GS linker to the 5' end of the VL gene. The GS linker-added VH gene and the GS linker-added VL gene were mixed, and PCR was performed for 10 cycles to produce a scFv gene (chicken scFv gene) having the VH gene, GS linker gene, and VL gene joined together. Finally, the scFv gene was cleaved with restriction enzymes, SfiI and NotI.

Subsequently, the scFv gene treated with the restriction enzymes was inserted into SfiI and NotI sites of an antibody display phagemid vector pCANTAB5E, and transformed into E. coli JM109 by electroporation. The transformant was cultured overnight at 37° C. in LB-Amp/Glu agar medium (LB medium containing 150 μg/mL ampicillin, 1% glucose, and 1.5% agar), and all of the generated colonies were collected.

After the transformed E. coli was prepared in LB medium to have an absorbance at 600 nm (OD$_{600\ nm}$) of 0.2, the transformant was mixed with a helper phage M13K07 ($10^{12}$ cfu), then statically cultured at 37° C. for 30 minutes, and further cultured overnight at 37° C. in 1 L of an LB-Amp/ phage library adjusted to a concentration of $1\times10^{11}$ cfu/500 μL with a reaction buffer (Tris buffer of pH 7.8 containing 1% BSA, 1% skim milk, 0.14 M NaCl, and 0.1% Tween 20) (see (3-2) of "3. Preparation of materials") was mixed with 1 mg of BCG vaccine, and allowed to react at 25° C. for 2 hours. After the reaction, the cells were harvested by centrifugation (at 10,000 rpm for 10 minutes) and the culture supernatant was removed. After PBS was added to the harvested cells and mixed, the cells were harvested again by centrifugation to wash the cells. The washing operation was performed 5 times. Phages bound to the cells were eluted with 500 μl of eluent (0.1 N HCl solution containing 0.1% BSA, and adjusted to have a pH of to 2.2 with 1 M glycine solution) and neutralized by addition of 500 μL of a neutralization liquid (1 M Tris buffer, pH 9.1). The neutralized phage pool was infected with E. coli JM109, and cultured at 37° C. in LB-Amp/Glu agar medium overnight; and the colonies were harvested. After transformed E. coli prepared in LB medium to have OD$_{600\ nm}$=0.2 and a helper phage M13K07 ($10^{12}$ cfu) were statically cultured for 30 minutes, 100 mL of LB-Amp/Kan liquid medium was added, and the cells were cultured at 37° C. overnight. The phage culture was concentrated in a PEG/NaCl solution, and adjusted to a concentration of about $1\times10^{12}$ cfu/mL with a phosphate buffer. Biopanning on the cells was performed 3 times.

In step 4, purified M. tuberculosis LAM was reacted with a TB-scFv-immobilized plate, and biopanning was performed using a complex of TB-scFV and LAM. Specifically, 10 μg of purified M. tuberculosis LAM was added to a microplate having TB-scFv immobilized thereon at a concentration of 5 μg/ml, and a reaction was allowed to proceed at 25° C. for 1 hour. After washing, a phage pool bound to the cells obtained in step 3 was added, and a reaction was allowed to proceed at 25° C. for 2 hours. Subsequently, unreacted phages were removed by washing with the reaction buffer 10 times. The phage bound to the complex of TB-scFv and LAM was eluted with 100 µL of eluent, and then neutralized by adding 100 µL of neutralization liquid (1 M Tris buffer, pH 9.1). The neutralized phage pool was infected with *E. coli* JM109, and then cultured at 37° C. in LB-Amp/Glu agar medium overnight.

(3-4) Selection of LAM-Binding Chicken scFv Clone

For LAM-binding scFv, phage clones that specifically reacted with LAM were selected by phage ELISA. The phage pool obtained in step 4 of antigen biopanning using the chicken scFv library explained in (3-3) above was cultured as a single colony, and the obtained single colony was cultured in 50 µL of LB-Amp medium at 37° C. for 8 hours. After the cells were infected with 50 µL of a helper phage M13K07 ($10^{12}$ cfu/mL) solution, 400 µL of LB-Amp/Kan liquid medium was added, and cultured at 37° C. overnight to prepare a culture of single phage clones.

Phage ELISA was performed by adding 10 µg of purified *M. tuberculosis* LAM to a microplate having TB-scFv immobilized thereon at a concentration of 5 µg/ml, allowing a reaction to proceed at 25° C. for 1 hour to prepare a complex of TB-scFv and LAM, and screening for clones capable of reacting with the complex. The primary reaction was performed by adding 90 µL of a reaction buffer (a phosphate buffer containing 1% BSA, 1% skim milk, and 0.05% Tween 20) and 10 µL of a scFv display phage culture to an LAM-immobilized plate, and allowing the reaction to proceed at 25° C. for 1 hour. Subsequently, unreacted phages were removed by washing 3 times. The secondary reaction was performed by adding to the primary reaction solution 100 µL of an HRP-labeled anti-M13 phage p8 protein antibody diluted 5,000-fold with the same reaction buffer as above, and allowing the reaction to proceed at 25° C. for 1 hour. Subsequently, unreacted antibodies were removed by washing 3 times. A color development reaction was performed by adding 100 µL of a TMB solution to the secondary reaction solution, and allowing the reaction to proceed at room temperature for 10 minutes. After the color development, 100 µL of a 1 N sulfuric acid solution was added thereto to stop the reaction. Detection was conducted by measuring absorbance ($OD_{450-650\ nm}$) at wavelengths of 450-650 nm.

The clone reactive to LAM was subjected to PCR to amplify scFv gene, and the gene sequence was determined by direct sequencing method.

(3-5) Specimens for Use to Evaluate ELISA Using Bivalent Antibody

ELISA for acid-fast bacillary LAM detection and ELISA for tubercle bacillary LAM detection using bivalent antibodies were evaluated using acid-fast bacillary clinical isolates (38 strains of *M. tuberculosis*, 23 strains of *M. avium*, and 6 strains of *M. intracellulare*), BCG, six types of oral bacteria (*N. asteroides, N. farcinica, S. globisporus, C. albicans, A. israelii*, and *T. paurometabolum*), and sputum specimens (54 samples). Extraction of LAM from the cultured bacterial cells and from the sputum specimens was all performed under the same conditions. After NaOH was added to each sample to a final concentration of 0.4 M and mixed, the mixture was boiled for 30 minutes. After boiling, the mixture was neutralized by addition of a phosphate buffer.

4. Assay (4-1) Preparation of Bivalent Antibody

Single-chain antibody scFvA was modified into a bivalent antibody by a general method. VH and VL region genes were cloned from Myco-scFv (SEQ ID NO: 30), TB-scFv (SEQ ID NO: 12), and G3-scFv (SEQ ID NO: 39) into mammalian cell expression vectors having a rabbit constant region (trade names: pFUSEss-CHIg-rG*03 and pFUSE2ss-CLIg-rk1, produced by InvivoGen) to prepare VH and VL expression vectors. The VH and VL expression vectors were mixed and transfected into CHO cells. After the vector-transfected cells were cultured for 4 days, bivalent antibodies (bivalent Myco-scFv, bivalent TB-scFv, and bivalent G3-scFv) were isolated and purified from the supernatants using Protein A (produced by Bio-Rad).

(4-2) Biotin Labeling of Bivalent Antibody

Biotin labeling of each bivalent antibody was performed using a Sulfo-NHS-LC-Biotin labeling kit from Pierce in accordance with the operating manual accompanying the kit. The biotin-labeled antibody was used to construct an ELISA system.

(4-3) Construction of ELISA for Acid-Fast Bacillary LAM Detection Using Bivalent Antibody ELISA for acid-fast bacillary LAM detection using bivalent antibodies was constructed using bivalent TB-scFv, bivalent G3-scFv, and bivalent Myco-scFv (see (4-1) "Preparation of bivalent antibody").

The bivalent TB-scFv and bivalent G3-scFv were mixed in equal amounts, and adjusted to a concentration of 5 µg/ml with a phosphate buffer. The resulting mixture was added to a 96-well microplate at a proportion of 100 µL/well, and a reaction was allowed to proceed at 4° C. overnight, after which blocking was performed in a phosphate buffer containing 1% skim milk, thus producing an antibody plate having the bivalent antibodies immobilized thereon.

The primary reaction was performed by adding 100 µL of a sample diluted with a reaction buffer (Tris buffer containing 1% BSA, 1% skim milk, 0.14 M NaCl, and 0.1% Tween 20) to the wells of the aforementioned antibody plate, and allowing the reaction to proceed at 25° C. for 1 hour and 30 minutes. Subsequently, the plate was washed 3 times. The secondary reaction was performed by adding to the primary reaction solution 100 µL of biotin-labeled bivalent Myco-scFv diluted 5,000-fold with the same reaction buffer as above, and allowing the reaction to proceed at 25° C. for 1 hour and 30 minutes. Subsequently, unreacted antibodies were removed by washing 3 times. The tertiary reaction was performed by adding to the secondary reaction solution 100 µL of avidin-labeled HRP diluted 10,000-fold with the same reaction buffer as above, and allowing the reaction to proceed at 25° C. for 1 hour and 30 minutes. Subsequently, unreacted avidin-labeled HRP was removed by washing 3 times. A color-development reaction was performed by adding 100 µL of a TMB solution to the tertiary reaction solution, and allowing the reaction to proceed at room temperature for 10 minutes. After the color development, 100 µL of a 1N sulfuric acid solution was added to stop the reaction. Detection was conducted by measuring absorbance ($OD_{450-650\ nm}$) at wavelengths of 450-650 nm.

(4-4) Construction of ELISA for Tubercle Bacillary LAM Detection Using Bivalent Antibody ELISA for tubercle bacillary LAM detection using bivalent antibodies was constructed in the same manner as ELISA for acid-fast bacillary LAM detection described in (4-3) above, except that bivalent TB-scFv was used as a capture antibody, and biotin-labeled bivalent Myco-scFv was used as a detection antibody.

Example 5

Immunization of Chicken, and Antibody Titer Evaluation of Chicken Antiserum Against LAM Immunization of chicken was conducted through subcutaneous immunization of an entire amount of a BCG vaccine (100 mg wet weight/1 ml physiological saline) prepared by the method described in (3-1) of "3. Preparation of materials." Immunization was conducted 4 times at 14-day intervals, and antibody titer in blood of chicken was evaluated through ELISA.

Purified LAM of human tubercle bacillus *M. tuberculosis* (derived from strain Aoyama B, Nacalai Tesque) or purified LAM of *M. avium* (derived from strain serotype B, Nacalai Tesque) was adjusted with PBS to a concentration of 100 µL/ml. This was added to a 96-well microplate in an amount of 100 µL/well and allowed to react at 4° C. overnight, and blocking was performed in a phosphate buffer containing 1% skim milk to prepare an antigen plate.

The primary reaction was performed by adding 100 µL of chicken serum diluted with a reaction buffer (Tris buffer of pH 7.8 containing 1% BSA, 1% skim milk, 0.14 M NaCl, and 0.1% Tween 20) to each well of the antigen plate, and allowing the reaction to proceed at 25° C. for 1 hour. Subsequently, unreacted antibodies were removed by washing 3 times. The secondary reaction was performed by adding, to the primary reaction solution, 100 µL of HRP labeled anti-chicken IgY diluted 5,000-fold with the same reaction buffer, and allowing the reaction to proceed at 25° C. for 1 hour. Subsequently, unreacted antibodies were removed by washing 3 times. A color-development reaction was performed by adding 100 µL of TMB solution thereto, and allowing the reaction to proceed at room temperature for 10 minutes. After the color development, the reaction was stopped by adding 100 µL of 1 N sulfuric-acid solution. The detection was conducted by measuring absorbance at wavelengths of 450-650 nm ($OD_{450\text{-}650\ nm}$).

The results are shown in FIG. 9. In the figure, "-■-" represents reactivity of chicken antiserum to purified *M. tuberculosis* LAM, and "-●-" represents reactivity of chicken antiserum to purified *M. avium* LAM. As shown in FIG. 9, it was confirmed that immunization of chicken with BCG vaccine had sufficiently increased antibody titer against LAM. In addition, similar reactivity was observed to both tubercle bacillary LAM and acid-fast bacillary LAM.

Example 6

Preparation of Chicken scFv (Single-Chain Antibody) Against LAM (1) Preparation of Chicken scFv (Single-Chain Antibody) Against LAM A single-chain antibody scFv was isolated from the spleen cells of a chicken immunized with BCG vaccine. Specifically, in accordance with the method described in (3-2) of "3. Preparation of materials," total RNA was prepared from the spleen of a chicken, and PCR was performed using cDNA synthesized therefrom as template and the various primers described in Table 3 to prepare VH gene amplification products and VL gene amplification products. Next, chicken single-chain antibodies (VH gene/GS linker/VL gene) each having the VH gene and the VL gene joined via a GS linker (SEQ ID NO: 40) were prepared, and scFv display phage libraries were produced therefrom. Since the titer of each library was about $10^6$ cfu, it is presumed that each library had a diversity of $10^6$.

By using the prepared scFv display phage libraries, biopanning was conducted 3 times with BCG vaccine. For the purpose of isolating a single-chain antibody scFv that recognizes an epitope that is different from that of TB-scFv, for the fourth panning, a complex formed through a reaction of LAM of *M. tuberculosis* (derived from strain Aoyama B) with TB-scFv that has been immobilized on a microplate was used. A LAM solution of *M. tuberculosis* was allowed to react on a microplate having TB-scFv immobilized thereon, the microplate was washed 3 times, BCG panning phage pool was added thereto, and a reaction was allowed to proceed at 25° C. for 2 hours. After the reaction, the microplate was washed 3 times, and LAM binding phages were eluted. Ultimately, 200 clones were randomly selected from each panning pool, and screening of LAM reactive clones was conducted using a complex of TB-scFv and LAM. About 10 LAM reactive clones were obtained from each of the libraries. As a result of base sequence analysis, it was confirmed that the sequences of the clones obtained from each library were nearly identical.

As a result, a single clone of single-chain antibody scFv (G3-scFv) was successfully isolated from a scFv display phage library prepared from the spleen of the chicken immunized with BCG vaccine. FIG. 10 shows the amino acid sequence (SEQ ID NO: 39) of the single-chain antibody G3-scFv isolated from a chicken spleen library, together with the positions of CDR1, CDR2, and CDR3 regions of the heavy chain variable region, GS linker, and CDR1, CDR2, and CDR3 regions of the light chain variable region.

(2) LAM Reactivity of Chicken scFv (Single-Chain Antibody)

Reactivity of the produced G3-scFv as described above was evaluated using a plate on which purified LAM of *M. tuberculosis* had been immobilized and a plate on which purified LAM of *M. avium* had been immobilized. Specifically, G3-scFv was solubilized in accordance with the method described in (1-6) of "1. Preparation of materials" to prepare solubilized G3-scFv. Next, biotin labeling was conducted in accordance with the method described in the same (1-7), and reactivity to the antigen plates (purified LAM immobilized microtiter plates), i.e., a plate having purified LAM of *M. tuberculosis* immobilized thereon and a plate having purified LAM of *M. avium* immobilized thereon was evaluated through an assay with the ELISA method.

As a result, G3-scFv exhibited similar reactivity to both tubercle bacillary LAM and acid-fast bacillary LAM. From this result, it was considered that single-chain antibody G3-scFv of chicken is an antibody having reactivity to acid-fast bacillary LAM in general including tubercle bacillary LAM.

Example 7

Construction Of Lam Detection Elisa Using Bivalent Antibodies

With an intention to put the present invention to practical use, three types of single-chain antibodies scFvs (Myco-scFv, TB-scFv, and G3-scFv) produced in Examples 1 and 6 were modified into bivalent antibodies in accordance with the method described in (4-1) of "Preparation of bivalent antibody," and two types of ELISA, acid-fast bacillary LAM detection ELISA and tubercle bacillary LAM detection ELISA, were constructed based on the reaction specificity of the bivalent antibodies. Specifically, for the acid-fast bacillary LAM detection ELISA, bivalent TB-scFv and bivalent G3-scFv were mixed and immobilized on a plate as capture antibodies, and bivalent Myco-scFv that had been biotin-labeled was used as a detection antibody. For the tubercle bacillary LAM detection ELISA, bivalent TB-scFv was immobilized on a plate as a capture antibody, and bivalent Myco-scFv that had been biotin-labeled was used as a detection antibody. Details thereof are as described in (4-3) and (4-4) of "4. Assay."

Figure 11:
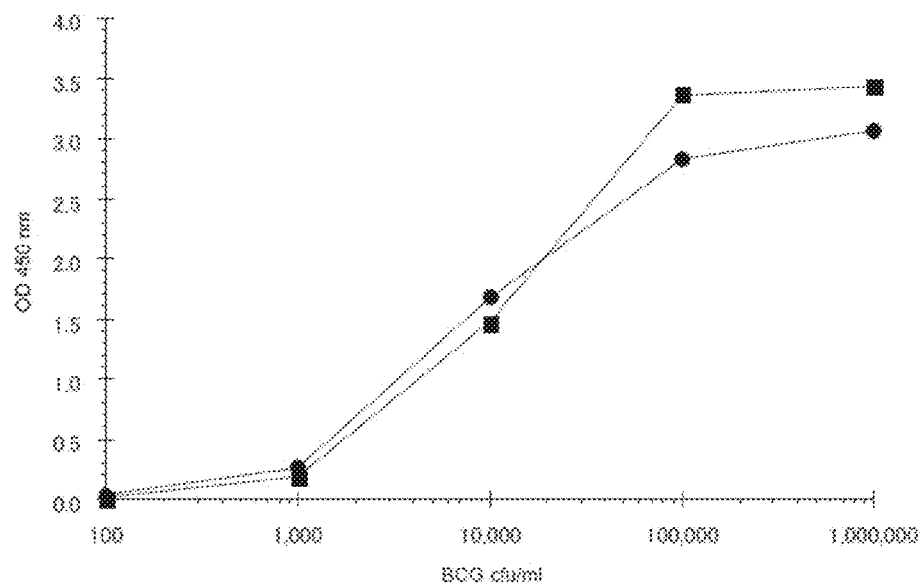

Evaluation of the constructed acid-fast bacillary LAM detection ELISA and tubercle bacillary LAM detection ELISA was conducted by assaying LAM extracted from cultured BCG bacterial cells (FIG. 11). As a result, as shown in FIG. 11, in both the acid-fast bacillary LAM detection ELISA (-■-) and the tubercle bacillary LAM detection ELISA (-●-), it was possible to detect LAM of BCG at equivalent sensitivity.

Example 8

Detection Sensitivity Evaluation of LAM Detection ELISA Using Bivalent Antibodies In order to conduct sensitivity evaluation of ELISA using bivalent antibodies, cultured BCG bacterial cells were diluted in a series from $10^6$ cfu/ml to 61 cfu/ml, and a portion of each of the dilution solutions was used to extract genomic DNA to perform a nucleic acid amplification test (NAAT), and another portion thereof was used to extract LAM to perform the acid-fast bacillary LAM detection ELISA.

The result of the acid-fast bacillary LAM detection ELISA is shown in FIG. 12. As shown in the table in FIG. 12, the detection sensitivity of the nucleic acid amplification test (NAAT) was about 500 cfu/ml, whereas the detection sensitivity of the acid-fast bacillary LAM detection ELISA was about 250 cfu/ml. A repetitive sequence which is a target of the nucleic acid amplification test is different depending on the bacterial strain in terms of the number of repeats, and it is said that the detection sensitivity may be different depending on the bacterial strain. Although the sensitivity of genetic testing was low since the repetitive sequence in BCG is small, it is said that a bacterial strain having a large repetitive sequence generally results in a detection sensitivity of 100 cfu/ml.

With the result described above, it has been proven that the acid-fast bacillary LAM detection ELISA of the present invention using bivalent antibodies is a very highly sensitivity immunoassay method with a detection sensitivity that is equivalent to or higher than that of the nucleic acid amplification test.

Example 9

Cross-Reactivity Test of LAM Detection ELISA Using Bivalent Antibodies

In oral bacteria, there are species that have a membrane antigen with a structure similar to the component of LAM. When acid-fast bacillary LAM and tubercle bacillary LAM in a sputum specimen is to be detected, cross-reactivity with these oral bacteria becomes very problematic, and this is one of the obstacles for establishing a detection immunoassay of acid-fast bacilli and tubercle bacilli using sputum.

Here, in order to examine cross-reactivity to oral bacteria in the LAM detection ELISA, liquid cultures were prepared from each of *N. asteroids* (abbreviated as "Na"), *N. farcinica* (abbreviated as "Nf"), *S. globisporus* (abbreviated as "Sg"), *C. albicans* (abbreviated as "Ca"), *A. israelii* (abbreviated as "Ai"), and *T. paurometabolum* (abbreviated as "Tp"). The liquid cultures were adjusted to be $10^6$ cfu/ml and $10^8$ cfu/ml ($10^7$ cfu/ml only for Ca), and LAMs were extracted therefrom as in cultured BCG bacterial cells to be assayed in the LAM detection ELISA. FIG. 13 shows the result of the acid-fast bacillary LAM detection ELISA.

As can be understood from FIG. 13, although reactivity of BCG used as a control had reached a maximum value at a concentration of $10^5$ cfu/ml, each of the oral bacteria did not exhibit reactivity at all at high concentration levels of bacterial cells of $10^8$ cfu/ml. The completely same result was seen with the tubercle bacillary LAM detection ELISA.

The above described results have proven that the single-chain antibodies scFvs (Myco-scFv, TB-scFv, and G3-scFv) that we have obtained have high affinity to acid-fast bacillary LAM and tubercle bacillary LAM, and that it is possible to detect acid-fast bacilli (including a tubercle bacillus) at a sensitivity as high as that of a nucleic acid amplification test by combining these antibodies as a bivalent antibody, and that provided are an assay and antibodies that are very selective and specific with no cross-reactivity with oral bacteria at all.

Example 10

Evaluation of LAM Detection ELISA Using Bivalent Antibodies with Clinical Isolates With the usage of acid-fast bacillary clinical isolates, the acid-fast bacillary LAM detection ELISA and the tubercle bacillary LAM detection ELISA using bivalent antibodies were evaluated.

As the clinical isolates, 38 strains of *M. tuberculosis*, 23 strains of *M. avium*, and 6 strains of *M. intracellulare* were used. The *M. avium* strains and the *intracellulare* strains are pathogenic bacteria for MAC disease. LAMs were extracted from cultured bacterial cells of these, and the acid-fast bacillary LAM detection ELISA and the tubercle bacillary LAM detection ELISA using bivalent antibodies were performed. The results are shown in FIG. 14.

In FIG. 14, "A" shows the results of the acid-fast bacillary LAM detection ELISA (black bar) and the tubercle bacillary LAM detection ELISA (white bar) performed on the 38 strains of tubercle bacillus clinical isolates (*M. tuberculosis*). "B" shows the results of the acid-fast bacillary LAM detection ELISA (black bar) and the tubercle bacillary LAM detection ELISA (white bar) performed on the 29 strains of non-tuberculous acid-fast bacilli (23 strains of *M. avium* and 6 strains of *M. intracellulare*).

Both in the acid-fast bacillary LAM detection ELISA and the tubercle bacillary LAM detection ELISA, reactivity was seen in all of the 38 strains of *M. tuberculosis*, the 23 strains of *M. avium*, and the 6 strains of *M. intracellulare*. Although the acid-fast bacillary LAM detection ELISA exhibited an equivalent reaction for tubercle bacilli and non-tuberculous acid-fast bacilli, the tubercle bacillary LAM detection ELISA exhibited low reactivity to non-tuberculous acid-fast bacilli.

For the purpose of differentiating tubercle bacilli from non-tuberculous acid-fast bacilli solely from the result of the LAM detection ELISA, a ratio (value from the acid-fast bacillary LAM detection ELISA/value from the tubercle bacillary LAM detection ELISA) of the value from the acid-fast bacillary LAM detection ELISA and the value from the tubercle bacillary LAM detection ELISA was calculated (FIG. 15). As a result, with tubercle bacillus, out of the 38 strains, there was only 1 strain that had a ratio of the two measurement values exceeding 3-fold. On the other hand, with non-tuberculous acid-fast bacilli, 23 strains out of the 29 strains had a ratio of 3-fold or higher.

The result described above indicates that the LAM detection ELISA can detect LAM almost without being affected by inter-strain differences. In addition, it has been proven that, by calculating the ratio (value from the acid-fast bacillary LAM detection ELISA/value from the tubercle bacillary LAM detection ELISA) from both assay systems, it is possible to differentiate (distinguish) tubercle bacilli from non-tuberculous acid-fast bacilli with an excellent score of 97% sensitivity and 80% specificity, and that the method of the present invention is the world's first immunoassay system as a LAM detection ELISA "capable of detecting acid-fast bacilli in general, and also distinguishing tubercle bacilli from non-tuberculous acid-fast bacilli."

Example 11

Evaluation of LAM Detection ELISA Using Bivalent Antibodies with Clinical Sputum Specimens In order to evaluate the capability of the LAM detection ELISA using bivalent antibodies constructed in Example 7, evaluation was conducted using clinical sputum specimens from 54 cases. The evaluation was conducted by both a direct smear test (Smear) and the nucleic acid amplification test (NAAT). The results of the direct smear test and the nucleic acid amplification test are summarized in Table 4.

TABLE 4

| Smear | NAAT | Number of samples |
|---|---|---|
| 3+ | + | 11 |
| 2+ | + | 4 |
| 1+ | + | 18 |
| Scanty | + | 9 |
| Scanty | − | 1 |
| − | + | 3 |
| − | − | 8 |

From the direct smear test, there were 43 positive cases (3+, 2+, 1+, Scanty); and from the nucleic acid amplification test, there were 45 positive cases (+). Of these cases, 42 cases were positive in both tests, 8 cases were negative in both tests, and 3 cases were positive only in the nucleic acid amplification test.

LAMs were extracted from the clinical sputum specimens and assayed with the acid-fast bacillary LAM detection ELISA and the tubercle bacillary LAM detection ELISA, and the results of those are each shown in Table 5 and FIG. 16. Table 5 shows detection rates from the acid-fast bacillary LAM detection ELISA and the tubercle bacillary LAM detection ELISA together.

TABLE 5

| | | Number of | LAM-ELISA (n) | |
|---|---|---|---|---|
| NAAT | Smear | samples | Acid-fast bacilli | Tubercle bacilli |
| + | 3+ | 11 | 100% (11/11) | 100% (11/11) |
| + | 2+ | 4 | 100% (4/4) | 100% (4/4) |
| + | 1+ | 18 | 100% (18/18) | 100% (18/18) |
| + | Scanty | 9 | 100% (9/9) | 89% (8/9) |
| + | − | 3 | 100% (3/3) | 100% (3/3) |
| − | Scanty | 1 | 0% (0/1) | 0% (0/1) |
| − | − | 8 | 0% (0/8) | 0% (0/8) |

As shown in Table 5, the results from the acid-fast bacillary LAM detection ELISA and the tubercle bacillary LAM detection ELISA were almost identical. In groups confirmed to score 1+ or higher in terms of the number of bacterial cells in the smear test, reactivity in ELISA had reached the maximum value in most of the specimens. Even with "Scanty" in which the number of bacterial cells was small, reactivity in ELISA had reached the maximum value in 50% of the specimens. Furthermore, even in 3 cases that had very small number of bacterial cells and was determined positive only in the nucleic acid amplification test, higher values were obtained in all of them than specimens that were determined negative in the nucleic acid amplification test. With the acid-fast bacillary LAM detection ELISA, although LAM was detected from all the specimens that were determined positive in the nucleic acid amplification test, LAM could not be detected even in a single case from the specimens that were determined negative in the nucleic acid amplification test. Thus, sensitivity and specificity of the acid-fast bacillary LAM detection ELISA matched 100% when compared to the nucleic acid amplification test. All cases matched that of the nucleic acid amplification test also in the tubercle bacillary LAM detection ELISA, except that one case determined positive in the nucleic acid amplification test and "scanty" in the smear test did not match the result of the nucleic acid amplification test. Furthermore, the one case that did not match was only slightly below a cutoff value.

The above described results indicate that the LAM detection ELISA of the present invention is a test capable of screening and selecting acid-fast bacilli infected patients with sensitivity and specificity equivalent to the nucleic acid amplification test.

Next, in order to confirm that there is a correlation between the value of the LAM detection ELISA and the amount of bacteria, a dilution measurement was conducted.

Extraction solutions from sputum specimens were diluted 5-fold, 25-fold, and 125-fold, the diluted solutions were assayed together with purified LAM that was used as a standard preparation, and LAM concentrations therein were calculated. The result is shown in FIG. 17.

The specimens were divided in groups (I: negative in both nucleic acid amplification test and smear test, II: positive in nucleic acid amplification test and negative in smear test, III: positive in nucleic acid amplification test and "scanty" in smear test, IV: 1+ in smear test, V: 2+ in smear test, VI: 3+ in smear test) using the nucleic acid amplification test and the amount of bacteria based on the smear test, and compared with LAM concentration (pg/ml). As a result, as shown in FIG. 17, since the average value of LAM concentration increases from the group with small amount of bacteria toward the group with large amount of bacteria (I to VI), it shows that there is a positive correlation between the amount of bacteria and LAM concentration. From the result described above, it was shown that the amount of bacteria can be predicted by quantifying LAM concentration.

These results have shown that the method of the present invention has sensitivity and specificity equivalent to that of the nucleic acid amplification test and is a test capable of additionally determining the amount of bacteria, and the method has been proven to be applicable for therapeutic monitoring etc., of tuberculosis.

Example 12

LAM Stability Evaluation

When transporting sputum specimens, it is necessary to transport the specimens under strict control due to the problem of infectiousness. In such a case, the cost becomes high, and available areas become limited. If a sputum specimen is sterilized after being collected, ordinary transportation thereof becomes possible. In order to completely sterilize acid-fast bacilli, treatments such as boiling for 30 minutes or longer and pressurized steam sterilization (autoclave etc.,) are necessary. When such treatments are performed, it may be predicted that the structure of LAM becomes altered. We examined whether or not the constructed LAM detection ELISA described above is resistant to rigorous sterilization treatment and can correctly detect LAM.

LAMs were extracted each from bacterial cells (autoclaved bacteria) obtained by autoclaving (121° C., 20 minutes) cultured BCG bacterial cells, bacterial cells that have been boiled for 30 minutes at 100° C. (boil-treated bacteria), and untreated bacteria, and assay was performed thereon using the acid-fast bacillary LAM detection ELISA. The results are shown in FIG. 18. When the untreated bacteria (white bar), the boil-treated bacteria (black bar), and the autoclaved bacteria (gray bar) are compared, the values were completely identical in all of them, indicating that it is possible to also assay LAM in bacterial cells subjected to rigorous treatments such as boiling and autoclaving, similarly to untreated bacteria.

In addition, evaluation of storage stability was conducted using bacterial cells that had been autoclaved (121° C., 20 minutes), which is the most rigorous treatment. After leaving autoclaved BCG bacterial cells at 25° C. for 7 days, the acid-fast bacillary LAM detection ELISA was performed on LAM extracted therefrom. FIG. 19 shows the results (black bar), and the results (white bar) of the acid-fast bacillary LAM detection ELISA performed on LAM extracted from BCG bacterial cells immediately after autoclaving. As can be understood from FIG. 19, there was almost no difference between the two, and a result similar to that of bacterial cell immediately after treatment was obtained from bacterial cells left for 7 days after autoclaving. This indicates that assay is possible for at least one week after sterilization treatment.

From the results described above, it was confirmed that, with the present assay system, assay is possible even when the target is bacterial cells having performed thereon rigorous treatments such as pressurized steam sterilization (autoclaving), and the assay can be performed stably for at least one week after treatment.

Therefore, even in an area without a special specimen transport system put in place, specimen shipment is possible with general transport systems such as mail and the like. Furthermore, in terms of time, since there is a grace period of about one week, it is conceivable that a delay in specimen transport would not be a problem.

Free Text

SEQ ID NOs: 9 and 10 show the unit amino acid sequences of GS linker sequences, and SEQ ID NOs: 11 and 40 show the amino acid sequences of the linker sequences used in the present invention. SEQ ID NOs: 13 to 16 show the amino acid sequences of antibody heavy chain variable region sense primers; SEQ ID NO: 17 shows the amino acid sequence of an antibody heavy chain variable region antisense primer; SEQ ID NOs: 18 to 20 and 24 show the amino acid sequences of antibody light chain variable region sense primers; SEQ ID NOs: 21 to 23 and 25 show the amino acid sequences of antibody light chain variable region antisense primers; SEQ ID NO: 26 shows the amino acid sequence of a GS linker sense primer; SEQ ID NO: 27 shows the amino acid sequence of a GS linker antisense primer; SEQ ID NO: 28 shows the amino acid sequence of a restriction enzyme (SfiI) site primer; and SEQ ID NO: 29 shows the amino acid sequence of a restriction enzyme (NotI) site primer (see Table 1).

SEQ ID NO: 41 shows the amino acid sequence of an antibody heavy chain variable region sense primer; SEQ ID NO: 42 shows the amino acid sequence of an antibody heavy chain variable region antisense primer; SEQ ID NO: 43 shows the amino acid sequence of an antibody light chain variable region sense primer; SEQ ID NO: 44 shows the amino acid sequence of an antibody light chain variable region antisense primer; SEQ ID NO: 45 shows the amino acid sequence of a GS linker sense primer; and SEQ ID NO: 46 shows the amino acid sequence of a GS linker antisense primer (see Table 3).

The invention claimed is:

1. A monoclonal antibody that is capable of binding to acid-fast bacillary lipoarabinomannan, said monoclonal antibody comprising a heavy chain variable region and a light chain variable region joined via a linker, the heavy chain variable region comprising heavy chains CDR1 to CDR3 shown in (a) to (c) below, and the light chains comprising CDR1 to CDR3 shown in (d) to (f) below:
   (a) a heavy chain CDR1 consisting of the amino acid sequence set forth in SEQ ID NO: 1,
   (b) a heavy chain CDR2 consisting of the amino acid sequence set forth in SEQ ID NO: 2,
   (c) a heavy chain CDR3 consisting of the amino acid sequence set forth in SEQ ID NO: 3,
   (d) a light chain CDR1 consisting of the amino acid sequence set forth in SEQ ID NO: 4,
   (e) a light chain CDR2 consisting of the amino acid sequence set forth in SEQ ID NO: 5, and
   (f) a light chain CDR3 consisting of the amino acid sequence set forth in SEQ ID NO: 6.

2. The monoclonal antibody according to claim 1, wherein the monoclonal antibody consists of the amino acid sequence set forth in SEQ ID NO: 12.

3. The monoclonal antibody according to claim 1 or claim 2, which is a monovalent or bivalent antibody.

4. A kit comprising the monoclonal antibody of claim 3.

5. A kit comprising the monoclonal antibody of claim 1 or claim 2.

6. A mycobacterium detection tool comprising a solution-absorbing piece formed from a material capable of transferring a test sample through capillary action, the solution-absorbing piece comprising:
   (1) a sample collection part for absorbing and collecting the test sample;
   (2) a labeled antibody part supporting a labeled monoclonal antibody that specifically reacts with acid-fast bacillary lipoarabinomannan;
   (3) a determination part including a test result display part (a) that has immobilized thereon an unlabeled monoclonal antibody that specifically reacts with acid-fast bacillary lipoarabinomannan; and (4) a solution absorption part for absorbing remaining solution of the test sample that has moved through the sample collection part, the labeled antibody part, and the determination part, wherein each of said labeled and said unlabeled monoclonal antibodies is an antibody of claim 1 or claim 2.

7. The mycobacterium detection tool according to claim 6, wherein the determination part (3) further comprises a control display part (b) having immobilized thereon an unlabeled antibody that reacts with the labeled monoclonal antibody, the control display part being disposed apart from the test result display part (a).

8. A *mycobacterium* detection tool comprising a solution-absorbing piece formed from a material capable of transferring a test sample through capillary action, the solution-absorbing piece comprising:

(1) a sample collection part for absorbing and collecting the test sample;

(2) a labeled antibody part supporting a labeled monoclonal antibody that specifically reacts with acid-fast bacillary lipoarabinomannan;

(3) a determination part including a test result display part (a) that has immobilized thereon an unlabeled monoclonal antibody that specifically reacts with acid-fast bacillary lipoarabinomannan; and (4) a solution absorption part for absorbing remaining solution of the test sample that has moved through the sample collection part, the labeled antibody part, and the determination part, wherein each of said labeled and said unlabeled monoclonal antibodies is an antibody of claim 3.

9. The mycobacterium detection tool according to claim 8, wherein the determination part (3) further comprises a control display part (b) having immobilized thereon an unlabeled antibody that reacts with the labeled monoclonal antibody, the control display part being disposed apart from the test result display part (a).

* * * * *

SEQUENCE LISTING

```
<160> NUMBER OF SEQ ID NOS: 54

<210> SEQ ID NO 1
<211> LENGTH: 5
<212> TYPE: PRT
<213> ORGANISM: Unknown
<220> FEATURE:
<223> OTHER INFORMATION: the sequence is Leporidae

<400> SEQUENCE: 1

Thr Tyr Tyr Met Thr
1               5

<210> SEQ ID NO 2
<211> LENGTH: 16
<212> TYPE: PRT
<213> ORGANISM: Unknown
<220> FEATURE:
<223> OTHER INFORMATION: the sequence is Leporidae

<400> SEQUENCE: 2

Thr Ile Asp Ser Tyr Gly Asn Arg Tyr Tyr Ala Ser Trp Ala Lys Gly
1               5                   10                  15
```

<210> SEQ ID NO 3
<211> LENGTH: 10
<212> TYPE: PRT
<213> ORGANISM: Unknown
<220> FEATURE:
<223> OTHER INFORMATION: the sequence is Leporidae

<400> SEQUENCE: 3

Asp Asp Leu Gly Trp Asn Asn Asp Asn Ile
1               5                   10

<210> SEQ ID NO 4
<211> LENGTH: 13
<212> TYPE: PRT
<213> ORGANISM: Unknown
<220> FEATURE:
<223> OTHER INFORMATION: the sequence is Leporidae

<400> SEQUENCE: 4

Gln Ala Ser Glu Ser Val Tyr Gly Asn Asn Gln Leu Ala
1               5                   10

<210> SEQ ID NO 5
<211> LENGTH: 7
<212> TYPE: PRT
<213> ORGANISM: Unknown
<220> FEATURE:
<223> OTHER INFORMATION: the sequence is Leporidae

<400> SEQUENCE: 5

Lys Ala Ser Thr Leu Ala Ser
1               5

<210> SEQ ID NO 6
<211> LENGTH: 13
<212> TYPE: PRT
<213> ORGANISM: Unknown
<220> FEATURE:
<223> OTHER INFORMATION: the sequence is Leporidae

<400> SEQUENCE: 6

Cys Gly Gly Tyr Lys Gly Ser Thr Thr Asp Gly Ala Ala
1               5                   10

<210> SEQ ID NO 7
<211> LENGTH: 119
<212> TYPE: PRT
<213> ORGANISM: Unknown
<220> FEATURE:
<223> OTHER INFORMATION: the sequence is Leporidae

<400> SEQUENCE: 7

Ala Gln Ser Val Lys Glu Ser Gly Gly Arg Leu Val Thr Pro Gly Gly
1               5                   10                  15

Ser Leu Thr Leu Thr Cys Thr Val Ser Gly Ile Asp Leu Thr Thr Tyr
            20                  25                  30

Tyr Met Thr Trp Ile Arg Gln Ala Pro Gly Lys Gly Leu Glu Trp Ile
        35                  40                  45

Gly Thr Ile Asp Ser Tyr Gly Asn Arg Tyr Tyr Ala Ser Trp Ala Lys
    50                  55                  60

Gly Gln Phe Thr Ile Ser Lys Thr Ser Ser Thr Thr Val Asp Leu Lys
65                  70                  75                  80

Met Thr Gly Leu Thr Ala Ser Asp Thr Ala Thr Tyr Phe Cys Thr Arg

```
                    85                  90                  95
Asp Asp Leu Gly Trp Asn Asn Asp Asn Ile Trp Gly Pro Gly Thr Leu
                100                 105                 110
Val Thr Val Ser Ser Ser Ser
        115
```

<210> SEQ ID NO 8
<211> LENGTH: 112
<212> TYPE: PRT
<213> ORGANISM: Unknown
<220> FEATURE:
<223> OTHER INFORMATION: the sequence is Leporidae

<400> SEQUENCE: 8

```
Glu Leu Val Met Thr Gln Thr Pro Ser Lys Ser Val Pro Val Gly
1               5                   10                  15

Asp Thr Val Thr Ile Asn Cys Gln Ala Ser Glu Ser Val Tyr Gly Asn
                20                  25                  30

Asn Gln Leu Ala Trp Tyr Gln Gln Lys Pro Gly Gln Pro Pro Lys Leu
            35                  40                  45

Leu Ile Tyr Lys Ala Ser Thr Leu Ala Ser Gly Val Pro Ser Arg Phe
        50                  55                  60

Lys Gly Ser Gly Tyr Gly Thr Gln Phe Thr Leu Thr Ile Ser Asp Val
65                  70                  75                  80

Val Cys Asp Asp Ala Ala Thr Tyr Tyr Cys Gly Tyr Lys Gly Ser
                85                  90                  95

Thr Thr Asp Gly Ala Ala Phe Gly Gly Gly Thr Glu Val Val Val Lys
                100                 105                 110
```

<210> SEQ ID NO 9
<211> LENGTH: 4
<212> TYPE: PRT
<213> ORGANISM: Artificial Sequence
<220> FEATURE:
<223> OTHER INFORMATION: linker

<400> SEQUENCE: 9

```
Gly Gly Gly Ser
1
```

<210> SEQ ID NO 10
<211> LENGTH: 5
<212> TYPE: PRT
<213> ORGANISM: Artificial Sequence
<220> FEATURE:
<223> OTHER INFORMATION: linker

<400> SEQUENCE: 10

```
Gly Gly Gly Gly Ser
1               5
```

<210> SEQ ID NO 11
<211> LENGTH: 15
<212> TYPE: PRT
<213> ORGANISM: Artificial Sequence
<220> FEATURE:
<223> OTHER INFORMATION: linker

<400> SEQUENCE: 11

```
Gly Gly Gly Gly Ser Gly Gly Gly Gly Ser Gly Gly Gly Gly Ser
1               5                   10                  15
```

-continued

<210> SEQ ID NO 12
<211> LENGTH: 246
<212> TYPE: PRT
<213> ORGANISM: Unknown
<220> FEATURE:
<223> OTHER INFORMATION: the sequence is Leporidae

<400> SEQUENCE: 12

Ala Gln Ser Val Lys Glu Gly Gly Arg Leu Val Thr Pro Gly Gly
1               5                   10                  15

Ser Leu Thr Leu Thr Cys Thr Val Ser Gly Ile Asp Leu Thr Thr Tyr
            20                  25                  30

Tyr Met Thr Trp Ile Arg Gln Ala Pro Gly Lys Gly Leu Glu Trp Ile
        35                  40                  45

Gly Thr Ile Asp Ser Tyr Gly Asn Arg Tyr Tyr Ala Ser Trp Ala Lys
    50                  55                  60

Gly Gln Phe Thr Ile Ser Lys Thr Ser Ser Thr Val Asp Leu Lys
65                  70                  75                  80

Met Thr Gly Leu Thr Ala Ser Asp Thr Ala Thr Tyr Phe Cys Thr Arg
                85                  90                  95

Asp Asp Leu Gly Trp Asn Asn Asp Asn Ile Trp Gly Pro Gly Thr Leu
            100                 105                 110

Val Thr Val Ser Ser Ser Gly Gly Gly Ser Gly Gly Gly
        115                 120                 125

Ser Gly Gly Gly Ser Glu Leu Val Met Thr Gln Thr Pro Ser Ser
    130                 135                 140

Lys Ser Val Pro Val Gly Asp Thr Val Thr Ile Asn Cys Gln Ala Ser
145                 150                 155                 160

Glu Ser Val Tyr Gly Asn Asn Gln Leu Ala Trp Tyr Gln Gln Lys Pro
                165                 170                 175

Gly Gln Pro Pro Lys Leu Leu Ile Tyr Lys Ala Ser Thr Leu Ala Ser
            180                 185                 190

Gly Val Pro Ser Arg Phe Lys Gly Ser Gly Tyr Gly Thr Gln Phe Thr
        195                 200                 205

Leu Thr Ile Ser Asp Val Val Cys Asp Asp Ala Ala Thr Tyr Tyr Cys
    210                 215                 220

Gly Gly Tyr Lys Gly Ser Thr Thr Asp Gly Ala Ala Phe Gly Gly
225                 230                 235                 240

Thr Glu Val Val Val Lys
                245

<210> SEQ ID NO 13
<211> LENGTH: 31
<212> TYPE: DNA
<213> ORGANISM: Artificial Sequence
<220> FEATURE:
<223> OTHER INFORMATION: VH region sense primer

<400> SEQUENCE: 13
gccggccgcc cagtcggtgg aggagtccrg g                              31

<210> SEQ ID NO 14
<211> LENGTH: 31
<212> TYPE: DNA
<213> ORGANISM: Artificial Sequence
<220> FEATURE:
<223> OTHER INFORMATION: VH region sense primer

<400> SEQUENCE: 14
gccggccgcc cagtcggtga aggagtccga g                          31

<210> SEQ ID NO 15
<211> LENGTH: 31
<212> TYPE: DNA
<213> ORGANISM: Artificial Sequence
<220> FEATURE:
<223> OTHER INFORMATION: VH region sense primer

<400> SEQUENCE: 15
gccggccgcc cagtcgytgg aggagtccgg g                          31

<210> SEQ ID NO 16
<211> LENGTH: 33
<212> TYPE: DNA
<213> ORGANISM: Artificial Sequence
<220> FEATURE:
<223> OTHER INFORMATION: VH region sense primer

<400> SEQUENCE: 16
gccggccgcc cagsagcagc tgrtggagtc cgg                        33

<210> SEQ ID NO 17
<211> LENGTH: 38
<212> TYPE: DNA
<213> ORGANISM: Artificial Sequence
<220> FEATURE:
<223> OTHER INFORMATION: VH region antisense primer

<400> SEQUENCE: 17
cctccacctg aggatgarga gayggtgacc agggtgcc                   38

<210> SEQ ID NO 18
<211> LENGTH: 32
<212> TYPE: DNA
<213> ORGANISM: Artificial Sequence
<220> FEATURE:
<223> OTHER INFORMATION: VL region sense primer

<400> SEQUENCE: 18
gcggatcgga gctcgtgmtg acccagactc ca                         32

<210> SEQ ID NO 19
<211> LENGTH: 32
<212> TYPE: DNA
<213> ORGANISM: Artificial Sequence
<220> FEATURE:
<223> OTHER INFORMATION: VL region sense primer

<400> SEQUENCE: 19
gcggatcgga gctcgatmtg acccagactc ca                         32

<210> SEQ ID NO 20
<211> LENGTH: 32
<212> TYPE: DNA
<213> ORGANISM: Artificial Sequence
<220> FEATURE:
<223> OTHER INFORMATION: VL region sense primer

<400> SEQUENCE: 20
gcggatcgga gctcgtgatg acccagactg aa                         32

<210> SEQ ID NO 21
<211> LENGTH: 34
<212> TYPE: DNA
<213> ORGANISM: Artificial Sequence
<220> FEATURE:
<223> OTHER INFORMATION: VL region antisense primer

<400> SEQUENCE: 21
acctgcggcc gcttaggatc tccagctcgg tccc                                34

<210> SEQ ID NO 22
<211> LENGTH: 34
<212> TYPE: DNA
<213> ORGANISM: Artificial Sequence
<220> FEATURE:
<223> OTHER INFORMATION: VL region antisense primer

<400> SEQUENCE: 22
acctgcggcc gcttttgatt tccacattgg tgcc                                34

<210> SEQ ID NO 23
<211> LENGTH: 34
<212> TYPE: DNA
<213> ORGANISM: Artificial Sequence
<220> FEATURE:
<223> OTHER INFORMATION: VL region antisense primer

<400> SEQUENCE: 23
acctgcggcc gcttttgacs accacctcgg tccc                                34

<210> SEQ ID NO 24
<211> LENGTH: 34
<212> TYPE: DNA
<213> ORGANISM: Artificial Sequence
<220> FEATURE:
<223> OTHER INFORMATION: VL region sense primer

<400> SEQUENCE: 24
gcggatcgga gctcgtgctg actcagtcgc cctc                                34

<210> SEQ ID NO 25
<211> LENGTH: 36
<212> TYPE: DNA
<213> ORGANISM: Artificial Sequence
<220> FEATURE:
<223> OTHER INFORMATION: VL region antisense primer

<400> SEQUENCE: 25
acctgcggcc gcgcctgtga cggtcagctg ggtccc                              36

<210> SEQ ID NO 26
<211> LENGTH: 61
<212> TYPE: DNA
<213> ORGANISM: Artificial Sequence
<220> FEATURE:
<223> OTHER INFORMATION: GS linker sense primer

<400> SEQUENCE: 26
tcatcctcag gtggaggcgg ttcaggcgga ggtggctctg gcggtggcgg atcggagctc    60
g                                                                    61

<210> SEQ ID NO 27
<211> LENGTH: 61
<212> TYPE: DNA
<213> ORGANISM: Artificial Sequence
<220> FEATURE:
<223> OTHER INFORMATION: GS linker antisense primer

<400> SEQUENCE: 27

-continued

```
cgagctccga tccgccaccg ccagagccac ctccgcctga accgcctcca cctgaggatg    60
a                                                                    61
```

<210> SEQ ID NO 28
<211> LENGTH: 22
<212> TYPE: DNA
<213> ORGANISM: Artificial Sequence
<220> FEATURE:
<223> OTHER INFORMATION: Sfi-I site primer

<400> SEQUENCE: 28

```
agcggcccag ccggccgccc ag                                             22
```

<210> SEQ ID NO 29
<211> LENGTH: 12
<212> TYPE: DNA
<213> ORGANISM: Artificial Sequence
<220> FEATURE:
<223> OTHER INFORMATION: Not-I site primer

<400> SEQUENCE: 29

```
acctgcggcc gc                                                        12
```

<210> SEQ ID NO 30
<211> LENGTH: 246
<212> TYPE: PRT
<213> ORGANISM: Unknown
<220> FEATURE:
<223> OTHER INFORMATION: the sequence is Leporidae

<400> SEQUENCE: 30

```
Ala Gln Ser Val Lys Glu Ser Gly Gly Arg Leu Val Thr Pro Gly Thr
1               5                   10                  15

Pro Leu Thr Leu Thr Cys Thr Ala Ser Gly Phe Thr Ile Thr Asn Tyr
            20                  25                  30

Pro Met Cys Trp Val Arg Gln Ala Pro Gly Glu Gly Leu Glu Trp Ile
        35                  40                  45

Gly Cys Ile Glu Asp Ser Gly Arg Ile Lys Asp Ala Ser Trp Ala Lys
    50                  55                  60

Gly Arg Phe Thr Met Ser Lys Thr Ser Ser Thr Val Asp Leu Lys
65                  70                  75                  80

Leu Thr Ser Pro Thr Thr Glu Asp Thr Ala Thr Tyr Phe Cys Val Arg
                85                  90                  95

Asp Ala Gly Trp Ser Trp Trp Thr Gln Leu Asp Leu Trp Gly Gln Gly
            100                 105                 110

Thr Leu Val Thr Ile Ser Ser Ser Gly Gly Gly Ser Gly Gly
        115                 120                 125

Asp Gly Ser Gly Gly Gly Ser Glu Leu Val Met Thr Gln Thr Pro
    130                 135                 140

Ser Ser Val Ser Ala Ala Val Gly Asp Thr Val Thr Ile Lys Cys Gln
145                 150                 155                 160

Ala Asn Glu Asn Ile Gly Arg Phe Leu Ala Trp Phe Gln Gln Lys Pro
                165                 170                 175

Gly Gln Arg Pro Lys Leu Leu Ile Tyr Ser Ala Ser Ser Leu Ala Ser
            180                 185                 190

Gly Val Ser Ser Arg Phe Ser Gly Ser Gly Tyr Gly Thr Asp Phe Thr
        195                 200                 205

Leu Thr Ile Ser Gly Val His Cys Asp Asp Ala Ala Ser Tyr Tyr Cys
    210                 215                 220
```

Leu Gly Gly Pro Asn Asn Val Val Asp Gly Ala Ser Phe Gly Gly Gly
225                 230                 235                 240

Thr Glu Val Val Val Lys
            245

<210> SEQ ID NO 31
<211> LENGTH: 5
<212> TYPE: PRT
<213> ORGANISM: Unknown
<220> FEATURE:
<223> OTHER INFORMATION: the sequence is Gallus gallus domesticus

<400> SEQUENCE: 31

Ser Phe Asn Met His
1               5

<210> SEQ ID NO 32
<211> LENGTH: 20
<212> TYPE: PRT
<213> ORGANISM: Unknown
<220> FEATURE:
<223> OTHER INFORMATION: the sequence is Gallus gallus domesticus

<400> SEQUENCE: 32

Gly Ile Ser Gly Asp Asp Ser Arg Tyr Thr Tyr Thr Asn Tyr Ala Pro
1               5                   10                  15

Ala Val Lys Gly
            20

<210> SEQ ID NO 33
<211> LENGTH: 13
<212> TYPE: PRT
<213> ORGANISM: Unknown
<220> FEATURE:
<223> OTHER INFORMATION: the sequence is Gallus gallus domesticus

<400> SEQUENCE: 33

Asp Phe Ser Asp Gly Ser Gly Ala Asp His Ile Asp Ala
1               5                   10

<210> SEQ ID NO 34
<211> LENGTH: 8
<212> TYPE: PRT
<213> ORGANISM: Unknown
<220> FEATURE:
<223> OTHER INFORMATION: the sequence is Gallus gallus domesticus

<400> SEQUENCE: 34

Ser Gly Ser Ser Ser Trp Tyr Gly
1               5

<210> SEQ ID NO 35
<211> LENGTH: 7
<212> TYPE: PRT
<213> ORGANISM: Unknown
<220> FEATURE:
<223> OTHER INFORMATION: the sequence is Gallus gallus domesticus

<400> SEQUENCE: 35

Ser Asn Asp Lys Arg Pro Ser
1               5

<210> SEQ ID NO 36
<211> LENGTH: 12
<212> TYPE: PRT

```
<213> ORGANISM: Unknown
<220> FEATURE:
<223> OTHER INFORMATION: the sequence is Gallus gallus domesticus

<400> SEQUENCE: 36

Gly Thr Tyr Asp Ser Ser Ala Arg Tyr Ile Gly Val
1               5                   10

<210> SEQ ID NO 37
<211> LENGTH: 130
<212> TYPE: PRT
<213> ORGANISM: Unknown
<220> FEATURE:
<223> OTHER INFORMATION: the sequence is Gallus gallus domesticus

<400> SEQUENCE: 37

Met Ala Leu Pro Ala Ala Val Thr Leu Asp Glu Ser Gly Gly Leu
1               5                   10                  15

Gln Thr Pro Gly Gly Val Leu Ser Leu Val Cys Lys Ala Ser Gly Phe
                20                  25                  30

Thr Phe Ser Ser Phe Asn Met His Trp Val Arg Gln Ala Pro Gly Lys
            35                  40                  45

Gly Leu Glu Trp Val Ala Gly Ile Ser Gly Asp Ser Arg Tyr Thr
50                  55                  60

Tyr Thr Asn Tyr Ala Pro Ala Val Lys Gly Arg Ala Thr Ile Ser Arg
65                  70                  75                  80

Asp Asn Gly Gln Ser Thr Val Arg Leu Gln Leu Asn Asn Leu Arg Ala
                85                  90                  95

Glu Asp Thr Gly Thr Tyr Tyr Cys Ala Lys Asp Phe Ser Asp Gly Ser
                100                 105                 110

Gly Ala Asp His Ile Asp Ala Trp Gly His Gly Thr Glu Val Ile Val
            115                 120                 125

Ser Ser
    130

<210> SEQ ID NO 38
<211> LENGTH: 116
<212> TYPE: PRT
<213> ORGANISM: Unknown
<220> FEATURE:
<223> OTHER INFORMATION: the sequence is Gallus gallus domesticus

<400> SEQUENCE: 38

Ala Leu Thr Gln Pro Ser Ser Val Ser Ala Asn Pro Gly Glu Thr Val
1               5                   10                  15

Lys Ile Thr Cys Ser Gly Ser Ser Ser Trp Tyr Gly Trp Tyr Gln Gln
                20                  25                  30

Lys Ser Pro Gly Ser Ala Pro Val Thr Val Ile Tyr Ser Asn Asp Lys
            35                  40                  45

Arg Pro Ser Asn Ile Pro Ser Arg Phe Ser Gly Ser Ala Ser Gly Ser
50                  55                  60

Thr Ala Thr Leu Thr Ile Thr Gly Val Gln Val Glu Asp Glu Ala Val
65                  70                  75                  80

Tyr Phe Cys Gly Thr Tyr Asp Ser Ser Ala Arg Tyr Ile Gly Val Phe
                85                  90                  95

Gly Ala Gly Thr Thr Leu Thr Val Leu Ala Ala Ala Leu Glu His His
            100                 105                 110

His His His His
        115
```

```
<210> SEQ ID NO 39
<211> LENGTH: 261
<212> TYPE: PRT
<213> ORGANISM: Unknown
<220> FEATURE:
<223> OTHER INFORMATION: the sequence is Gallus gallus domesticus

<400> SEQUENCE: 39

Met Ala Leu Pro Ala Ala Val Thr Leu Asp Glu Ser Gly Gly Leu
1               5                   10                  15

Gln Thr Pro Gly Gly Val Leu Ser Leu Val Cys Lys Ala Ser Gly Phe
                20                  25                  30

Thr Phe Ser Ser Phe Asn Met His Trp Val Arg Gln Ala Pro Gly Lys
            35                  40                  45

Gly Leu Glu Trp Val Ala Gly Ile Ser Gly Asp Ser Arg Tyr Thr
50                  55                  60

Tyr Thr Asn Tyr Ala Pro Ala Val Lys Gly Arg Ala Thr Ile Ser Arg
65                  70                  75                  80

Asp Asn Gly Gln Ser Thr Val Arg Leu Gln Leu Asn Asn Leu Arg Ala
                85                  90                  95

Glu Asp Thr Gly Thr Tyr Tyr Cys Ala Lys Asp Phe Ser Asp Gly Ser
                100                 105                 110

Gly Ala Asp His Ile Asp Ala Trp Gly His Gly Thr Glu Val Ile Val
                115                 120                 125

Ser Ser Gly Gly Gly Gly Ser Gly Gly Asp Gly Ser Gly Gly Gly Gly
130                 135                 140

Ser Ala Leu Thr Gln Pro Ser Ser Val Ser Ala Asn Pro Gly Glu Thr
145                 150                 155                 160

Val Lys Ile Thr Cys Ser Gly Ser Ser Trp Tyr Gly Trp Tyr Gln
                165                 170                 175

Gln Lys Ser Pro Gly Ser Ala Pro Val Thr Val Ile Tyr Ser Asn Asp
                180                 185                 190

Lys Arg Pro Ser Asn Ile Pro Ser Arg Phe Ser Gly Ser Ala Ser Gly
                195                 200                 205

Ser Thr Ala Thr Leu Thr Ile Thr Gly Val Gln Val Glu Asp Glu Ala
210                 215                 220

Val Tyr Phe Cys Gly Thr Tyr Asp Ser Ser Ala Arg Tyr Ile Gly Val
225                 230                 235                 240

Phe Gly Ala Gly Thr Thr Leu Thr Val Leu Ala Ala Ala Leu Glu His
                245                 250                 255

His His His His His
                260

<210> SEQ ID NO 40
<211> LENGTH: 16
<212> TYPE: PRT
<213> ORGANISM: Artificial Sequence
<220> FEATURE:
<223> OTHER INFORMATION: linker

<400> SEQUENCE: 40

Ser Gly Gly Gly Gly Ser Gly Gly Asp Gly Ser Gly Gly Gly Gly Ser
1               5                   10                  15

<210> SEQ ID NO 41
<211> LENGTH: 37
<212> TYPE: DNA
```

```
<213> ORGANISM: Artificial Sequence
<220> FEATURE:
<223> OTHER INFORMATION: VH region sense primer with Sfi I site

<400> SEQUENCE: 41
ctatgcggcc cagccggccg ccgtgacgtt ggacgag                      37

<210> SEQ ID NO 42
<211> LENGTH: 31
<212> TYPE: DNA
<213> ORGANISM: Artificial Sequence
<220> FEATURE:
<223> OTHER INFORMATION: VH region anti sense primer

<400> SEQUENCE: 42
cctccaccgg aggagacgat gacttcggtc c                            31

<210> SEQ ID NO 43
<211> LENGTH: 34
<212> TYPE: DNA
<213> ORGANISM: Artificial Sequence
<220> FEATURE:
<223> OTHER INFORMATION: VL region sense primer

<400> SEQUENCE: 43
gcggatcggc cctgactcag ccgtcctcgg tgtc                         34

<210> SEQ ID NO 44
<211> LENGTH: 25
<212> TYPE: DNA
<213> ORGANISM: Artificial Sequence
<220> FEATURE:
<223> OTHER INFORMATION: VL region anti sense primer with Not I site

<400> SEQUENCE: 44
acctgcggcc gctaggacgg tcagg                                   25

<210> SEQ ID NO 45
<211> LENGTH: 57
<212> TYPE: DNA
<213> ORGANISM: Artificial Sequence
<220> FEATURE:
<223> OTHER INFORMATION: GS linker sense primer

<400> SEQUENCE: 45
tcctccggtg gaggcggttc aggcggagat ggctctggcg gtggcggatc ggccctg   57

<210> SEQ ID NO 46
<211> LENGTH: 56
<212> TYPE: DNA
<213> ORGANISM: Artificial Sequence
<220> FEATURE:
<223> OTHER INFORMATION: GS linker anti sense primer

<400> SEQUENCE: 46
cagggccgat ccgccaccgc cagagccatc tccgcctgaa ccgcctccac cggagg    56

<210> SEQ ID NO 47
<211> LENGTH: 5
<212> TYPE: PRT
<213> ORGANISM: Unknown
<220> FEATURE:
<223> OTHER INFORMATION: the sequence is Leporidae

<400> SEQUENCE: 47

Asn Tyr Pro Met Cys
```

```
1               5

<210> SEQ ID NO 48
<211> LENGTH: 16
<212> TYPE: PRT
<213> ORGANISM: Unknown
<220> FEATURE:
<223> OTHER INFORMATION: the sequence is Leporidae

<400> SEQUENCE: 48

Cys Ile Glu Asp Ser Gly Arg Ile Lys Asp Ala Ser Trp Ala Lys Gly
1               5                   10                  15

<210> SEQ ID NO 49
<211> LENGTH: 12
<212> TYPE: PRT
<213> ORGANISM: Unknown
<220> FEATURE:
<223> OTHER INFORMATION: the sequence is Leporidae

<400> SEQUENCE: 49

Asp Ala Gly Trp Ser Trp Trp Thr Gln Leu Asp Leu
1               5                   10

<210> SEQ ID NO 50
<211> LENGTH: 11
<212> TYPE: PRT
<213> ORGANISM: Unknown
<220> FEATURE:
<223> OTHER INFORMATION: the sequence is Leporidae

<400> SEQUENCE: 50

Gln Ala Asn Glu Asn Ile Gly Arg Phe Leu Ala
1               5                   10

<210> SEQ ID NO 51
<211> LENGTH: 7
<212> TYPE: PRT
<213> ORGANISM: Unknown
<220> FEATURE:
<223> OTHER INFORMATION: the sequence is Leporidae

<400> SEQUENCE: 51

Ser Ala Ser Ser Leu Ala Ser
1               5

<210> SEQ ID NO 52
<211> LENGTH: 13
<212> TYPE: PRT
<213> ORGANISM: Unknown
<220> FEATURE:
<223> OTHER INFORMATION: the sequence is Leporidae

<400> SEQUENCE: 52

Cys Leu Gly Gly Pro Asn Asn Val Val Asp Gly Ala Ser
1               5                   10

<210> SEQ ID NO 53
<211> LENGTH: 121
<212> TYPE: PRT
<213> ORGANISM: Unknown
<220> FEATURE:
<223> OTHER INFORMATION: the sequence is Leporidae

<400> SEQUENCE: 53

Ala Gln Ser Val Lys Glu Ser Gly Gly Arg Leu Val Thr Pro Gly Thr
1               5                   10                  15
```

```
Pro Leu Thr Leu Thr Cys Thr Ala Ser Gly Phe Thr Ile Thr Asn Tyr
            20                  25                  30

Pro Met Cys Trp Val Arg Gln Ala Pro Gly Glu Gly Leu Glu Trp Ile
        35                  40                  45

Gly Cys Ile Glu Asp Ser Gly Arg Ile Lys Asp Ala Ser Trp Ala Lys
    50                  55                  60

Gly Arg Phe Thr Met Ser Lys Thr Ser Ser Thr Val Asp Leu Lys
65                  70                  75                  80

Leu Thr Ser Pro Thr Thr Glu Asp Thr Ala Thr Tyr Phe Cys Val Arg
                85                  90                  95

Asp Ala Gly Trp Ser Trp Trp Thr Gln Leu Asp Leu Trp Gly Gln Gly
            100                 105                 110

Thr Leu Val Thr Ile Ser Ser Ser Ser
            115                 120

<210> SEQ ID NO 54
<211> LENGTH: 110
<212> TYPE: PRT
<213> ORGANISM: Unknown
<220> FEATURE:
<223> OTHER INFORMATION: the sequence is Leporidae

<400> SEQUENCE: 54

Glu Leu Val Met Thr Gln Thr Pro Ser Ser Val Ser Ala Ala Val Gly
1               5                   10                  15

Asp Thr Val Thr Ile Lys Cys Gln Ala Asn Glu Asn Ile Gly Arg Phe
            20                  25                  30

Leu Ala Trp Phe Gln Gln Lys Pro Gly Gln Arg Pro Lys Leu Leu Ile
        35                  40                  45

Tyr Ser Ala Ser Ser Leu Ala Ser Gly Val Ser Ser Arg Phe Ser Gly
    50                  55                  60

Ser Gly Tyr Gly Thr Asp Phe Thr Leu Thr Ile Ser Gly Val His Cys
65                  70                  75                  80

Asp Asp Ala Ala Ser Tyr Tyr Cys Leu Gly Gly Pro Asn Asn Val Val
                85                  90                  95

Asp Gly Ala Ser Phe Gly Gly Gly Thr Glu Val Val Val Lys
            100                 105                 110
```